(12) United States Patent
Ban et al.

(10) Patent No.: US 7,491,739 B2
(45) Date of Patent: *Feb. 17, 2009

(54) TNF-α PRODUCTION INHIBITORS

(75) Inventors: Masakazu Ban, Osaka (JP); Hiroshi Suhara, Osaka (JP); Masato Horiuchi, Osaka (JP); Noriyoshi Yamamoto, Osaka (JP); Hiroshi Enomoto, Osaka (JP); Hiroyuki Inoue, Osaka (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 76 days.

This patent is subject to a terminal disclaimer.

(21) Appl. No.: 11/448,634

(22) Filed: Jun. 7, 2006

(65) Prior Publication Data
US 2006/0229342 A1    Oct. 12, 2006

Related U.S. Application Data

(62) Division of application No. 10/168,777, filed as application No. PCT/JP01/04586 on May 31, 2001, now Pat. No. 7,098,226.

(30) Foreign Application Priority Data

May 31, 2000    (JP) ............................. 2000-162945

(51) Int. Cl.
*A61K 31/44* (2006.01)
*C07D 213/04* (2006.01)
(52) U.S. Cl. ................. 514/357; 546/332; 546/329
(58) Field of Classification Search ............. 514/357; 546/332, 329
See application file for complete search history.

(56) References Cited

U.S. PATENT DOCUMENTS

| | | | |
|---|---|---|---|
| 3,682,922 | A | 8/1972 | Klimstra |
| 4,597,902 | A | 7/1986 | Shanklin, Jr. et al. |
| 4,724,235 | A | 2/1988 | Shanklin, Jr. et al. |
| 5,173,506 | A | 12/1992 | Neustadt et al. |
| 5,190,974 | A | 3/1993 | Clemence et al. |
| 5,356,925 | A | 10/1994 | Neustadt et al. |
| 5,599,944 | A | 2/1997 | Muller et al. |
| 5,674,864 | A | 10/1997 | Clemence et al. |
| 6,033,443 | A | 3/2000 | Aeschlimann |
| 6,034,096 | A | 3/2000 | Bertolini et al. |
| 6,420,398 | B2 | 7/2002 | Mita et al. |
| 6,492,370 | B1 | 12/2002 | Mita et al. |
| 2001/0041725 | A1 | 11/2001 | Mita et al. |
| 2002/0077357 | A1 | 6/2002 | Mita et al. |
| 2002/0198376 | A1 | 12/2002 | Mita et al. |
| 2005/0014800 | A1 | 1/2005 | Matsuoka et al. |

FOREIGN PATENT DOCUMENTS

| | | |
|---|---|---|
| EP | 0 849 256 A1 | 6/1998 |
| EP | 0 903 434 A | 3/1999 |
| EP | 1072591 A | 1/2001 |
| EP | 1103543 A | 5/2001 |
| EP | 1 457 205 A | 9/2004 |
| JP | 9-508115 A | 8/1997 |
| WO | WO 92/03410 A | 3/1992 |
| WO | WO 92/07567 A1 | 5/1992 |
| WO | WO 95/19957 A | 7/1995 |
| WO | WO 97/24328 A | 7/1997 |
| WO | WO 97/24355 A | 7/1997 |
| WO | WO 97/43251 A1 | 11/1997 |
| WO | WO 98/27069 A | 6/1998 |
| WO | WO 99/50238 A | 10/1999 |
| WO | WO 00/07985 A | 2/2000 |
| WO | WO 00/61552 A | 10/2000 |

OTHER PUBLICATIONS

Kurose et al., "Asymmetric [2,3]Sigmatropic Rearrangement of Chiral Allyic Selenimides", *J. Org. Chem.*, (1996), vol. 61, pp. 2932-2933, XP001157480.

Braña et al., "Synthesis of 1,2-Di-(4-pyridyl)ethylenediamine and Related Compounds", *J. Heterocycl. Chem.*, (1987), vol. 24, pp. 369-371, XP009010907.

Mayer et al., "183. Structural Factors Affecting the Basicity of ω-Pyridylalkanols, ω-Pyridylalkanamides and ω-Pyridylalkylamines", *Helvetica Chimica Acta*, (1982), vol. 65, Fasc. 6, No. 183, pp. 1868-1884, XP009010908.

A.R. Katritzky, "An Attempt to Simulate the Biogenesis of Stychnine. Part II. Preparation and Transformations of 3-(2-4'-Pyridylacetamidoethyl)indole.", (1955), pp. 2586-2593, XP009010909.

Böhme et al., "α-Alkylmercapto- and α-Aryolmercapto-alkylisocyanate", *Archiv Pharm. Ber. Dtsch. Pharm. Ges.*, (1969), vol. 302, No. 5, pp. 335-339, XP009010911.

Shoeb et al., "Studies in Possible Oral Hypoglycaemic Agents: Part V-Synthesis of Carbamoylindoles, Carbamoylisoindolines, 3-Indolylethyl Urea (or Thiourea) & 2- Isoindolinylpropyl Urea (or Thiourea) Derivatives & Their Biological Activity", *J. Chem.*, (1967), vol. 5, pp. 142-144, XP009010912.

(Continued)

*Primary Examiner*—Charanjit S Aulakh
(74) *Attorney, Agent, or Firm*—Frishauf, Holtz, Goodman & Chick, P.C.

(57) ABSTRACT

A purpose of the present invention is to provide TNF-α production inhibitors being useful as therapeutic agents for autoimmune diseases such as rheumatoid arthritis. Novel compounds having the structure represented by the general formula [1] or salts thereof according to the present invention have excellent TNF-α production inhibitory activities,

[1]

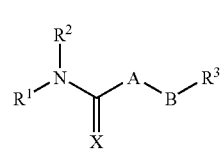

wherein "A" is —(NR$^4$)—, —(CR$^5$R$^6$)— or —O—, "B" is alkylene or alkenylene, R$^1$, R$^2$, R$^4$, R$^5$ and R$^6$ are hydrogen, alkyl, alkenyl, adamantyl or the like, R$^3$ is aryl or an unsaturated heterocycle, and "X" is oxygen or sulfer respectively.

9 Claims, No Drawings

OTHER PUBLICATIONS

Kunz et al., "Der. 2-(4-Pyridyl)Ethoxycarbonyl-(4-Pyoc)-Rest-Eine Hydrophile . . . ", *Tetrahedron Letters*, (1984), vol. 25, No. 33, pp. 3567-3570, XP009010914.

Starnes, S.D.; Rudkevich, D.M.; Rebek, J. Jr., "A Cavitand-Porphyrin Hybrid", Org. Lett., 2000, vol. 2, No. 14, pp. 1995-1998.

Yamazaki, Clinical Immunology, 27, pp. 1270-1273 (1995) and English language Abstract thereof.

Andreas Eigler et al, Immunology Today, 18, pp. 487-492, (1997).

TNF-α PRODUCTION INHIBITORS

This application is a Divisional Application of application Ser. No. 10/168,777 filed Jun. 21, 2002 now U.S. Pat. No. 7,098,226, which is the U.S. national phase application of International Application PCT/JP01/04586 filed May 31, 2001 which is hereby incorporated in its entirety herein by this reference.

TECHNICAL FIELD

The present invention relates to TNF-α production inhibitors being useful as therapeutic agents for autoimmune diseases such as rheumatoid arthritis.

BACKGROUND ART

TNF-α (Tumor necrosis factor-α) is recognized as a cytokine which widely participates in biophylaxis-immune mechanism through inflammation. It is known that prolonged and excessive production of TNF-α is a factor which brings about causes of tissue damage and various diseases. Examples of pathology in which TNF-α participates are many pathology such as arthrorheumatism, systemic lupus erythematosus (SLE), cachexia, acute infectious disease, allergy, pyrexia, anemia and diabetes (Yamazaki, Clinical Immunology, 27, 1270, 1995). It is also reported that TNF-α plays an important role in pathogenesis of rheumatoid arthritis and Crohn's disease, which are autoimmune diseases (Andreas Eigler et al., Immunology Today, 18, 487, 1997).

From these reports, compounds which inhibit or suppress TNF-α production are expected to be effective for treatment of the above-mentioned diseases, and various studies have been done (the above-mentioned literatures: Yamazaki, Clinical Immunology, 27, 1270, 1995, Andreas Eigler et al., Immunology Today, 18, 487, 1997). Recently, it was also reported that metalloprotease, which is a proteolytic enzyme, participates in secretion of TNF-α and metalloprotease inhibitors have important effects on the inhibition of TNF-α production and the like (Published Japanese Translation of PCT No. 508115/1997). Japanese Laid-open Patent Publication Nos. 44533/2000 and 119249/2000 disclose compounds having inhibitory effects of TNF-α production. All of these compounds are urea derivatives having a sulfur atom in side chains.

It is meaningful to search compounds having inhibitory activities of TNF-α production and being useful as therapeutic agents for the autoimmune diseases such as rheumatoid arthritis, allergy and diabetes.

DISCLOSURE OF THE INVENTION

The present inventors prepared compounds having various chemical structures and carried out pharmacological tests. As a result, the present inventors found that novel compounds having structure represented by the following general formula [1] exhibit excellent inhibitory activities of TNF-α production to attain the present invention.

The present invention relates to compounds represented by the following general formula [1] and salts thereof (hereinafter referred to as "the present compound" as far as there is no proviso), and pharmaceutical compositions comprising it as an active ingredient,

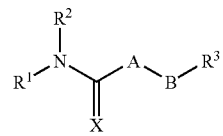

wherein "A" is —(NR$^4$)—, —(CR$^5$R$^6$)— or —O—;
"B" is alkylene or alkenylene which can contain —O—, —S—, —(NR$^7$)—, —CO—, —N= or a group represented by the following formula in its chain,

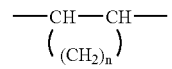

wherein the alkylene and alkenylene can be substituted by hydroxy, alkoxy, cycloalkyl, aryl, siloxy or a saturated or unsaturated heterocycle and "B" can form a saturated heterocycle with "A";

R$^1$, R$^2$, R$^4$, R$^5$ and R$^6$, being the same or different, are hydrogen, alkyl, alkenyl, alkynyl, cycloalkyl, cycloalkenyl, hydroxy, acyl or amino, wherein the alkyl, alkenyl, alkynyl, cycloalkyl or cycloalkenyl can be substituted by halogen, hydroxy, amino, cycloalkyl, adamantyl, aryl, carboxy, alkoxycarbonyl, aryloxycarbonyl, aminocarbonyl, cyano or a saturated or unsaturated heterocycle;

R$^1$ and R$^2$, R$^2$ and R$^4$, R$^2$ and R$^6$, and R$^2$ and R$^6$ each can form a saturated or unsaturated heterocycle;

R$^3$ is aryl or an unsaturated heterocycle;
R$^7$ is hydrogen or alkyl;
"X" is O or S;
"n" is an integer of 1 to 5; and Each hydrogen of the above-mentioned amino, hydroxy and aminocarbonyl can be substituted by alkyl, cycloalkyl, adamantyl, adamantylalkyl, aryl, arylalkyl, acyl, alkoxyalkyl, alkoxycarbonyl, alkylaminocarbonyl, cycloalkyloxycarbonyl, arylalkoxycarbonyl, alkylsulfonyl, arylsulfonyl, halogenoalkyloxycarbonyl, imidazolylcarbonyl, pyridylcarbonyl, a saturated or unsaturated heterocycle, or alkyl substituted by a saturated or unsaturated heterocycle. The same definitions are applied hereinafter.

The present compounds represented by the above general formula [1] are appropriate to constitute pharmaceutical compositions and are active ingredients of TNF-α production inhibitors being useful as therapeutic agents for autoimmune diseases such as rheumatoid arthritis, allergy and diabetes.

Each group defined in the general formula [1] is described in detail.

The alkylene is straight-chain or branched alkylene having one to 12 carbon atoms such as methylene, ethylene, trimethylene, propylene, tetramethylene, pentamethylene, hexamethylene, octamethylene, decamethylene, dodecamethylene, methylmethylene, ethylethylene, dimethylethylene, propylethylene, isopropylethylene or methyltrimethylene.

The alkenylene is straight-chain or branched alkenylene having one or more double bond and two to 12 carbon atoms such as vinylene, propenylene, butenylene, pentenylene, hexenylene, octenylene, butanediylidene or methylpropenylene.

The alkyl is straight-chain or branched alkyl having one to 12 carbon atoms such as methyl, ethyl, propyl, butyl, pentyl, hexyl, octyl, decyl, dodecyl, isopropyl, isobutyl, isopentyl, isohexyl, isooctyl, t-butyl or 3,3-dimethylbutyl.

The alkoxy is straight-chain or branched alkoxy having one to 12 carbon atoms such as methoxy, ethoxy, propoxy, butoxy, hexyloxy, octyloxy, decyloxy, dodecyloxy, isopropoxy or t-butoxy.

The alkenyl is straight-chain or branched alkenyl having two to 12 carbon atoms such as vinyl, allyl, 3-butenyl, 5-hexenyl or isopropenyl.

The alkynyl is straight-chain or branched alkynyl having two to 12 carbon atoms such as ethynyl, propynyl or butynyl.

The cycloalkyl is cycloalkyl having three to 20 carbon atoms such as cyclopropyl, cyclobutyl, cyclopentyl, cyclohexyl, cycloheptyl, cyclooctyl, cyclodecyl or cyclododecyl.

The cycloalkenyl is cycloalkenyl having 5 to 20 carbon atoms such as cyclopentenyl, cyclohexenyl or cycloheptenyl.

The aryl is an aromatic hydrocarbon ring such as phenyl or naphtyl, and the ring can have one or more substituent. Examples of the substituent are alkyl, cycloalkyl, carboxy, amino, hydroxy, aminoalkyl, hydroxyalkyl, nitro, cyano, halogen, alkyloxy and the like.

The siloxy is an organic group containing silicon such as trialkylsilyloxy, dialkyl(aryl)silyloxy, alkyl(diaryl)oxy or triarylsilyloxy.

The halogen is fluorine, chlorine, bromine or iodine.

The heterocycle is, for example, a saturated or unsaturated five to twenty-membered monocyclic or bicyclic heterocycle containing one to four nitrogen, oxygen and/or sulfur. The heterocycle can have one or more substituent. Examples of the substituent are alkyl, cycloalkyl, carboxy, amino, hydroxy, aminoalkyl, hydroxyalkyl, nitro, cyano, halogen, alkyloxy, aryl, arylalkyl, a saturated or unsaturated heterocycle and the like. When the above-mentioned heterocycle has nitrogen or sulfur in its ring, the atom can be oxidized to be in the form of N-oxide, S-oxide or the like.

Specific examples of the saturated heterocycle are monocyclic heterocycles such as pyrrolidine, piperidine, homopiperidine and piperazine, which have nitrogen in their ring, morpholine, which has nitrogen and oxygen in its ring, and thiomorpholine, which has nitrogen and sulfur in its ring. These can condense with a benzene ring and the like to form bicyclic heterocycles such as tetrahydroquinoline and tetrahydroisoquinoline.

Specific examples of the unsaturated heterocycle are monocyclic heterocycles such as pyrrole, pyridine, pyrazole, imidazole, pyrazine, pyridazine and pyrimidine, and bicyclic heterocycles such as indole, quinoline, isoquinoline, benzimidazole, naphthyridine, pyrrolopyridine and imidazopyridine, which have nitrogen in their ring, monocyclic heterocycles such as furan, and bicyclic heterocycles such as benzofuran, which have oxygen in their ring, monocyclic heterocycles such as thiophene, and bicyclic heterocycles such as benzothiophene, which have sulfur in their ring, monocyclic heterocycles such as oxazole, isoxazole, thiazole and isothiazole, and bicyclic heterocycles such as benzoxazole, benzothiazole, thienopyridine, oxazolopyridine, thiazolopyridine and furopyridine, which have nitrogen and oxygen or sulfur in their ring, and the like. Further, the above-mentioned unsaturated heterocycles can contain saturated bonds partially.

Salts in the present invention refer to any pharmaceutically acceptable salts and are exemplified by salts with an inorganic acid such as hydrochloric acid, nitric acid, sulfuric acid or phosphoric acid, salts with an organic acid such as acetic acid, fumaric acid, maleic acid, succinic acid or tartaric acid, salts with an alkali metal or an alkaline-earth metal such as sodium, potassium or calcium, and the like. Quaternary ammonium salts of the present compounds are also included in the salts in the present invention. Further when there are geometrical isomers or optical isomers in the present compounds, these isomers are also included in the scope of the present invention. The present compounds can be in the form of hydrates and solvates.

Preferred examples in the present invention are the following compounds (1) to (3).

(1) Compounds or salts thereof wherein each group defined by the general formula [1] is selected from the following 1) to 4) or the groups are defined by combinations of two or more of 1) to 4).

1) $R^3$: a pyridine ring.
  2) At least one of $R^1$, $R^2$, $R^4$, $R^5$ and $R^6$: adamantylalkyl, adamantyloxyalkyl, adamantylaminoalkyl or adamantylaminocarbonylalkyl.
  3) At least one of $R^1$ and $R^2$: adamantylalkyl, adamantyloxyalkyl, adamantylaminoalkyl or adamantylaminocarbonylalkyl.
  4) At least one of $R^1$ and $R^2$: adamantylalkyl.

(2) Compounds or salts thereof wherein the respective groups defined by the general formula [1] are the following groups, A: —(NR$^4$)—, —(CR$^5$R$^6$)— or —O—,
  B: alkylene or alkenylene which can contain —O—, —S—, —(NR$^7$)—, —CO—, —N= or a group represented by the following formula in its chain,

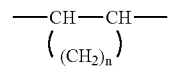

wherein the alkylene can be substituted by hydroxy, alkoxy, aryl, siloxy or a saturated or unsaturated heterocycle and "B" can form a saturated heterocycle with "A", $R^1$: hydrogen, alkyl, alkenyl, alkynyl, cycloalkyl, cycloalkenyl, hydroxy or amino, wherein the alkyl, alkenyl, alkynyl, cycloalkyl or cycloalkenyl can be substituted by halogen, hydroxy, amino, cycloalkyl, aryl, carboxy, alkoxycarbonyl, alkylaminocarbonyl, adamantyl, aryloxycarbonyl, cyano or saturated or unsaturated heterocycle, and each hydrogen of the amino, hydroxy and aminocarbonyl in $R^1$ can be substituted by alkyl, cycloalkyl, aryl, arylalkyl, acyl, alkoxycarbonyl, cycloalkyloxycarbonyl, arylalkoxycarbonyl, halogenoalkyloxycarbonyl, imidazolylcarbonyl, an unsaturated heterocycle, or alkyl substituted by an unsaturated heterocycle, $R^2$: adamantylalkyl, adamantyloxyalkyl, adamantylaminoalkyl or adamantylaminocarbonylalkyl, $R^3$: an unsaturated heterocycle, $R^4$: hydrogen, alkyl, adamantylalkyl, carboxyalkyl, alkoxycarbonyl, alkoxycarbonylalkyl, amino, alkylamino, acylamino or alkoxycarbonylamino, $R^5$ and $R^6$: being the same or different, hydrogen, alkyl, amino or alkoxycarbonylamino, $R^7$: hydrogen or alkyl, X: O or S, n: an integer of 1 to 5.

Compounds or salts thereof wherein $R^2$ is adamantylalkyl and $R^3$ is a pyridine ring are more preferable among them.

Further, compounds or salts thereof wherein the respective groups defined by the general formula [1] are the following groups are particularly preferable.

A: —(NR$^4$)—, —(CR$^5$R$^6$)— or —O—,
  B: alkylene or alkenylene which can contain —S— or a group represented by the following formula in its chain,

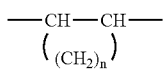

R$^1$: alkyl or alkenyl, wherein the alkyl can be substituted by halogen or amino, and further the amino can be substituted by alkyl, acyl, arylalkyloxycarbonyl, cycloalkyloxycarbonyl or alkoxycarbonyl,
R$^2$: adamantylalkyl,
R$^3$: a pyridine ring,
R$^4$: hydrogen,
R$^5$ and R$^6$: hydrogen,
X: O,
n: an integer of 1 to 5.

(3) Compounds or salts thereof wherein the respective groups defined by the general formula [1] are the following groups,
A: —(NR$^4$)—, —(CR$^5$R$^6$)— or —O—,
B: alkylene or alkenylene which can contain —O—, —S—, —(NR$^7$)—, —N= or a group represented by the following formula in its chain,

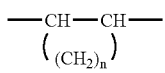

wherein the alkylene can be substituted by hydroxy, alkoxy, aryl or a saturated or unsaturated heterocycle and "B" can form a saturated heterocycle with "A",
R$^1$: hydrogen, alkyl, alkenyl, alkynyl, cycloalkyl, cycloalkenyl, hydroxy or amino, wherein the alkyl, alkenyl, alkynyl, cycloalkyl or cycloalkenyl can be substituted by halogen, hydroxy, amino, cycloalkyl, aryl, carboxy, alkoxycarbonyl, aryloxycarbonyl, aminocarbonyl, cyano or a saturated or unsaturated heterocycle, and each hydrogen of the amino, hydroxy and aminocarbonyl of R$^1$ can be substituted by alkyl, cycloalkyl, aryl, arylalkyl, acyl, alkoxycarbonyl, cycloalkyloxycarbonyl, arylalkoxycarbonyl, an unsaturated heterocycle, or alkyl substituted by an unsaturated heterocycle,
R$^2$: alkyl, alkenyl, cycloalkyl, cycloalkylalkyl or arylalkyl,
R$^3$: a pyridine ring,
R$^4$: hydrogen, alkyl, adamantylalkyl, carboxyalkyl, alkoxycarbonylalkyl, amino, alkylamino, acylamino or alkoxycarbonylamino,
R$^5$ and R$^6$: being the same or different, hydrogen or alkyl,
R$^7$: hydrogen or alkyl,
X: O or S,
n: an integer of 1 to 5.

Compounds or salts thereof wherein the respective groups defined by the general formula [1] are the following groups are more preferable among them.
A: —(NR$^4$)— or —(CR$^5$R$^6$)—,
B: alkylene or alkenylene,
R$^1$: alkyl or alkenyl, wherein the alkyl can be substituted by halogen, amino, cycloalkyl, aryl, imidazolyl or a pyridine ring, and further the amino can be substituted by alkyl, acyl, alkoxycarbonyl, cycloalkyloxycarbonyl or arylalkoxycarbonyl,
R$^2$: alkyl, alkenyl or arylalkyl,
R$^3$: a pyridine ring,
R$^4$: hydrogen,
R$^5$ and R$^6$: hydrogen,
X: O.

Further, compounds or salts thereof wherein R$^1$ is alkyl having three or more carbon atoms and R$^2$ is alkyl or arylalkyl are particularly preferable among them.

Compounds or salts thereof wherein the respective groups defined by the general formula [1] are the following groups are more preferable.
A: —(NR$^4$)— or —(CR$^5$R$^6$)—,
B: alkylene or alkenylene,
R$^1$: alkyl, alkenyl or cycloalkyl, wherein the alkyl can be substituted by halogen, hydroxy, amino, cycloalkyl, aryl, carboxy, alkoxycarbonyl, aryloxycarbonyl, aminocarbonyl, a pyridine ring or a thiophene ring, and further each hydrogen of the amino, hydroxy and aminocarbonyl in R$^1$ can be substituted by alkyl, aryl, arylalkyl, acyl, alkoxycarbonyl, cycloalkyloxycarbonyl or arylalkoxycarbonyl,
R$^2$: cycloalkyl or cycloalkylalkyl,
R$^3$: a pyridine ring,
R$^4$: hydrogen,
R$^5$ and R$^6$: hydrogen,
X: O.

The most preferred specific examples of the present compounds are the following compounds and salts thereof.

1-[2-(1-Adamantyl)ethyl]-1-pentyl-3-[3-(4-pyridyl)propyl]urea

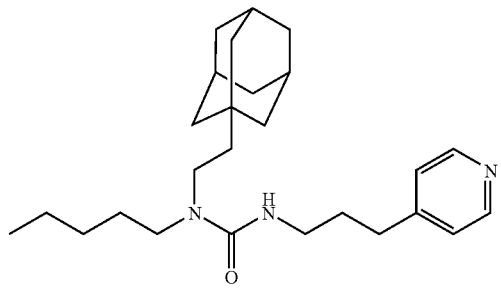

1-[2-(1-Adamantyl)ethyl]-3-[3-(4-pyridyl)propyl]-1-(3,3,3-trifluoropropyl)urea

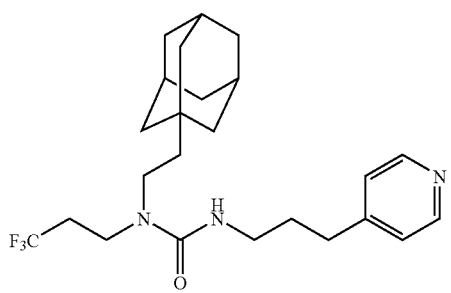

7
1-[2-(1-Adamantyl)ethyl]-1-(2-butenyl)-3-[3-(4-pyridyl)propyl]urea
8
(Z)-1-[2-(1-Adamantyl)ethyl]-1-pentyl-3-[3-(4-pyridyl)-2-propenyl]urea
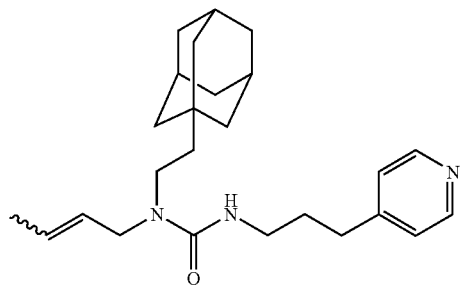
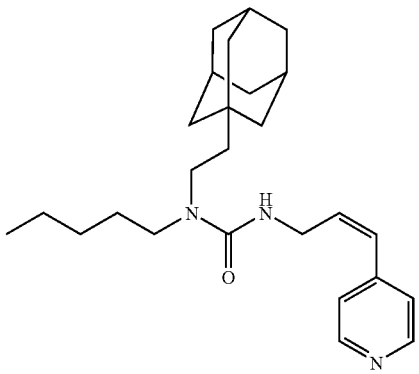
1-[2-(1-Adamantyl)ethyl]-1-[2-[N-(t-butoxycarbonyl)-N-methylamino]ethyl]-3-[3-(4-pyridyl)propyl]urea
(−)-1-[2-(1-Adamantyl)ethyl]-3-[2-methyl-3-(4-pyridyl)propyl]-1-pentylurea
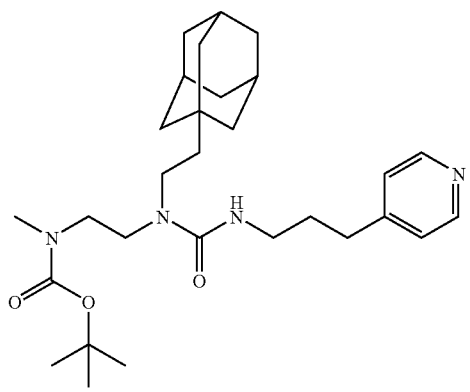
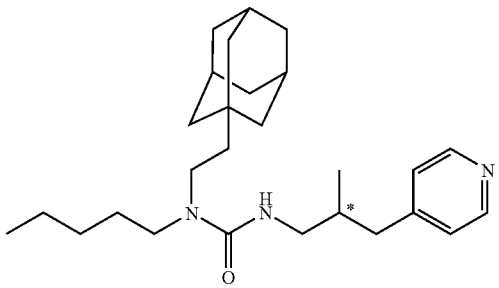
1-[2-(1-Adamantyl)ethyl]-3-[1-methyl-3-(4-pyridyl)propyl]-1-pentylurea
1-[3-(1-Adamantyl)propyl]-1-propyl-3-[3-(4-pyridyl)propyl]urea
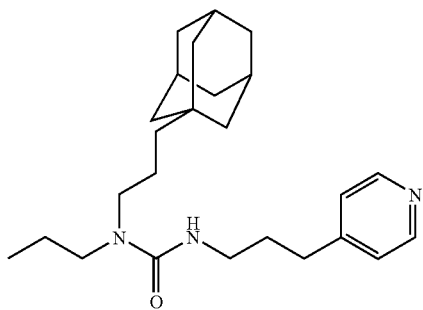
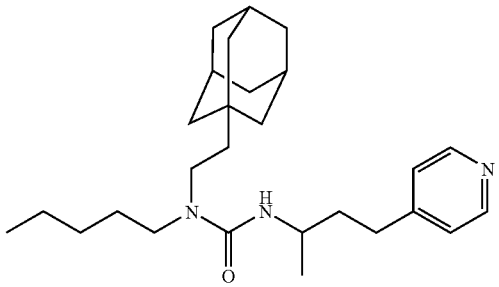

(+)-1-[2-(1-Adamantyl)ethyl]-1-[2-[N-(t-butoxycarbonyl)-N-methylamino]ethyl]-3-[2-methyl-3-(4-pyridyl)propyl]urea

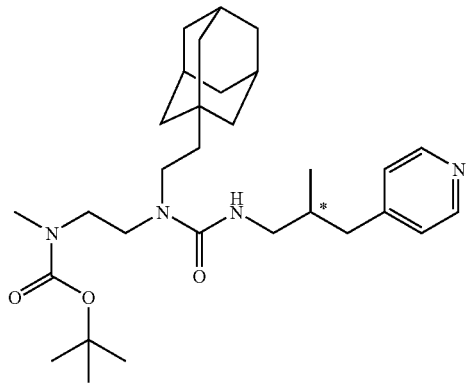

5-(4-Pyridyl)valeric acid N-[2-(1-adamantyl)ethyl]-N-pentylamide

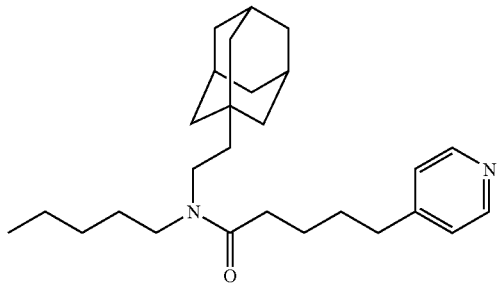

3-(4-Pyridylmethylthio)propionic acid N-[2-(1-adamantyl)ethyl]-N-pentylamide

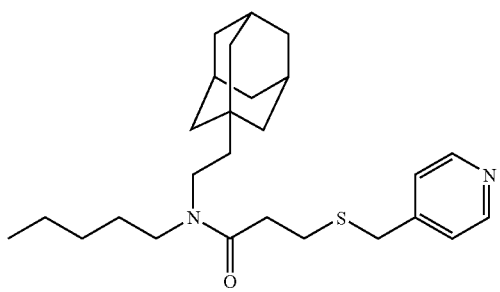

2-[2-(4-Pyridyl)ethylthio]acetic acid N-[2-(1-adamantyl)ethyl]-N-pentylamide

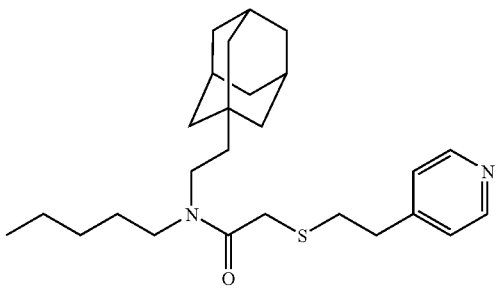

6-(4-Pyridyl)caproic acid N-[2-(1-adamantyl)ethyl]-N-pentylamide

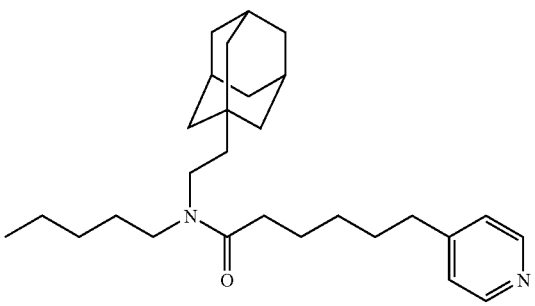

cis-1-[2-(1-Adamantyl)ethyl]-1-pentyl-3-[2-(4-pyridyl)cyclopropylmethyl]urea

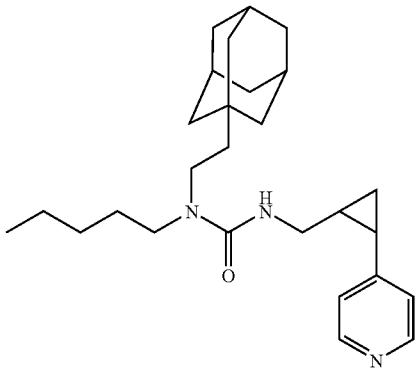

1-[2-(1-Adamantyl)ethyl]-3-[2-methyl-3-(4-pyridyl)propyl]-1-pentylurea

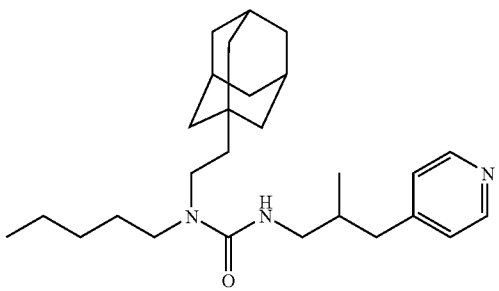

11

1-[2-(1-Adamantyl)ethyl]-1-[2-[N-(t-butoxycarbonyl)-N-methylamino]ethyl]-3-[2-methyl-3-(4-pyridyl)propyl]urea

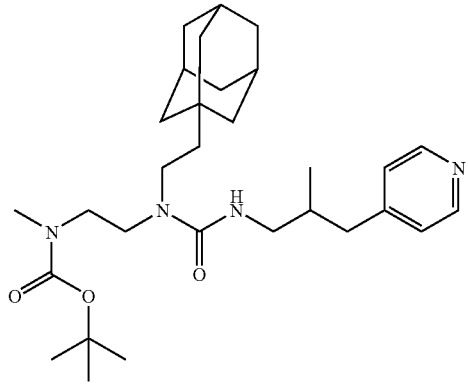

(E)-1-[2-(1-Adamantyl)ethyl]-1-pentyl-3-[3-(4-pyridyl)-2-propenyl]urea

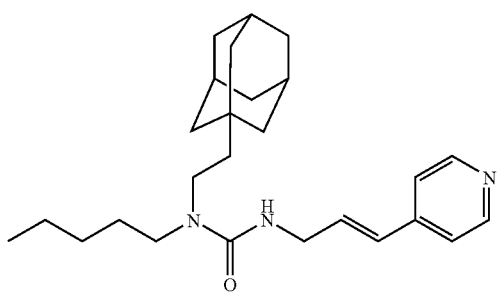

(+)-1-[2-(1-Adamantyl)ethyl]-3-[2-methyl-3-(4-pyridyl)propyl]-1-pentylurea

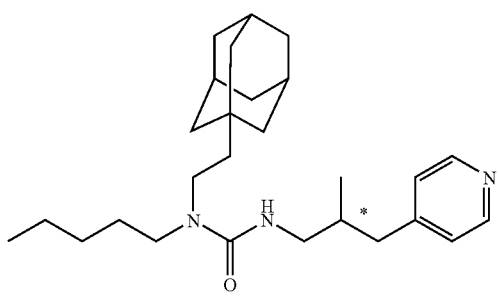

1,1-Dibutyl-3-[3-(4-pyridyl)propyl]urea

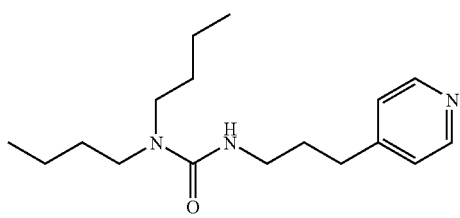

12

3-[2-Methyl-3-(4-pyridyl)propyl]-1-pentyl-1-phenethylurea

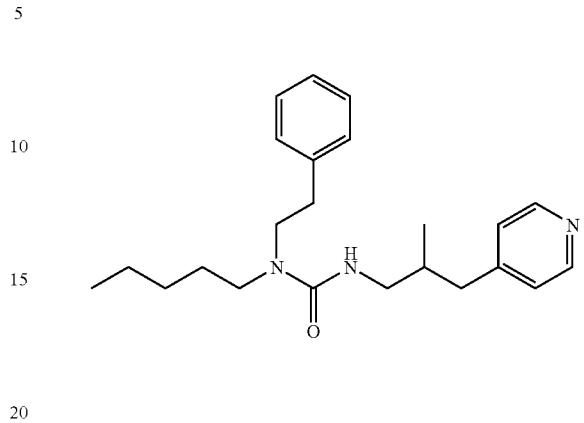

5-(4-Pyridyl)valeric acid N-pentyl-N-phenethylamide 1-(2-Cyclohexylethyl)-3-[2-methyl-3-(4-pyridyl)propyl]-1-pentylurea

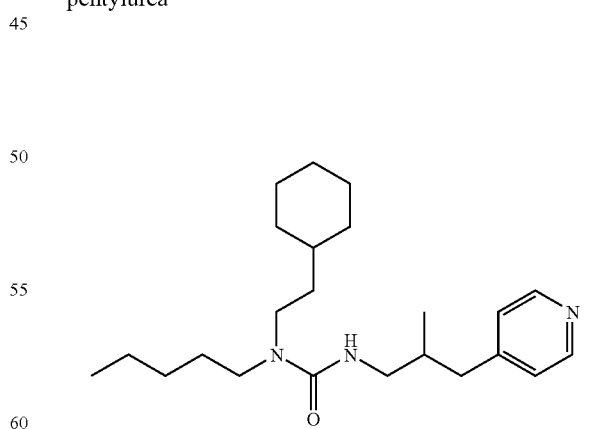

The present compounds can be prepared, for example, according to the following reaction routes 1 to 3. The present compounds can be prepared by not only these reaction routes but also various reaction routes. Detailed synthetic methods will be described in the later Examples.

Reaction route 1

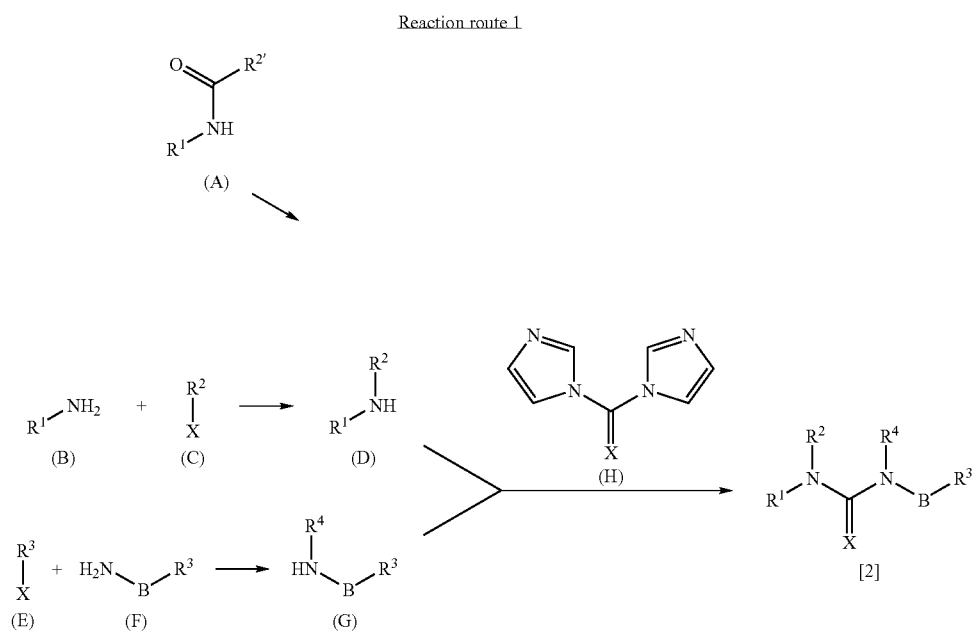

The secondary amine (D) can be obtained by reducing the amide (A) or by reacting the primary amine (B) with the compound (C) having a leaving group. (The secondary amine can be also synthesized using compounds with $R^1$ and $R^2$ reversed in the above chemical reaction formula.) The secondary amine (G) can be obtained by reacting the compound (E) having a leaving group with the primary amine (F) similarly. The present compound [2] is obtained by reacting the primary amine (B) or the secondary amine (D) with the primary amine (F) or the secondary amine (G) in the presence of the condensing agent (H) (for example, 1,1'-carbonyldiimidazole).

Reaction route 2

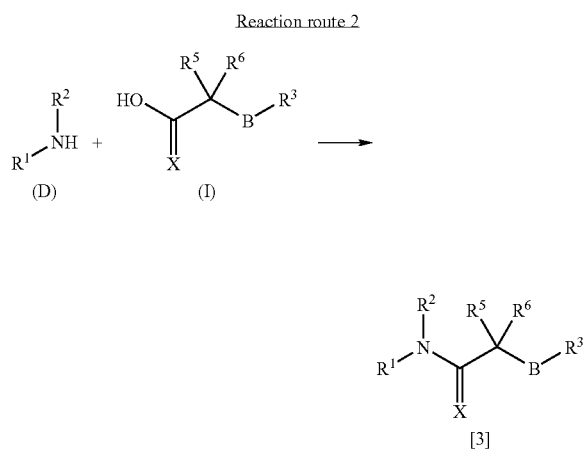

The present compound [3] is obtained by reacting the primary amine (B) or the secondary amine (D) synthesized by the reaction route 1 with the carboxylic acid (I) in the presence of a condensing agent (for example, 1-ethyl-3-(3-dimethylaminopropyl)carbodiimide hydrochloride).

Reaction route 3

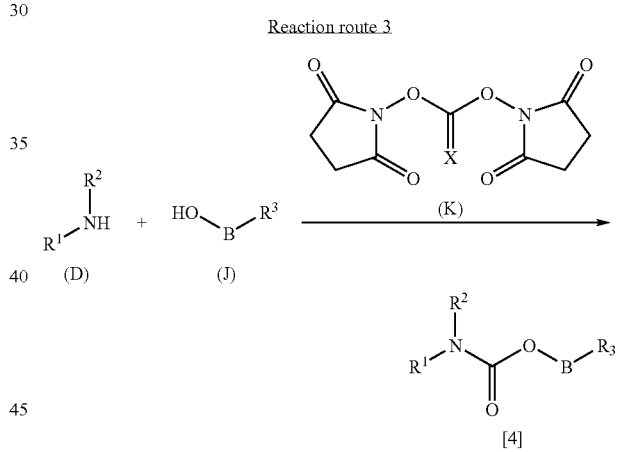

The present compound [4] is obtained by reacting the primary amine (B) or the secondary amine (D) synthesized by the reaction route 1 with the alcohol (J) in the presence of a condensing agent (for example, N,N'-disuccinimidyl carbonate).

In the above-mentioned synthetic methods, when the reactant has a thiol, hydroxy or amino group in its molecule, these groups can be protected with suitable protecting groups, if necessary, and these protecting groups can also be removed by the conventional method after reaction. When the reactant has a carboxyl group in its molecule, the carboxyl group can be esterified, if necessary, and the ester can also be converted into a carboxylic acid by hydrolysis or other general methods.

The compounds obtained by the above-mentioned synthetic methods can be converted into the above-mentioned salts by the conventional method.

The inhibitory effects of TNF-α production were examined in order to study utility of the present compounds obtained by the above-mentioned synthetic methods. Details will be described in the section of "Pharmacological test" below. Studying in vivo inhibitory effects on release of TNF-α caused by stimulation of lipopolysaccharide (LPS), the present compounds exhibited the excellent inhibitory effects of TNF-α production.

TNF-α production is known to be closely related to pathogenesis of autoimmune diseases such as rheumatoid arthritis, Crohn's disease and systemic lupus erythematosus, cachexia, acute infectious disease, allergy, pyrexia, anemia, diabetes and the like. Compounds which inhibit production of TNF-α like the present compounds are expected to be useful for treatment of these various diseases.

The present invention provides a method of inhibiting TNF-α production, a method of treating the autoimmune diseases and a method of treating rheumatic diseases comprising administering to a patient a composition comprising an effective amount of the present compound or a pharmacologically acceptable salts thereof and a pharmacologically acceptable additive.

The present compound can be administered orally or parenterally. Examples of dosage forms are tablets, capsules, granules, powders, injections and the like. The present compound can be formulated into preparations by the conventional methods. For example, oral preparations such as tablets, capsules, granules and powders can be produced by adding optionally a diluent such as lactose, crystalline cellulose, starch or vegetable oil; a lubricant such as magnesium stearate or talc; a binder such as hydroxypropylcellulose or polyvinyl pyrrolidone; a disintegrator such as calcium carboxymethylcellulose or low-substituted hydroxypropylmethylcellulose; a coating agent such as hydroxypropylmethylcellulose, macrogol or silicone resin; or a film forming agent such as gelatin film.

The dosage of the present compound can be selected suitably according to the symptom, age, dosage form and the like. In case of the oral preparation, the present compound can be administered once to several times per day with a daily dose of 0.1 to 5000 mg, preferably 1 to 1000 mg.

Examples of preparations of intermediates, examples of preparations and formulations of the present compounds and results of pharmacological test are shown below. These examples do not limit the scope of the invention, but are intended to make the invention more clearly understandable.

BEST MODE FOR CARRYING OUT THE INVENTION

[A] Preparation of Intermediates

PREPARATION EXAMPLE 1

2-(1-Adamantyl)-N-pentylethylamine hydrochloride (Intermediate No. 1-1)

Pentylamine (2.69 ml, 23.2 mmol), potassium carbonate (2.14 g, 15.5 mmol) and sodium iodide (2.30 g, 15.3 mmol) were added to a solution of 2-(1-adamantyl)ethyl methanesulfonate (2.07 g, 8.01 mmol) in ethanol (45.8 ml), and the mixture was refluxed for 17 hours. The reaction mixture was concentrated under reduced pressure, and the concentrate was diluted with chloroform (100 ml). This was washed with a 1 N aqueous sodium hydroxide solution (100 ml) and a saturated aqueous sodium chloride solution (100 ml) successively, and the organic layer was dried over magnesium sulfate. The solvent was evaporated under reduced pressure, and the residue was purified by silica gel column chromatography. A 4 N solution of hydrogen chloride in ethyl acetate (3.1 ml) was added to a solution of the resulting free form (1.52 g, 6.10 mmol) of the titled compound in ethyl acetate (0.50 ml). The precipitated solid was washed with ethyl acetate and filtered off to give 1.33 g (60%) of the titled compound.

IR(KBr): 2924, 2850, 2519, 1456 cm$^{-1}$
mp: 263.0-264.5° C.

The following compounds were obtained by a method similar to Preparation Example 1. The titled compounds were not sometimes isolated in the form of hydrochlorides.

N'-[2-(1-Adamantyl)ethyl]-N-(benzyloxycarbonyl)-N-methylethylenediamine (Intermediate No. 1-2)
IR(neat): 2901, 2844, 1704 cm$^{-1}$ 2-(1-Adamantyl)-N-(cyclopentylmethyl)ethylamine hydrochloride (Intermediate No. 1-3)
IR(KBr): 2907, 2847, 1452 cm$^{-1}$
mp: 300.0-310.0° C.

N'-[2-(1-Adamantyl)ethyl]-1-(t-butoxycarbonyl)-N-methylethylenediamine (Intermediate No. 1-4)
IR(neat): 3307, 2902, 2846, 1698 cm$^{-1}$ 2,2'-Di(1-adamantyl)diethylamine hydrochloride (Intermediate No. 1-5)
IR(KBr): 2900, 2845, 2735, 2453 cm$^{-1}$
mp: 325° C.

2-(1-Adamantyl)-N-propylethylamine (Intermediate No. 1-6)
IR(neat): 3276, 2903, 2846, 1450 cm$^{-1}$ N'-[2-(1-Adamantyl)ethyl]-N,N-dimethylethylenediamine dihydrochloride (Intermediate No. 1-7)
IR(KBr): 3424, 2901, 2846, 2445 cm$^{-1}$
mp: 254.5-259.0° C.

2-(1-Adamantyl)-N-cyclopentylethylamine hydrochloride (Intermediate No. 1-8)
IR(KBr): 2910, 2846, 2771, 2450 cm$^{-1}$
mp: 300-312° C.

2-(1-Adamantyl)-N-cyclopropylethylamine (Intermediate No. 1-9)
IR(neat): 3272, 2901, 2845 cm$^{-1}$ 2-(1-Adamantyl)-N-(2-methoxyethyl)ethylamine hydrochloride (Intermediate No. 1-10)
IR(KBr): 2909, 2846, 2792, 1451 cm$^{-1}$
mp: 278.5-281.5° C.

(1-Adamantyl)-N-(2-propynyl)ethylamine (Intermediate No. 1-11)
IR(neat): 2900, 2845, 1450 cm$^{-1}$ N-Pentyl-2-(2-pyridyl)ethylamine (Intermediate No. 1-12)
IR(neat): 3305, 2927, 2857, 1591 cm$^{-1}$ 2-(1-Adamantyl)-N-benzylethylamine hydrochloride (Intermediate No. 1-13)
IR(KBr): 2900, 2846, 2750, 2528, 2468, 2372, 1585 cm$^{-1}$
mp: 264.0-265.0° C.

2-(1-Adamantyl)-N-furfurylethylamine hydrochloride (Intermediate No. 1-14)
IR(KBr): 3456, 2903, 2846, 2741, 2426 cm$^{-1}$
mp: 225.0-233.0° C.

2-(1-Adamantyl)-N-butylethylamine (Intermediate No. 1-15)
IR(neat): 2903, 1683, 1450 cm$^{-1}$ 2-Cyclohexyl-N-(2-thienyl)methylethylamine hydrochloride (Intermediate No. 1-16)

N-Pentylphenethylamine hydrochloride (Intermediate No. 1-17)
IR(KBr): 3028, 2957, 2786, 1456 cm$^{-1}$
mp: 260.0-285.0° C.

2-Cyclohexyl-N-butylethylamine hydrochloride (Intermediate No. 1-18)
IR(KBr): 2921, 2853, 2794, 2739, 2442, 1590, 1484, 1451 cm$^{-1}$
mp: 250° C. or higher 2-Cyclohexyl-N-pentylethylamine hydrochloride (Intermediate No. 1-19)
IR(KBr): 2924, 2793, 1451 cm$^{-1}$
mp: 250° C. or higher N-(t-Butoxycarbonyl)-N'-(2-cyclohexylethyl)-N-methylethylenediamine (Intermediate No. 1-20)
IR(neat): 3350, 2923, 2850, 1697, 1481, 1449 cm$^{-1}$ N'-(2-Cyclohexylethyl)-N,N-dimethylethylenediamine (Intermediate No. 1-21)
IR(neat): 3310, 2921, 2850, 2815, 1448 cm$^{-1}$ N-[2-(1-Adamantyl)ethyl]-3-(4-pyridyl)propylamine (Intermediate No. 1-22)
IR(neat): 3291, 2902, 2845, 1602, 1450 cm$^{-1}$ 2-(1-Adamantyl)-N-isopropylethylamine hydrochloride (Intermediate No. 1-23)
IR(KBr): 2909, 2846, 2754, 2464, 1588, 1476, 1451 cm$^{-1}$
mp: 266.0-269.5° C.

N-(2-Piperidinoethyl)pentylamine (Intermediate No. 1-24)
IR(neat): 2932, 2854, 1466 cm$^{-1}$ 2-(1-Adamantyl)-N-[(2-methylthiazol-4-yl)methyl]ethylamine (Intermediate No. 1-25)
IR(neat): 2901, 2844, 1449 cm$^{-1}$ N-[2-(1-Adamantyl)ethyl]cinnamylamine (Intermediate No. 1-26)
IR(neat): 2901, 2845, 1449 cm$^{-1}$ N-[2-(1-Adamantyl)ethyl]-2-methyl-2-propenylamine (Intermediate No. 1-27)
IR(neat): 2902, 2845, 1450 cm$^{-1}$ N-[2-(1-Adamantyl)ethyl]-3-methyl-2-butenylamine (Intermediate No. 1-28)
IR(neat): 2903, 2846, 1450 cm$^{-1}$ N-[2-(1-Adamantyl)ethyl]decylamine hydrochloride (Intermediate No. 1-29)
IR(KBr): 2926, 2849, 2778, 2469 cm$^{-1}$
mp: 204.0-208.5° C.

N-[2-(1-Adamantyl)ethyl]hexylamine hydrochloride (Intermediate No. 1-30)
IR(KBr): 2909, 2848, 2766, 2446 cm$^{-1}$
mp: 230.0-243.0° C.

2-(1-Adamantyl)-N-(benzyloxy)ethylamine (Intermediate No. 1-31)
IR(neat): 2901, 2846, 1452 cm$^{-1}$ 2-(1-Adamantyl)-N-[(2-thienyl)methyl]ethylamine hydrochloride (Intermediate No. 1-32)
IR(KBr): 2908, 2846, 2757, 2426 cm$^{-1}$
mp: 257.0-260.0° C.

N-[2-(1-Adamantyl)ethyl]-2-butenylamine (Intermediate No. 1-33)
IR(neat): 2901, 1450 cm$^{-1}$ N-[2-(1-Adamantyl)ethyl]allylamine (Intermediate No. 1-34)
IR(neat): 2902, 1450 cm$^{-1}$ N-[2-(1-Adamantyl)ethyl]cyclopropylmethylamine (Intermediate No. 1-35)
IR(neat): 2901, 1450 cm$^{-1}$ N-[2-(1-Adamantyl)ethyl]-3,3,3-triiluoropropylamine hydrochloride (Intermediate No. 1-36)
IR(KBr): 2910, 2849, 2767, 2598, 2457 cm$^{-1}$
mp: 300.0-310.0° C.

1-[2-(1-Adamantyl)ethyl]-2-(t-butoxycarbonyl)hydrazine (Intermediate No. 1-37)
IR(KBr): 3288, 2899, 1705 cm$^{-1}$
mp: 73.5-810° C.

N-(t-Butoxycarbonyl)-N-methyl-N'-phenethylethylenediamine (Intermediate No. 1-38)
IR(neat): 3326, 3025, 2975, 2930, 1694, 1454 cm$^{-1}$ N-(t-Butoxycarbonyl)-N-methyl-N'-pentylethylnediamine (Intermediate No. 1-39)
IR(neat): 2958, 2929, 1694, 1457 cm$^{-1}$ N-(Benzyloxycarbonyl)-N-methyl-1-phenethylethylenediamine (Intermediate No. 1-40)
IR(neat): 3309, 3027, 2936, 2824, 1698, 1454 cm$^{-1}$ N-(Benzyloxycarbonyl)-N-methyl-N'-pentylethylenediamine (Intermediate No. 1-41)
IR(neat): 2928, 2858, 1703, 1455 cm$^{-1}$ 2-Cyclohexyl-N-(2-methoxyethyl)ethylamine hydrochloride (Intermediate No. 1-42)
IR(KBr): 2923, 2855, 2784, 2478, 2444 cm$^{-1}$
mp: 205.0-208.0° C.

N-Ethyl-3,4,5-trimethoxyphenethylamine (Intermediate No. 1-43)
IR(neat): 3300, 2936, 2828, 1588, 1508, 1457, 1419, 1331, 1236, 1126, 1008 cm$^{-1}$ 5-[2-(Isopentylamino)ethyl]imidazole dihydrochloride (Intermediate No. 1-44)
IR(KBr): 2806, 2467, 1619, 1604, 1446, 1347, 1089, 914, 827, 735, 627, 622 cm$^{-1}$
mp: 235.2-238.0° C.

N-Cyclohexyl-3,4-dimethoxyphenethylamine (Intermediate No. 1-45)
IR(neat): 2928, 2852, 1591, 1515, 1463, 1449, 1416, 1261, 1236, 1155, 1139, 1029, 802, 761 cm$^{-1}$
bp: 170° C./210 Pa N-Cyclopropyl-3,4,5-trimethoxyphenethylamine (Intermediate No. 1-46)
IR(neat): 3304, 2932, 2832, 1588, 1505, 1459, 1418, 1332, 1236, 1126, 1009 cm$^{-1}$ N-[2-(1-Adamantyl)ethyl]-N-(t-butoxycarbonyl)-N-methyl-1,3-propanediamine (Intermediate No. 1-47)
IR(neat): 3308, 2902, 2845, 1698, 1480 cm$^{-1}$ N-Cyclohexyl(phenyl)methyl-3-(4-methoxyphenyl)propylamine hydrochloride (Intermediate No. 1-48)
IR(KBr): 2928, 2857, 2765, 1592, 1510, 1455, 1230, 1064, 1033, 817 cm$^{-1}$
mp: 187.5-189.5° C.

N-Diphenylmethyl-3-phenylpropylamine (Intermediate No. 1-49)
IR(neat): 3024, 2931, 1601, 1493, 1452 cm$^{-1}$ N-Pentyl-3-phenylpropylamine hydrochloride (Intermediate No. 1-50)
IR(KBr): 3027, 2955, 2870, 2780, 2492, 2413 cm$^{-1}$
mp: 230.0-238.0° C.

N-Acetyl-N'-[2-(1-adamantyl)ethyl]ethylenediamine hydrochloride (Intermediate No. 1-51)
IR(KBr): 2897, 2845, 2361, 1826, 1707, 1567 m$^{-1}$
mp: 245.0-247.0° C.

N-Isopentyl-3,3,3-trifluoropropylamine hydrochloride (Intermediate No. 1-52)
IR(KBr): 2961, 2800, 1253, 1173 m$^{-1}$
mp: 288° C. or higher N-[2-(1-Adamantyl)ethyl]-2,2,2-trifluoroethylamine hydrochloride (Intermediate No. 1-53)
IR(KBr): 2904, 2849, 1273, 1233, 1176, 1145 m$^{-1}$
mp: 263.0-265.0° C.

3-Cyclohexyl-N-propylpropylamine hydrochloride (Intermediate No. 1-54)
IR(KBr): 2924, 2854, 2779 m 1
mp: 234.6-235.4° C.

N'-[3-(1-Adamantyl)propyl]-N-(t-butoxycarbonyl)-N-methylethylenediamine (Intermediate No. 1-55)

$^1$H-NMR (400 MHz, CDCl$_3$) δ 0.99-1.10 (m, 2H), 1.32-1.52 (m, 17H), 1.55-1.65 (m, 4H), 1.70 (d, J=11.8 Hz, 3H), 1.93 (s, 3H), 2.58 (t, J=7.2 Hz, 2H), 2.77 (br, 2H), 2.91 (s, 3H), 3.33 (br, 2H)

PREPARATION EXAMPLE 2

4-(3-Aminopropyl)pyridine (Intermediate No. 2-1)

N-[3-(4-Pyridyl)propyl]phthalimide (67.1 g, 252 mmol) was mixed with methanol (504 ml) and hydrazine monohydrate (18.3 ml, 378 mmol), and the mixture was refluxed for three hours. The reaction mixture was allowed to stand, then an insoluble matter was filtered out, and the filtrate was concentrated under reduced pressure. Chloroform (1 liter) and a 4 N aqueous sodium hydroxide solution (500 ml) were added to the residue, layers were separated, and the organic layer was dried over sodium sulfate. The organic layer was concentrated under reduced pressure and then distilled under reduced pressure to give 20.5 g (60%) of the titled compound as a colorless oily matter.

IR(neat): 3362, 2933, 1603 cm$^{-1}$
bp: 76.0-79.0° C./40 Pa

The following compounds were obtained by a method similar to Preparation Example 2.

3-(4-Pyridyl)-2-propenylamine (Intermediate No. 2-2)
IR(neat): 3280, 3024, 1599 cm$^{-1}$ 2-(4-Pyridyloxy)ethylamine (Intermediate No. 2-3)
IR(KBr): 3298, 3102, 1610, 1216, 1049 cm$^{-1}$
mp: 108.0-111.5° C.

3-(4-Quinolyl)-2-propenylamine (Intermediate No. 2-4)
IR(neat): 3270, 2944, 1585, 1568, 1508 cm$^{-1}$

PREPARATION EXAMPLE 3

2-(1-Adamantyl)-N-methylethylamine (Intermediate No. 3-1)

A solution of 1-adamantaneacetic acid N-methylamide (1.54 g, 7.45 mmol) in tetrahydrofuran (15.0 ml) was added dropwise to a solution of lithium aluminum hydride (569 mg, 15.0 mmol) in diethyl ether (34.0 ml) under ice-cooling over five minutes. The mixture was refluxed for six hours and then stirred under ice-cooling again. Ethyl acetate was added to the reaction mixture to treat excess lithium aluminum hydride, and then the whole was extracted with 1 N hydrochloric acid (50 ml) twice. A 4 N aqueous sodium hydroxide solution was added to the extract to basify it, and the whole was extracted with diethyl ether (80 ml). The organic layer was washed with a saturated aqueous sodium chloride solution (60 ml) and dried over magnesium sulfate. The solvent was evaporated under reduced pressure to give 890 mg (66%) of the titled compound.

IR(neat): 2902, 2845, 1449 cm$^{-1}$

The following compounds were obtained by a method similar to Preparation Example 3. The compounds could also be converted into corresponding hydrochlorides with a 4 N solution of hydrogen chloride in ethyl acetate.

2-(1-Adamantyl)-N-ethylethylamine hydrochloride (Intermediate No. 3-2)
IR(KBr): 2896, 2847, 2753, 2468, 1610 cm$^{-1}$
mp: 230-245° C.

N-Methyl-3-(4-pyridyl)propylamine (Intermediate No. 3-3)
IR(neat): 3292, 2934, 1602 cm$^{-1}$ 1-Adamantyl-N-propylmethylamine hydrochloride (Intermediate No. 3-4)
IR(KBr): 2905, 1584, 1451 cm$^{-1}$
mp: 340° C.

2-(1-Adamantyl)-N-methylethylamine hydrochloride (Intermediate No. 3-5)
IR(KBr): 3422, 2900, 2846, 2676, 2450, 1630 cm$^{-1}$
mp: 200-220° C.

3-(1-Adamantyl)-N-propylpropylamine hydrochloride (Intermediate No. 3-6)
IR(KBr): 2899, 2467, 1449 cm$^{-1}$
mp: 159.5-162.0° C.

1-Adamantyl-N-pentylmethylamine hydrochloride (Intermediate No. 3-7)
IR(KBr): 2916, 2603, 2509, 2418, 1477 cm$^{-1}$
mp: 170-235° C.

N-[3-(1-Adamantyl)propyl]pentylamine hydrochloride (Intermediate No. 3-8)
IR(KBr): 2901, 2847, 1466, 1453 cm$^{-1}$
mp: 199-224° C.

N-[2-(1-Adamantyl)ethyl]-4,4,4-trifluorobutylamine hydrochloride (Intermediate No. 3-9)
IR(KBr): 3422, 2908, 2852, 2770, 2518, 1452, 1255, 1148 cm$^{-1}$
mp: 243-274° C.

N-[2-(1-Adamantyl)ethyl]-5,5,5-trifluoropentylamine (Intermediate No. 3-10)
IR(neat): 2903, 2846, 1450, 1255, 1142 cm$^{-1}$ N-[3-(1-Adamantyl)propyl]butylamine hydrochloride (Intermediate No. 3-11)
IR(KBr): 2904, 2847, 2756, 1453 cm$^{-1}$
mp: 275.0-276.8° C.

3-(1-Adamantyl)-N-(2,2,2-trifluoroethyl)propylamine hydrochloride (Intermediate No. 3-12)
IR(KBr): 2902, 2850, 2739, 1274, 1258, 1176, 1139 cm$^{-1}$
mp: 262.0-268.0° C.

4-(1-Adamantyl)-N-ethylbutylamine hydrochloride (Intermediate No. 3-13)
IR(KBr): 2901, 2847, 2457, 1451 cm$^{-1}$
mp: 224-230° C.

4-(1-Adamantyl)-N-propylbutylamine hydrochloride (Intermediate No. 3-14)
IR(KBr): 2899, 2848, 2751, 2410, 1451 cm$^{-1}$
mp: 234-249° C.

N-(1-Adamantyl)-N'-propylethylenediamine dihydrochloride (Intermediate No. 3-15)
IR(KBr): 2927, 2719, 2508, 2429, 1471 cm$^{-1}$
mp: 288.5-289.5° C.

PREPARATION EXAMPLE 4 t-Butyl 3-[N-[2-(1-adamantyl)ethyl]amino]propionate hydrochloride (Intermediate No. 4-1)

2-(1-Adamantyl)ethylamine hydrochloride (1.0 g, 4.6 mmol) was dissolved in ethanol (10 ml), and triethylamine (0.65 ml, 4.6 mmol) and t-butyl acrylate (0.75 ml, 5.1 mmol) were added to the solution under ice-cooling. Then, the temperature was raised to room temperature, and the mixture was stirred overnight. The reaction mixture was concentrated under reduced pressure, a 1 N aqueous sodium hydroxide solution (30 ml) and ethyl acetate (50 ml) were added to the residue, and layers were separated. The ethyl acetate layer was washed with water (50 ml) and a saturated aqueous sodium chloride solution (50 ml) successively and dried over anhydrous magnesium sulfate. The ethyl acetate layer was concentrated under reduced pressure, and the concentrate was purified by silica gel column chromatography. The resulting oily matter (0.50 g, 1.6 mmol) was dissolved in diethyl ether (20 ml), and a 4 N solution of hydrogen chloride in ethyl acetate (1.0 ml, 4.0 mmol) was added thereto to precipitate a solid. This solid was filtered off with diethyl ether to give 0.33 g (23%) of the titled compound.

IR(KBr): 2902, 2846, 1733, 1166 cm$^{-1}$ mp: 210° C.

The following compounds were obtained by a method similar to Preparation Example 4. The titled compounds were not sometimes isolated in the form of hydrochlorides.

Methyl 3-[N-(2-cyclohexylethyl)amino]propionate hydrochloride (Intermediate No. 4-2)

IR(KBr): 2924, 2853, 2792, 1736, 1455, 1439 cm$^{-1}$ mp: 185.0-187.5° C.

t-Butyl 3-[N-(2-cyclohexylethyl)amino]propionate (Intermediate No. 4-3)

IR(neat): 2977, 2922, 2850, 1728, 1449 cm$^{-1}$ t-Butyl 3-[N-[3-(4-pyridyl)propyl]amino]propionate hydrochloride (Intermediate No. 4-4)

IR(neat): 3322, 2977, 2933, 1724, 1602, 1367, 1153 cm$^{-1}$

PRODUCTION EXAMPLE 5

5-(4-Pyridyl)valeric acid (Intermediate No. 5-1)

N,N-Dimethylformamide (17 ml) was added to a mixture of (benzyloxycarbonylmethyl)triphenylphosphonium bromide (4.60 g, 9.36 mmol) and β-(4-pyridyl)acrolein oxalate (1.90 g, 8.51 mmol), and the whole was stirred under ice-cooling. Potassium carbonate (4.70 g, 34.0 mmol) was added thereto, and the temperature was raised to room temperature. The whole was stirred overnight, then diluted with ethyl acetate (100 ml) and washed with water (100 ml) twice and saturated brine (50 ml) successively. The organic layer was dried over sodium sulfate, and ethyl acetate was evaporated under reduced pressure. The residue was purified by silica gel column chromatography to give 2.29 g (quantitatively) of 5-(4-pyridyl)valeric acid-2,4-diene benzyl ester as a pale yellow oily matter.

Next, methanol (42 ml) and acetic acid (1.0 ml, 18 mmol) were added to 5-(4-pyridyl)valeric acid-2,4-diene benzyl ester (2.25 g, 8.48 mmol), and a nitrogen gas was bubbled through the mixture for ten minutes. Palladium hydroxide on carbon (catalytic amount) was added to the mixture, and the whole was stirred under a hydrogen atmosphere at room temperature overnight. An insoluble matter was filtered out by Celite filtration, and the filtrate was concentrated under reduced pressure. Ethyl acetate (50 ml) was added to the solidified residue, and the mixture was stirred at room temperature for three hours. Crystals were filtered off to give 1.00 g (66%) of the titled compound as pale yellow crystals.

IR(KBr): 2943, 1719, 1636, 1605 cm$^{-1}$ mp: 155.0-180.0° C.

PREPARATION EXAMPLE 6

3-[N-(2-Cyclohexylethyl)amino]propionamide hydrochloride (Intermediate No. 6-1)

Trifluoroacetic acid (6 ml) was added to t-butyl 3-[N-(2-cyclohexylethyl)amino]propionate (Intermediate No. 4-3, 2.0 g, 7.8 mmol) under ice-cooling. The mixture was stirred overnight, and then concentrated under reduced pressure. A 4 N solution of hydrogen chloride in ethyl acetate was added to the residue, and the whole was concentrated under reduced pressure, and then the resulting crystals were filtered off with diethyl ether to give 1.5 g (96%) of 3-[N-(2-cyclohexylethyl) amino]propionic acid hydrochloride.

Next, tetrahydrofuran (8 ml) was added to 3-[N-(2-cyclohexylethyl)amino]propionic acid hydrochloride (1.0 g, 4.2 mmol), and the mixture was stirred at room temperature. Di-t-butyl carbonate (1.1 g, 5.1 mmol) and triethylamine (1.3 ml, 9.3 mmol) were added to the mixture, the whole was stirred overnight, and then a 5% aqueous citric acid solution (10 ml) was added to the reaction mixture. The whole was extracted with chloroform (60 ml), and the organic layer was washed with saturated brine (20 ml). The organic layer was dried over magnesium sulfate and concentrated under reduced pressure. The residue was purified by silica gel column chromatography to give 0.79 g (62%) of 3-[N-(t-butoxycarbonyl)-N-(2-cyclohexylethyl)amino]propionic acid as a colorless oily matter.

Next, anhydrous tetrahydrofuran (7 ml) was added to 3-[N-(t-butoxycarbonyl)-N-(2-cyclohexylethyl)amino]propionic acid (0.59 g, 2.0 mmol), and the mixture was stirred at −78° C. N-Methylmorpholine (0.22 ml, 2.0 mmol) and then a solution of isobutyl chloroformate (0.38 ml, 2.9 mmol) in tetrahydrofuran (3 ml) were added to the mixture. After one hour, a 28% aqueous ammonia solution (6.0 ml, 9.8 mmol) was added thereto, and the whole was stirred for 1.5 hours. Chloroform (50 ml) was added to the reaction mixture, the temperature was raised to room temperature, and the whole was washed with a saturated aqueous sodium hydrogencarbonate solution (20 ml) and saturated brine (20 ml) successively. The organic layer was dried over magnesium sulfate and concentrated under reduced pressure, and the residue was purified by silica gel column chromatography to give 0.34 g (58%) of 3-[N-(t-butoxycarbonyl)-N-(2-cyclohexylethyl)amino]propionamide as colorless crystals.

Next, a 4 N solution of hydrogen chloride in 1,4-dioxane (3.1 ml) was added to 3-[N-(t-butoxycarbonyl)-N-(2-cyclohexylethyl)amino]propionamide (0.37 g, 1.2 mmol), and the mixture was stirred at room temperature overnight. The reaction mixture was concentrated under reduced pressure, diisopropyl ether was added to the resulting solid, and the solid was filtered off to give 0.30 g (quantitatively) of the titled compound as colorless crystals.

IR(KBr): 3386, 3196, 2921, 2852, 2808, 1705, 1656, 1452 cm$^{-1}$ mp: 165.0° C.

PREPARATION EXAMPLE 7

Di-5-hexenylamine (Intermediate No. 7-1)

N,N-Dimethylformamide (28 ml) was added to 3-aminopropionitrile (0.98 g, 14 mmol), and the mixture was stirred at room temperature. 6-Bromo-1-hexene (5.0 g, 31 mmol), sodium iodide (11 g, 73 mmol) and potassium carbonate (5.8 g, 42 mmol) were added to the mixture, and the whole was stirred overnight. The reaction mixture was diluted with diethyl ether (100 ml), and the whole was washed with water (100 ml, twice) and saturated brine (50 ml) successively. The organic layer was dried over sodium sulfate and concentrated under reduced pressure. The residue was purified by silica gel column chromatography to give 2.2 g (66%) of 3-(di-5-hexenyl)aminopropionitrile as a colorless oily matter.

Next, ethanol (8.6 ml) and potassium hydroxide (0.85 g, 13 mmol) were added to 3-(di-5-hexenyl)aminopropionitrile (2.0 g, 8.6 mmol), and the mixture was refluxed for 7.5 hours. The reaction mixture was allowed to stand, and then water (150 ml) and chloroform (150 ml) were added to the reaction mixture. Layers were separated, and the organic layer was dried over sodium sulfate. The organic layer was concentrated under reduced pressure, and the residue was purified by basic silica gel column chromatography to give 0.32 g (21%) of the titled compound as a pale yellow oily matter.

IR(neat): 3076, 2976, 2928, 2856, 1679, 1640 cm$^{-1}$

The following compound was obtained by a method similar to Preparation Example 7.

Di-7-octenylamine (Intermediate No. 7-2)
IR(neat): 3075, 2976, 2926, 2854, 1640 cm$^{-1}$

PREPARATION EXAMPLE 8

N-[2-(1-Adamantyloxy)ethyl]propylamine hydrochloride (Intermediate No. 8-1)

2-(Propylamino)ethanol (2.4 g, 23 mmol) was mixed with 1-bromoadamantane (0.50 g, 2.3 mmol) and triethylamine (0.32 ml, 2.3 mmol), and the mixture was stirred at an external temperature of 100° C. for two hours, at 130° C. for five hours and at 150° C. for three hours. The reaction mixture was allowed to stand, then ethyl acetate (50 ml) was added to the reaction mixture, and the whole was washed with water (50 ml) twice and saturated brine (30 ml) successively. The organic layer was dried over sodium sulfate and concentrated under reduced pressure. The residue was purified by silica gel column chromatography, a 4 N solution of hydrogen chloride in ethyl acetate (2 ml) was added to the separated substance, and the whole was concentrated under reduced pressure. The resulting crystals were filtered off with ethyl acetate to give 0.16 g (25%) of the titled compound as colorless crystals.

IR(KBr): 3544, 2907, 2502, 1584 cm$^{-1}$
mp: 232.0-232.7° C.

PREPARATION EXAMPLE 9

2-Propylaminoacetic acid N-(1-adamantyl)amide (Intermediate No. 9-1)

Ethanol (36 ml) was added to bromoacetic acid (5.00 g, 36.0 mmol), and the mixture was stirred under ice-cold water-cooling. Propylamine (14.8 ml, 180 mmol) was added to the mixture over one minute, and then the whole was stirred at an external temperature of 80° C. for 2.5 hours. A 4 N aqueous sodium hydroxide solution (27 ml) was added thereto, and the whole was concentrated under reduced pressure. Then, water (27 ml) and tetrahydrofuran (30 ml) were added to the concentrate, and the mixture was stirred at room temperature. A solution of di-t-butyl carbonate (9.43 g, 43.2 mmol) in tetrahydrofuran (6 ml) was added to the mixture, and after 15 minutes, citric acid monohydrate was added to the reaction mixture to acidify it weakly. The whole was extracted with ethyl acetate (150 ml), and the organic layer was washed with water (100 ml) and saturated brine (50 ml) successively. The organic layer was dried over sodium sulfate and concentrated under reduced pressure. The residue was purified by silica gel column chromatography to give 5.06 g (65%) of 2-[N-(t-butoxycarbonyl)-N-propylamino]acetic acid as a colorless solid.

Next, methylene chloride (208 ml) was added to a mixture of 2-[N-(t-butoxycarbonyl)-N-propylamino]acetic acid (4.52 g, 20.8 mmol) and 1-adamantaneamine (3.46 g, 22.9 mmol), and the whole was stirred at room temperature. N,N-Diisopropylethylamine (7.25 ml, 41.6 mmol) and then O-(7-azabenzotriazol-1-yl)-N,N',N'-tetramethyluronium hexafluorophosphate (8.71 g, 22.9 mmol) were added thereto, and the whole was stirred overnight. The reaction mixture was concentrated under reduced pressure, and the residue was purified by silica gel column chromatography to give 7.88 g (quantitatively) of 2-[N'-(butoxycarbonyl)-N'-propylamino]acetic acid N-(1-adamantyl)amide as a colorless oily matter. The obtained oily matter solidified at room temperature.

Next, a 4 N solution of hydrogen chloride in ethyl acetate (55 ml, 0.22 mol) was added to 2-[N'-(t-butoxycarbonyl)-N-propylamino]acetic acid N-(1-adamantyl)amide (7.68 g, 21.9 mmol), and the mixture was stirred at room temperature for one hour. The resulting crystals were filtered off with ethyl acetate and washed with ethyl acetate to give 5.97 g (95%) of the titled compound as colorless crystals.

IR(KBr): 3272, 2906, 2848, 2589, 1676, 1562 cm$^{-1}$
mp: 278.0-279.2° C.

PREPARATION EXAMPLE 10

N-(t-Butoxycarbonyl)-2-(4-pyridyloxy)ethylamine (Intermediate No. 10-1)

Di-t-butyl dicarbonate (380 mg, 1.74 mmol) and triethylamine (240 μl, 1.74 mmol) were added to a solution of the Intermediate No. 2-4 (200 mg, 1.45 mmol) in tetrahydrofutan (5 ml) under ice-cooling, the temperature was raised to room temperature, and the mixture was stirred for 25 minutes. The solvent was evaporated under reduced pressure from the reaction mixture, and the residue was distributed with ethyl acetate (50 ml) and a saturated aqueous sodium hydrogencarbonate solution (50 ml). The aqueous layer was further extracted with chloroform (50 ml), and the combined organic layer was dried over anhydrous magnesium sulfate. The solvent was evaporated under reduced pressure, and the resulting residue was purified by silica gel column chromatography to give 70 mg (20.2%) of the titled compound.

IR(neat): 3230, 2976, 1706, 1596 cm$^{-1}$

PREPARATION EXAMPLE 11

(RS)-2-Methyl-3-(4-pyridyl)propylamine (Intermediate No. 11-1)

N,N-Dimethylformamide (143 ml) was added to sodium hydride (5.36 g, 134 mmol) under a nitrogen atmosphere, and the mixture was stirred under ice-cooling. A solution of diethyl methylmalonate (11.7 g, 67.1 mmol) in N,N-dimethylformamide (40 ml) was added dropwise to the mixture over five minutes, after ten minutes, 4-chloropicolyl hydrochloride (10.0 g, 61.0 mmol) was added thereto little by little over five minutes, and the temperature was raised to room temperature. After one hour, a saturated aqueous sodium hydrogencarbonate solution (500 ml) was added to the reaction mixture, and the whole was extracted with diethyl ether (400 ml). The organic layer was washed with water (100 ml) and saturated brine (50 ml) and dried over magnesium sulfate. The organic layer was concentrated under reduced pressure to give 17.2 g (quantitatively, containing sodium hydride oil) of diethyl 2-methyl-2-(4-pyridylmethyl)malonate as a brown oily matter.

Next, 6 N hydrochloric acid (96.8 ml, 581 mmol) was added to diethyl 2-methyl-2-(4-pyridylmethyl)malonate (17.2 g, 64.6 mmol), and the mixture was refluxed overnight. The reaction mixture was allowed to stand, then washed with hexane (100 ml) to remove sodium hydride oil contained in diethyl 2-methyl-2-(4-pyridylmethyl)malonate, and concentrated under reduced pressure. The resulting crystals were filtered off with ethyl acetate to give 10.7 g (82%) of 2-methyl-3-(4-pyridyl)propionic acid as pale pink crystals.

Next, chloroform (8 ml), thionyl chloride (2.2 ml, 30.6 mmol) and N,N-dimethylformamide (one drop) were added to 2-methyl-3-(4-pyridyl)propionic acid (1.69 g, 10.2 mmol), and the mixture was refluxed with stirring for one hour. The reaction mixture was concentrated under reduced pressure, chloroform (8 ml) was added to the concentrate, and the mixture was added slowly to a 28% aqueous ammonia solution stirred under ice-cooling. After ten minutes, the temperature was raised to room temperature, and the whole was stirred overnight. The reaction mixture was concentrated under reduced pressure, ethyl acetate (100 ml) was added to the concentrate, and the resulting insoluble matter was filtered out. The filtrate was concentrated under reduced pressure, the residue was purified by silica gel column chromatography, and the resulting crystals were filtered off with diethyl ether to give 0.72 g (43%) of 2-methyl-3-(4-pyridyl) propionamide as pale yellow crystals.

Next, anhydrous diethyl ether (20 ml) was added to lithium aluminum hydride (0.45 g, 12 mmol) under a nitrogen atmosphere, and the mixture was stirred under ice-cooling. A solution of 2-methyl-3-(4-pyridyl)propionamide (0.68 g, 4.1 mmol) in anhydrous methylene chloride (20 ml) was added dropwise to the mixture over five minutes, the temperature was raised to room temperature, and the whole was stirred overnight. The reaction mixture was cooled with ice again, ethyl acetate (5 ml) was added slowly to the reaction mixture, and then a 1 N aqueous sodium hydroxide solution was added thereto first slowly (total 100 ml). The whole was extracted with chloroform (100 ml), and the organic layer was dried over sodium sulfate and concentrated under reduced pressure to give 0.56 g (90%) of the titled compound as a pale yellow oily matter.

IR(neat): 3293, 2957, 2925, 1602 $cm^{-1}$

The following compounds were obtained by a method similar to Preparation Example 11. Optically active substances could be obtained by optical resolution with an optically active acid.

2-(4-Pyridylmethyl)butylamine (Intermediate No. 11-2)
IR(neat): 3296, 3025, 2960, 2874, 1602 $cm^{-1}$ 2-Benzyl-3-(4-pyridyl)propylamine (Intermediate No. 11-3)
IR(neat): 3296, 3062, 3025, 1602 $cm^{-1}$ 2,2-Bis(4-pyridylmethyl)ethylamine (Intermediate No. 11-4)
IR(neat): 3290, 3026, 2924, 1602, 1557 $cm^{-1}$ (−)-2-Methyl-3-(4-pyridyl)propylamine (Intermediate No. 11-5)
IR(neat): 3362, 3301, 2958, 1603 $cm^{-1}$
$[\alpha]^{20}_D$: 10.6° (MeOH, C 1.0)

(+)-2-Methyl-3-(4-pyridyl)propylamine (Intermediate No. 11-6)
IR(neat): 3362, 3294, 2958, 1603 $cm^{-1}$
$[\alpha]^{20}_D$: +9.9° (MeOH, C 1.0)

PREPARATION EXAMPLE 12

3-(4-Quinolyl)propylamine (Intermediate No. 12-1)

A catalytic amount of 10% palladium on carbon was added to a solution of 3-(4-quinolyl)-2-propenylamine (Intermediate No. 2-4) (188 mg, 1.02 mmol) obtained in Preparation Example 2 in methanol (3 ml) at room temperature under a nitrogen atmosphere, and the mixture was stirred under a hydrogen atmosphere overnight. The reaction mixture was filtered with Celite, the solvent was evaporated under reduced pressure, and the resulting residue was distributed with ethyl acetate (30 ml) and a saturated aqueous ammonium chloride solution (30 ml). A 4 N aqueous sodium hydroxide solution (30 ml) was added to the aqueous layer, the whole was extracted with chloroform (100 ml), and the obtained organic layer was dried over anhydrous magnesium sulfate. The solvent was evaporated under reduced pressure to give 145 mg (76.3%) of the titled compound.

IR(neat): 3350, 2938, 1591, 1510 $cm^{-1}$

PREPARATION EXAMPLE 13

3-(4-Pyridyl)butylamine (Intermediate No. 13-1)

N,N-Dimethylformamide (33 ml) was added to a mixture of 4-acetylpyridine (2.00 g, 16.5 mmol) and (benzyloxycarbonyl)methyltriphenylphosphonium bromide (8.94 g, 18.2 mmol), and the whole was stirred under ice-cooling. Potassium carbonate (9.12 g, 66.0 mmol) was added thereto, the external temperature was raised to 70° C., and the whole was stirred overnight. The reaction mixture was diluted with diethyl ether (100 ml), and the whole was washed with water (100 ml, twice) and saturated brine (50 ml) successively. The organic layer was dried over magnesium sulfate and concentrated under reduced pressure. The residue was purified by silica gel column chromatography to give 1.77 g (42%: mixture of E form and Z form) of benzyl 3-(4-pyridyl)-2-butenoate as a pale yellow oily matter.

Next, methanol (31 ml) and acetic acid (0.71 ml, 12.4 mmol) were added to benzyl 3-(4-pyridyl)-2-butenoate (1.75 g, 6.20 mmol), and a nitrogen gas was bubbled through the mixture at room temperature for 10 minutes. A catalytic amount of 10% palladium on carbon was added to the mixture, and the whole was stirred under a hydrogen atmosphere at room temperature overnight. An insoluble matter was filtered out, and the filtrate was concentrated under reduced pressure. The resulting crystals were filtered off with acetone to give 0.61 g (60%) of 3-(4-pyridyl)butyric acid as pale yellow crystals.

Next, chloroform (5 ml), thionyl chloride (0.80 ml, 11 mmol) and N,N-dimethylformamide (one drop) were added to 3-(4-pyridyl)butyric acid (0.60 g, 3.6 mmol), and the mixture was refluxed with stirring for one hour. The reaction mixture was concentrated under reduced pressure, chloroform (5 ml) was added to the concentrate, and the whole was added slowly to a saturated ammonia/tetrahydrofuran solution (5 ml) stirred under ice-cooling. After 2.5 hours, an insoluble matter was filtered out, and the filtrate was concentrated under reduced pressure. The residue was purified by silica gel column chromatography to give 0.34 g of a mixture of 3-(4-pyridyl)butyramide and its olefin oxide as pale yellow crystals.

Next, anhydrous ether (8 ml) was added to lithium aluminum hydride (0.16 g, 4.2 mmol) under a nitrogen atmosphere, and the mixture was stirred under ice-cooling. A solution of 3-(4-pyridyl)butyramide (0.22 g, 1.4 mmol) in anhydrous methylene chloride (8 ml) was added dropwise to the mixture over two minutes, the temperature was raised to room temperature, and the whole was stirred overnight. Ethyl acetate (1 ml) and a 1 N aqueous sodium hydroxide solution (20 ml) were added to the reaction mixture, and the whole was extracted with chloroform (50 ml). The organic layer was dried over anhydrous sodium sulfate and concentrated under reduced pressure. The residue was purified by silica gel column chromatography to give 0.15° g (75%) of the titled compound as a pale yellow oily matter.

IR(neat): 3350, 2963, 2873, 1601 $cm^{-1}$

PREPARATION EXAMPLE 14

N-(4-Pyridyl)ethylenediamine (Intermediate No. 14-1)

Ethylenediamine (10.4 ml, 155 mmol) was added to 4-bromopyridine hydrochloride (3.00 g, 15.5 mmol) under a nitrogen atmosphere, and the mixture was refluxed for 1.5 hours. The temperature was cooled to room temperature, potassium carbonate (8.57 g, 62.0 mmol) was added to the reaction mixture, and the whole was stirred for 10 minutes. Then, the solid was filtered out and washed with toluene and 2-propanol successively. The filtrate was concentrated under reduced pressure, the residue was purified by basic silica gel column chromatography, and the resulting solid was filtered off with diisopropyl ether to give 1.63 g (77%) of the titled compound as a pale-yellow solid.

IR(KBr): 3320, 3240, 3028, 2930, 1615 cm$^{-1}$
mp: 114.0-116.5° C.

PREPARATION EXAMPLE 15

4-(3-Aminobutyl)pyridine (Intermediate No. 15-1)

Anhydrous N,N-dimethylformamide (41 ml) was added to sodium hydride (2.81 g, 70.3 mmol) under a nitrogen atmosphere, and the mixture was stirred under ice-cold water-cooling. A solution of t-butyl acetoacetate (6.33 g, 40.0 mmol) in N,N-dimethylformamide (20 ml) was added dropwise to the mixture over 10 minutes, after 10 minutes, 4-(chloromethyl)pyridine hydrochloride (5.00 g, 30.5 mmol) was added thereto little by little under a nitrogen stream over three minutes, and the temperature was raised to room temperature. After two hours, a saturated aqueous sodium hydrogencarbonate solution (150 ml) was added to the reaction mixture, and the whole was extracted with ethyl acetate (100 ml). The organic layer was washed with water (100 ml) and saturated brine (50 ml) successively and dried over anhydrous sodium sulfate. The organic layer was concentrated under reduced pressure, and the residue was purified by silica gel column chromatography to give 1.34 g (18%) of ethyl 2-acetyl-3-(4-pyridyl)propionate as a pale yellow oily matter.

Next, 6 N hydrochloric acid (8 ml) was added to ethyl 2-acetyl-3-(4-pyridyl)propionate (1.20 g, 4.81 mmol), and the mixture was refluxed for 1.5 hours. The reaction mixture was concentrated under reduced pressure, 2-propanol (10 ml) was added to the concentrate, and the whole was concentrated under reduced pressure again. Ethyl acetate was added to the resulting solid, and the solid was filtered off to give 0.79 g (89%) of 4-(4-pyridyl)-2-butanone as a pale yellow solid.

Next, water (12 ml) and tetrahydrofuran (1.2 ml) were added to 4-(4-pyridyl)-2-butanone (736 mg, 3.96 mmol), and the mixture was stirred at room temperature. Sodium carbonate (483 mg, 4.56 mmol) and hydroxylamine hydrochloride (358 mg, 5.15 mmol) were added to the mixture, and the whole was stirred for 1.5 hours and then diluted with ethyl acetate (50 ml). Sodium hydrogencarbonate was added thereto, layers were separated, and the organic layer was washed with saturated brine (10 ml). The organic layer was dried over anhydrous sodium sulfate and concentrated under reduced pressure. Cyclohexane was added to the resulting crystals, and the crystals were filtered off to give 584 mg (90%) of 4-(4-pyridyl)-2-butanoneoxime as pale yellow crystals.

Next, anhydrous ether (19 ml) was added to lithium aluminum hydride (257 mg, 6.77 mmol) under a nitrogen atmosphere, and the mixture was stirred under ice-cooling. A solution of 4-(4-pyridyl)-2-butanoneoxime (556 mg, 3.38 mmol) in ether (15 ml) was added dropwise to the mixture over seven minutes, then the temperature was raised to room temperature, and the whole was refluxed overnight. Further, the whole was refluxed for two days and then stirred under ice-cooling. Ethyl acetate was added slowly to the reaction mixture, and then a 1 N aqueous sodium hydroxide solution was added thereto (first slowly, total 20 ml). Chloroform (80 ml) was added thereto, and an insoluble matter was filtered out with Celite. Layers were separated, and the chloroform layer was concentrated under reduced pressure. The residue was combined with the aqueous layer, tetrahydrofuran (20 ml) was added thereto, and the whole was stirred at room temperature. Di-t-butyl carbonate (1.48 g, 6.78 mmol) was added thereto, and the whole was stirred overnight. The whole was extracted with chloroform (50 ml), and the organic layer was dried over anhydrous magnesium sulfate and concentrated under reduced pressure. The residue was purified by silica gel column chromatography. A 4 N solution of hydrogen chloride in ethyl acetate (3 ml) and ethanol (1 ml) were added to the residue, and the mixture was stirred at room temperature. After three hours, the reaction mixture was concentrated under reduced pressure. Chloroform (5 ml), methanol (5 ml) and triethylamine (1 ml) were added to the residue, and the mixture was concentrated under reduced pressure. The residue was purified by basic silica gel column chromatography to give 161 mg (32%) of the titled compound as a brown oily matter.

IR(neat): 3354, 3280, 2958, 2925, 2866, 1602 cm$^{-1}$

The following compounds were obtained by a method similar to Preparation Example 15.

1,2-Dimethyl-3-(4-pyridyl)propylamine (Intermediate No. 15-2)

IR(neat): 3360, 3287, 2963, 2930, 2876, 1602 cm$^{-1}$

1-Ethyl-3-(4-pyridyl)propylamine (Intermediate No. 15-3)

IR(neat): 3357, 2963, 2934, 2875, 1605 cm$^{-1}$

PREPARATION EXAMPLE 16

2,2-Dimethyl-3-(4-pyridyl)propylamine (Intermediate No. 16-1)

A solution of diisopropylamine (10.0 ml, 71.5 mmol) in tetrahydrofuran (150 ml) was cooled to −78° C. under a nitrogen atmosphere, and a 1.6 N solution of butyllithium in hexane was added dropwise thereto over 10 minutes. The mixture was cooled with ice-cold water for 20 minutes and then cooled to −78° C. again, and isobutyronitrile (3.03 ml, 33.3 mmol) was added dropwise to the mixture over five minutes. Further, 4-pyridinecarboxyaldehyde (3.18 ml, 33.3 mmol) was added dropwise thereto over five minutes, and the whole was stirred for one hour 20 minutes. Water (100 ml) was added to the reaction mixture, and the whole was extracted with ethyl acetate (200 ml) by using a continuous extracting apparatus for three days. The obtained organic layer was dried over anhydrous magnesium sulfate and concentrated under reduced pressure. The resulting solid was filtered off with diethyl ether to give 4.20 g (71.6%) of 3-hydroxy-2,2-dimethyl-3-(4-pyridyl)propionitrile as a colorless solid.

Triethylamine (1.57 ml, 11.3 mmol) was added to a solution of 3-hydroxy-2,2-dimethyl-3-(4-pyridyl)propionitrile (1.00 g, 5.67 mmol) in dichloromethane (20 ml) at room temperature. Further, p-toluenesulfonyl chloride (1.30 g, 6.80 mmol) was added to the mixture, and the whole was warmed at 50° C. with stirring for three days. The reaction mixture was allowed to stand and then concentrated under reduced pressure, and the concentrate was purified by silica gel column chromatography to give 699 mg (37.4%) of 2,2-dimethyl-3-(4-pyridyl)-3-(p-tolylsulfonyloxy)propionitrile as a pale yellow solid.

Anhydrous diethyl ether (10 ml) was dropwise to lithium aluminum hydride (345 mg, 9.10 mmol) under a nitrogen atmosphere and ice-cold water-cooling. Then, a solution of 2,2-dimethyl-3-(4-pyridyl)-3-(p-tolylsulfonyloxy)propionitrile (600 mg, 1.82 mmol) in tetrahydrofuran (10 ml) was added dropwise to the mixture. The whole was stirred at room temperature overnight, and water (324 μl), a 15% aqueous sodium hydroxide solution (324 μl) and water (972 μl) were added successively to the reaction mixture while stirring it vigorously under ice-cold water-cooling. The organic layer was dried over anhydrous magnesium sulfate and concentrated under reduced pressure, and the concentrate was purified by silica gel column chromatography to give the titled compound (83.0 mg, 0.505 mmol, 28%) as a pale yellow oily matter.

IR(neat): 3290, 3074, 2960, 1652, 1602, 1417 cm$^{-1}$

PREPARATION EXAMPLE 17

(RS-2-Methyl-3-(4-pyridyl)propanol (Intermediate No. 17-1)

2-Methyl-3-(4-pyridyl)propionic acid (136 g, 0.676 mol) obtained by the synthetic process of Preparation Example 11 was dissolved in tetrahydrofuran (1500 ml), and sodium borohydride (56.2 g, 1.49 mol) was added to the solution under ice-cold water-cooling. After 30 minutes, a mixed liquid of iodine (85.8 g, 0.338 mol) and tetrahydrofuran (500 ml) was added dropwise to the mixture under ice-cold water-cooling, and the temperature was raised to room temperature. After two hours, the reaction mixture was cooled with ice-cold water, and a saturated aqueous sodium hydrogencarbonate solution (100 ml) was added dropwise to the reaction mixture. A saturated aqueous sodium chloride solution (900 ml) and water (400 ml) were added thereto, and the whole was extracted with chloroform (1 liter×2). The organic layer was washed with a 0.01% aqueous sodium thiosulfate solution (1 liter) and a saturated aqueous sodium chloride solution (500 ml) successively, dried over anhydrous magnesium sulfate and concentrated under reduced pressure to give 127.1 g (quantitatively) of the titled compound as a yellow oily matter.

IR(neat): 3292, 2928, 1606, 1558, 1419 cm$^{-1}$

PREPARATION EXAMPLE 18

3-(t-Butyldiphenylsilyloxy)-3-(4-pyridyl)propylamine (Intermediate No. 18-1)

Diisopropylamine (1.98 g, 19.6 mmol) was added dropwise to a solution of a butyllithium/hexane solution (10.5 ml, 16.8 mmol) in anhydrous tetrahydrofuran (20 ml) at −80° C. over five minutes, the temperature was raised to 0° C., and the mixture was stirred for 30 minutes. The mixture was cooled to −80° C. again, then acetonitrile (573 mg, 14.0 mmol) was added dropwise to the mixture over seven minutes, and after 20 minutes, 4-pyridinecarboxyaldehyde (758 mg, 7.08 mmol) was added dropwise thereto over 10 minutes. After 50 minutes, a saturated aqueous ammonium chloride solution (20 ml) was added to the reaction mixture, and the temperature was raised to room temperature. The whole was continuously extracted (ethyl acetate and water) for four days. The organic layer was dried over anhydrous magnesium sulfate, the solvent was evaporated under reduced pressure, and the residue was purified by silica gel column chromatography to give 3-hydroxy-3-(4-pyridyl)propionitrile (666 mg, colorless crystals, 63.5%).

Next, imidazole (4.60 g, 67.5 mmol) and N,N-dimethylformamide (30 ml) were added to the obtained 3-hydroxy-3-(4-pyridyl)propionitrile (1.00 g, 6.75 mmol), and the mixture was stirred at room temperature. t-Butyldiphenylchlorosilane (2.23 g, 8.10 mmol) was added to the mixture, and the whole was stirred for one day and further stirred at an external temperature of 50° C. for three hours. Ethyl acetate (50 ml) and ether (50 ml) were added to the reaction mixture, the whole was washed with water (20 ml) three times and saturated brine (30 ml) successively, and the organic layer was dried over anhydrous magnesium sulfate. The organic layer was concentrated under reduced pressure, and the residue was purified by silica gel column chromatography to give 2.58 g (98.9%) of 3-(t-butyldiphenylsiloxy)-3-(4-pyridyl)propionitrile as a colorless oily matter.

Lithium aluminum hydride (299 mg, 7.87 mmol) was suspended in anhydrous diethyl ether (10 ml) under a nitrogen atmosphere, and a solution of the obtained 3-(t-butyldiphenylsiloxy)-3-(4-pyridyl)propionitrile (1.00 g, 2.59 mmol) in anhydrous diethyl ether (15 ml) was added dropwise to the suspension under ice-cooling with stirring over eight minutes. The temperature was raised to room temperature, and the mixture was stirred for 75 minutes. The reaction mixture was cooled with ice, ethyl acetate (15 ml) was added to the reaction mixture, and water (0.28 ml), a 15% aqueous sodium hydroxide solution (0.28 ml) and water (0.85 ml) were added thereto successively. The temperature was raised to room temperature, and the whole was stirred for 10 minutes. The reaction mixture was dried over anhydrous magnesium sulfate, the solvent was evaporated under reduced pressure, and the residue was purified by silica gel column chromatography to give the titled compound (180.0 mg, yellow oily matter, 17.8%).

IR(neat): 3286, 3071, 2932, 2858, 1601, 1428 cm$^{-1}$

The following compound was obtained by a method similar to Preparation Example 18.

3-(t-Butyldimethylsilyloxy)-3-(4-pyridyl)propylamine (Intermediate No. 18-2)

PREPARATION EXAMPLE 19

N-[2-(1-Adamantyl)ethyl]-2-butynylamine (Intermediate No. 19-1)

Dimethyl sulfoxide (60 ml) and triethylamine (8.4 ml, 60 mmol) were added to 2-butyn-1-ol (3.0 ml, 40 ml), and the mixture was stirred under ice-cold water-cooling. A sulfur trioxide-pyridine complex (4.2 g, 26 mmol) was added to the mixture, after 15 minutes, a sulfur trioxide-pyridine complex (5.1 g, 32 mmol) was further added thereto, and the whole was stirred for 1.5 hours. Water (40 ml) was added to the reaction mixture, and the whole was extracted with methylene chloride (40 ml) twice. The organic layer was washed with 1 N hydrochloric acid (30 ml) twice and water (40 ml) twice and dried over anhydrous magnesium sulfate. The solvent was evaporated under reduced pressure to give 1.0 g (37%) of 2-butynal as a brown oily matter.

Next, 2-(1-adamantyl)ethylamine hydrochloride (2.0 g, 9.3 mmol) was distributed with chloroform (30 ml) and a 1 N aqueous sodium hydroxide solution (40 ml), and the organic layer was dried over anhydrous magnesium sulfate and concentrated under reduced pressure to give 2-(1-adamantyl)ethylamine. Methanol (15 ml) and triethylamine (2.6 ml, 19 mmol) were added to 2-(1-adamantyl)ethylamine, and the mixture was stirred at room temperature. Then, a solution of 2-butynal (0.80 g, 12 mmol) obtained by the above-mentioned reaction in methanol (10 ml) was added to the mixture, and after three hours, sodium borohydride (1.9 g, 50 mmol) was added thereto under ice-cold water-cooling. After one hour, water (40 ml) was added to the reaction mixture, and the whole was extracted with chloroform (60 ml). The organic layer was washed with saturated brine (40 ml) and dried over anhydrous magnesium sulfate. The organic layer was concentrated under reduced pressure, and the residue was purified by silica gel column chromatography to give 0.48 g (22%) of the titled compound as a brown oily matter.

IR(neat): 3302, 2902, 2846, 2279, 2244 cm$^{-1}$

[B] Preparation of the Present Compounds

EXAMPLE 1

1-[2-(1-Adamantyl)ethyl]-1-pentyl-3-[3-(4-pyridyl)propyl]urea (Compound No. 1-1)

1,1'-Carbonyldiimidazole (427 mg, 2.63 mmol) was added to a solution of 4-(3-aminopropyl)pyridine (Intermediate No. 2-1) (285 mg, 2.09 mmol) in tetrahydrofuran (10 ml), and the mixture was stirred at room temperature for 20 minutes. 2-(1-Adamantyl)-N-pentylethylamine hydrochloride (Intermediate No. 1-1) (571 mg, 2.00 mmol) was added to the mixture, and the whole was refluxed for one hour. The reaction mixture was diluted with ethyl acetate (50 ml), the whole was washed with a saturated aqueous sodium hydrogencarbonate solution (50 ml) and a saturated aqueous sodium chloride solution (50 ml) successively, and the organic layer was dried over magnesium sulfate. The solvent was evaporated under reduced pressure, and the precipitated solid was washed with diisopropyl ether and filtered off to give 606 mg (7.3%) of the titled compound.

IR(KBr): 2900, 2845, 1618, 1534 cm$^{-1}$
mp: 124.0-124.7° C.

The following compounds were obtained by a method similar to Example 1.

1-[2-(1-Adamantyl)ethyl]-1-pentyl-3-[3-(4-pyridyl)-2-propenyl]urea (Compound No. 1-2)
IR(neat): 3339, 2902, 2846, 1626, 1530 cm$^{-1}$ N-[3-(4-Pyridyl)propyl]-1-piperidinecarboxamide (Compound No. 1-3)
IR(neat): 3339, 2934, 2854, 1621, 1538 cm$^{-1}$ N-[3-(4-Pyridyl)propyl]-1,2,3,6-tetrahydropyridine-1-carboxamide (Compound No. 1-4)
IR(neat): 3337, 2922, 2858, 1624, 1537, 1414 cm$^{-1}$ N-[3-(4-Pyridyl)propyl]-1,2,3,4-tetrahydroisoquinoline-2-carboxamide (Compound No. 1-5)
IR(KBr): 3342, 2925, 1614, 1543, 1489 cm$^{-1}$
mp: 76.0-79.0° C.

N-[3-(4-Pyridyl)propyl]-4-morpholinecarboxamide (Compound No. 1-6)
IR(KBr): 3347, 2968, 1626, 1546, 1115 cm$^{-1}$
mp: 94.0-98.0° C.

N-[3-(4-Pyridyl)propyl]-1-homopiperidinecarboxamide (Compound No. 1-7)
IR(neat): 3343, 2927, 1625, 1537 cm$^{-1}$ 1,1-Diallyl-3-[3-(4-pyridyl)propyl]urea (Compound No. 1-8)
IR(neat): 3350, 2928, 1628, 1603, 1535 cm$^{-1}$ N-[3-(4-Pyridyl)propyl]-2-decahydroisoquinolinecarboxamide (Compound No. 1-9)
IR(neat): 3343, 2855, 2622, 1621, 1539 cm$^{-1}$ 1,1-Dibutyl-3-[3-(4-pyridyl)propyl]urea (Compound No. 1-10)
IR(neat): 3347, 2957, 2872, 1626, 1537 cm$^{-1}$ 1,1-Dihexyl-3-[3-(4-pyridyl)propyl]urea (Compound No. 1-11)
IR(neat): 3348, 2928, 2857, 1626, 1532 cm$^{-1}$ 1,1-Diisopentyl-3-[3-(4-pyridyl)propyl]urea (Compound No. 1-12)
IR(neat): 3344, 2955, 2869, 1626, 1533 cm$^{-1}$ 1,1-Didecyl-3-[3-(4-pyridyl)propyl]urea (Compound No. 1-13)
IR(neat): 3346, 2925, 2854, 1626, 1537 cm$^{-1}$ 1-[2-(1-Adamantyl)ethyl]-1-[2-(N-benzyloxycarbonyl-N-methylamino)ethyl]-3-[3-(4-pyridyl)propyl]urea (Compound No. 1-14)
IR(neat): 3360, 2902, 2846, 1772, 1699, 1634, 1532 cm$^{-1}$ 1-[2-(1-Adamantyl)ethyl]-1-[2-(dimethylamino)ethyl]-3-[3-(4-pyridyl)propyl]urea (Compound No. 1-15)
IR(KBr): 3322, 2900, 2845, 1621, 1526 cm$^{-1}$
mp: 104.0-106.5° C.

1-[2-(1-Adamantyl)ethyl]-1-propyl-3-[3-(4-pyridyl)propyl]urea (Compound No. 1-16)
IR(KBr): 3331, 2901, 2846, 1622, 1602, 1534 cm$^{-1}$
mp: 99.0-103.0° C.

1-[2-(1-Adamantyl)ethyl]-1-(2-propynyl)-3-[3-(4-pyridyl)propyl]urea (Compound No. 1-17)
IR(KBr): 3322, 3204, 2899, 2845, 2112, 1626, 1605, 1543, 1444 cm$^{-1}$
mp: 152.0-154.0° C.

1-[2-(1-Adamantyl)ethyl]-1-(2-methoxyethyl)-3-[3-(4-pyridyl)propyl]urea (Compound No. 1-18)
IR(KBr): 3321, 2900, 2846, 1625, 1602, 1534, 1451 cm$^{-1}$
mp: 101.5-104.5° C.

1-[2-(1-Adamantyl)ethyl]-1-cyclopropyl-3-[3-(4-pyridyl)propyl]urea (Compound No. 1-19)
IR(KBr): 3365, 2900, 1633 cm$^{-1}$
mp: 108.0-115.5° C.

1-[2-(1-Adamantyl)ethyl]-1-cyanomethyl-3-[3-(4-pyridyl)propyl]urea (Compound No. 1-20)
IR(neat): 3350, 2903, 2247, 1644 cm$^{-1}$ 1-[2-(1-Adamantyl)ethyl]-1-cyclopentylmethyl-3-[3-(4-pyridyl)propyl]urea (Compound No. 1-21)
IR(KBr): 3328, 2906, 2845, 1615, 1450 cm$^{-1}$
mp: 155.0-158.0° C.

1-[2-(1-Adamantyl)ethyl]-1-cyclopropylmethyl-3-[3-(4-pyridyl)propyl]urea (Compound No. 1-22)
IR(KBr): 3328, 2900, 2845, 1618, 1534 cm$^{-1}$
mp: 123.0-125.0° C.

1-[2-(1-Adamantyl)ethyl]-1-allyl-3-[3-(4-pyridyl)propyl]urea (Compound No. 1-23)
IR(KBr): 3329, 2900, 1625, 1538 cm$^{-1}$
mp: 99.0-102.0° C.

1-[2-(1-Adamantyl)ethyl]-3-[3-(4-pyridyl)propyl]-1-(3,3,3-trifluoropropyl)urea (Compound No. 1-24)
IR(KBr): 3310, 2900, 2847, 1622, 1543 cm$^{-1}$
mp: 107.5-109.0° C.

1-[2-(1-Adamantyl)ethyl]-1-(2-butenyl)-3-[3-(4-pyridyl)propyl]urea (Compound No. 1-25)
IR(KBr): 3328, 2900, 1619 cm$^{-1}$
mp: 89.5-93.5° C.

1-[2-(1-Adamantyl)ethyl]-1-[2-[N-(t-butoxycarbonyl)-N-methylamino]ethyl]-3-[3-(4-pyridyl)propyl]urea (Compound No. 1-26)
IR(neat): 3350, 2903, 2846, 1694, 1633, 1537 cm$^{-1}$ 1-[2-(1-Adamantyl)ethyl]-3-[3-(4-pyridyl)propyl]-1-(2-thienyl)methylurea (Compound No. 1-27)
IR(KBr): 3328, 2900, 2845, 1626, 1544 cm$^{-1}$
mp: 142.5-144.5° C.

1-[2-(1-Adamantyl)ethyl]-1-benzyloxy-3-[3-(4-pyridyl)propyl]urea (Compound No. 1-28)
IR(neat): 3444, 3350, 2902, 2846, 1666, 1517 cm$^{-1}$ 1-[2-(1-Adamantyl)ethyl]-1-hexyl-3-[3-(4-pyridyl)propyl]urea (Compound No. 1-29)
IR(KBr): 3354, 2901, 2845, 1619, 1538 cm$^{-1}$
mp: 119.5-121.5° C.

1-(1-Adamantyl)methyl-1-propyl-3-[3-(4-pyridyl)propyl]urea (Compound No. 1-30)
IR(neat): 3350, 2902, 1626 cm$^{-1}$ 1-[2-(1-Adamantyl)ethyl]-1-(3-methyl-2-butenyl)-3-[3-(4-pyridyl)propyl]urea (Compound No. 1-31)
IR(KBr): 3358, 2900, 2845, 1622, 1526 cm$^{-1}$
mp: 93.0-96.0° C.

1-[2-(1-Adamantyl)ethyl]-1-decyl-3-[3-(4-pyridyl)propyl] urea (Compound No. 1-32)
  IR(KBr): 3340, 2924, 2846, 1626, 1602, 1534 cm$^{-1}$
  mp: 75.0-76.0° C.
1-[2-(1-Adamantyl)ethyl]-1-(2-methyl-2-propenyl)-3-[3-(4-pyridyl)propyl]urea (Compound No. 1-33)
  IR(KBr): 3336, 2905, 2846, 1624, 1544 cm$^{-1}$
  mp: 108.0-109.0° C.
1-[2-(1-Adamantyl)ethyl]-1-cinnamyl-3-[3-(4-pyridyl)propyl]urea (Compound No. 1-34)
  IR(KBr): 3374, 2899, 2844, 1619, 1534 cm$^{-1}$
  mp: 130.0-134.5° C.
1-[3-(1-Adamantyl)propyl]-1-propyl-3-[3-(4-pyridyl)propyl]urea (Compound No. 1-35)
  IR(neat): 3349, 2901, 1626, 1536 cm$^{-1}$
1-(1-Adamantyl)methyl-1-pentyl-3-[3-(4-pyridyl)propyl] urea (Compound No. 1-36)
  IR(neat): 3349, 2903, 1625, 1531 cm$^{-1}$
1-[2-(1-Adamantyl)ethyl]-1-(2-methylthiazol-4-yl)methyl-3-[3-(4-pyridyl)propyl]urea (Compound No. 1-37)
  IR(neat): 3337, 2901, 1632, 1536 cm$^{-1}$
1,1-Dipentyl-3-[3-(4-pyridyl)propyl]urea (Compound No. 1-38)
  IR(neat): 3347, 2929, 2859, 1626, 1537 cm$^{-1}$
1-Pentyl-1-(2-piperidinoethyl)-3-[3-(4-pyridyl)propyl]urea (Compound No. 1-39)
  IR(neat): 3350, 2933, 2856, 1640, 1533 cm$^{-1}$
1-[2-(1-Adamantyl)ethyl]-1-methyl-3-[3-(4-pyridyl)propyl] urea (Compound No. 1-40)
  IR(KBr): 3334, 2901, 2846, 1626, 1604, 1534 cm$^{-1}$
  mp: 99.0-109.0° C.
1-[2-(1-Adamantyl)ethyl]-1-ethyl-3-[3-(4-pyridyl)propyl] urea (Compound No. 1-41)
  IR(KBr): 3324, 2901, 2845, 1622, 1540 cm$^{-1}$
  mp: 106.0-115.0° C.
1-[2-(1-Adamantyl)ethyl]-1-furfuryl-3-[3-(4-pyridyl)propyl]urea (Compound No. 1-42)
  IR(KBr): 3331, 2900, 2846, 1618, 1538 cm$^{-1}$
  mp: 128.0-130.0° C.
1-[2-(1-Adamantyl)ethyl]-1-benzyl-3-[3-(4-pyridyl)propyl] urea (Compound No. 1-43)
  IR(KBr): 3335, 2901, 2847, 1619, 1538 cm$^{-1}$
  mp: 130.5-135.0° C.
1-(2-Cyclohexylethyl)-1-pentyl-3-[3-(4-pyridyl)propyl]urea (Compound No. 1-44)
  IR(neat): 3345, 2923, 1625, 1603, 1531 cm$^{-1}$
1-Pentyl-1-phenethyl-3-[3-(4-pyridyl)propyl]urea (Compound No. 1-45)
  IR(neat): 3345, 3063, 2929, 1625, 1533 cm$^{-1}$
1-Butyl-1-(2-cyclohexylethyl)-3-(4-pyridyl)methylurea (Compound No. 1-46)
  IR(neat): 3342, 2922, 2851, 1629, 1602, 1563, 1530, 1448 cm$^{-1}$
1-(2-Cyclohexylethyl)-1,3-bis[(4-pyridyl)methyl]urea (Compound No. 1-47)
  IR(neat): 3337, 3029, 2922, 2850, 1633, 1602, 1534, 1445 cm$^{-1}$
1-(2-Cyclohexylethyl)-3-(4-pyridyl)methyl-1-(2-thienyl) methylurea (Compound No. 1-48)
  IR(neat): 3342, 2921, 2850, 1631, 1602, 1562, 1536, 1415, 1267, 1227 cm$^{-1}$
1-[2-(t-Butoxycarbonyl)ethyl]-1-(2-cyclohexylethyl)-3-(4-pyridyl)methylurea (Compound No. 1-49)
  IR(neat): 3347, 2977, 2923, 2851, 1727, 1633, 1602, 1563, 1531, 1449 cm$^{-1}$
1-(2-Cyclohexylethyl) 1-[2-(methoxycarbonyl)ethyl]-3-(4-pyridyl)methylurea (Compound No. 1-50)
  IR(neat): 3348, 2923, 2850, 1737, 1633, 1603, 1563, 1532, 1437 cm$^{-1}$
1-(2-Carbamoylethyl)-1-(2-cyclohexylethyl)-3-(4-pyridyl) methylurea (Compound No. 1-51)
  IR(neat): 3324, 2922, 2850, 1673, 1632, 1606, 1563, 1530, 1448 cm$^{-1}$
1-(2-Cyclohexylethyl)-1-pentyl-3-(4-pyridyl)methylurea (Compound No. 1-52)
  IR(KBr): 3313, 2925, 1627, 1602, 1527, 1410 cm$^{-1}$
  mp: 64.7-65.8° C.
1-(2-Cyclohexylethyl) 1-(2-dimethylaminoethyl)-3-(4-pyridyl)methylurea (Compound No. 1-53)
  IR(KBr): 3346, 2922, 2850, 2778, 1635, 1562, 1533, 1448 cm$^{-1}$
1-[2-[N-(t-Butoxycarbonyl)-N-methylamino]ethyl]-1-(2-cyclohexylethyl)-3-(4-pyridyl)methylurea (Compound No. 1-54)
  IR(neat): 3338, 2976, 2924, 2851, 1694, 1633, 1602, 1563, 1531, 1484, 1450 cm$^{-1}$
1-Pentyl-1-[2-(2-pyridyl)ethyl]-3-[3-(4-pyridyl)propyl]urea (Compound No. 1-55)
  IR(neat): 3350, 2929, 2859, 1633, 1602, 1537 cm$^{-1}$
1,1-Bis[2-(1-adamantyl)ethyl]-3-[3-(4-pyridyl)propyl]urea (Compound No. 1-56)
  IR(neat): 3358, 2901, 2845, 1625, 1530 cm$^{-1}$
  mp: 80° C.
1-[2-(1-Adamantyl)ethyl]-1-butyl-3-[3-(4-pyridyl)propyl] urea (Compound No. 1-57)
  IR(KBr): 3315, 2901, 1618, 1534 cm$^{-1}$
  mp: 109.5-118.0° C.
1,1-Bis(2-hydroxypropyl)-3-[3-(4-pyridyl)propyl]urea hydrochloride (Compound No. 1-58)
  IR(neat): 3350, 1688, 1638, 1538 cm$^{-1}$
1-[Bis(t-butoxycarbonylaminomethyl)]methyl-1-isopentyl-3-[3-(4-pyridyl)propyl]urea (Compound No. 1-59)
  IR(neat): 3326, 2960, 1698, 1631, 1525 cm$^{-1}$
1-Cyclohexyl(phenyl)methyl-1-(3-phenylpropyl)-3-[3-(4-pyridyl)propyl]urea (Compound No. 1-60)
  IR(KBr): 3352, 2931, 1619, 1522 cm$^{-1}$
  mp: 107.0-112.0° C.
1,1-Dicyclohexyl-3-[3-(4-pyridyl)propyl]urea (Compound No. 1-61)
  IR(KBr): 3304, 2930, 2848, 1638, 1602, 1533 cm$^{-1}$
  mp: 143.0-145.5° C.
1-[2-[N-(t-Butoxycarbonyl)-N-methylamino]ethyl]-1-phenethyl-3-[3-(4-pyridyl)propyl]urea (Compound No. 1-62)
  IR(neat): 3350, 1694, 1633, 1532, 1166 cm$^{-1}$
1-[2-[N-(t-Butoxycarbonyl)-N-methylamino]ethyl]-1-pentyl-3-[3-(4-pyridyl)propyl]urea (Compound No. 1-63)
  IR(neat): 3350, 1694, 1632, 1537, 1167 cm$^{-1}$
1-[2-(N-Benzyloxycarbonyl-N-methylamino)ethyl]-1-phenethyl-3-[3-(4-pyridyl)propyl]urea (Compound No. 1-64)
  IR(neat): 3350, 1698, 1632, 1531 cm$^{-1}$
1-[3-(1-Adamantyl)propyl]-1-pentyl-3-[3-(4-pyridyl)propyl]urea (Compound No. 1-65)
  IR(KBr): 3333, 2901, 2844, 1623, 1602, 1543 cm$^{-1}$
1-[2-(1-Adamantyl)ethyl]-3-pentyl-1-[3-(4-pyridyl)propyl] urea (Compound No. 1-66)
  IR(KBr): 3370, 3322, 2903, 2846, 1618, 1534 cm$^{-1}$
  mp: 47.0-50.0° C.
3-[2-(1-Adamantyl)ethyl]-1-[2-(t-butoxycarbonyl)ethyl]-1-[3-(4-pyridyl)propyl]urea (Compound No. 1-67)
  IR(neat): 3348, 2902, 2846, 1726, 1627, 1538, 1367, 1152 cm$^{-1}$ 1-[2-(1-Adamantyl)ethyl]-1-isopropyl-3-[3-(4-pyridyl)propyl]urea (Compound No. 1-68)
IR(KBr): 3330, 2903, 2845, 1614, 1533 cm$^{-1}$
mp: 132.0-134.0° C.

1-[2-(1-Adamantyl)ethyl]-1-[2-(t-butoxycarbonyl)ethyl]-3-[3-(4-pyridyl)propyl]urea (Compound No. 1-69)
IR(KBr): 3356, 2903, 1720, 1622, 1538, 1156 cm$^{-1}$
mp: 124.5-127.0° C.

1-[2-(1-Adamantyl)ethyl]-1-cyclopentyl-3-[3-(4-pyridyl)propyl]urea (Compound No. 1-70)
IR(KBr): 3297, 2906, 2844, 1618, 1544 cm$^{-1}$
mp: 135.5-137.5° C.

1-[2-(1-Adamantyl)ethyl]-1-(t-butoxycarbonylamino)-3-[3-(4-pyridyl)propyl]urea (Compound No. 1-71)
IR(neat): 3231, 2903, 1732, 1650 cm$^{-1}$ 1-[2-(1-Adamantyl)ethyl]-1-pentyl-3-(2-pyridyl)methylurea (Compound No. 1-72)
IR(KBr): 3333, 2900, 2844, 1625, 1535 cm$^{-1}$
mp: 87.5-92.0° C.

1-[2-(1-Adamantyl)ethyl]-1-pentyl-3-(3-pyridyl)methylurea (Compound No. 1-73)
IR(KBr): 3328, 2901, 2846, 1622, 1530 cm$^{-1}$
mp: 88.5-101.5° C.

1-[2-(1-Adamantyl)ethyl]-1-pentyl-3-(4-pyridyl)methylurea (Compound No. 1-74)
IR(KBr): 3331, 2900, 2845, 1626, 1538 cm$^{-1}$
mp: 96.5-108.0° C.

1-[2-(1-Adamantyl)ethyl]-1-pentyl-3-[2-(2-pyridyl)ethyl]urea (Compound No. 1-75)
IR(KBr): 3346, 2904, 2845, 1622, 1539 cm$^{-1}$
mp: 80.0-100.0° C.

1-[2-(1-Adamantyl)ethyl]-1-pentyl-3-[2-(3-pyridyl)ethyl]urea (Compound No. 1-76)
IR(KBr): 3334, 2900, 2845, 1618, 1541 cm$^{-1}$
mp: 112.5-114.5° C.

1-(2-Cyclohexylethyl)-1-(2-methoxyethyl)-3-(4-pyridyl)methylurea (Compound No. 1-77)
IR(neat): 3350, 2922, 2850, 1633, 1603, 1534 cm$^{-1}$ 1-[2-(N-Benzyloxycarbonyl-N-methylamino)ethyl]-1-pentyl-3-[3-(4-pyridyl)propyl]urea (Compound No. 1-78)
IR(neat): 3358, 2930, 1701, 1633, 1534 cm$^{-1}$ 1-Ethyl-3-[3-(4-pyridyl)propyl]-1-(3,4,5-trimethoxyphenethyl)urea (Compound No. 1-79)
IR(neat): 3350, 2936, 1626, 1590, 1530, 1239 cm$^{-1}$ 1-[2-(1-Adamantyl)ethyl]-1-pentyl-3-[2-(4-pyridyl)ethyl]urea (Compound No. 1-80)
IR(KBr): 3346, 2901, 2844, 1622, 1538 cm$^{-1}$
mp: 107-118° C.

1-[2-(1H-5-Imidazolyl)ethyl]-1-isopentyl-3-[3-(4-pyridyl)propyl]urea (Compound No. 1-81)
IR(neat): 3117, 2954, 1606, 1537 cm$^{-1}$ 1-Cyclohexyl-1-(3,4-dimethoxyphenethyl)-3-[3-(4-pyridyl)propyl]urea (Compound No. 1-82)
IR(neat): 3353, 2931, 1621, 1515, 1236, 1029 cm$^{-1}$ 1-[2-(1-Adamantyl)ethyl]-1-pentyl-3-[3-(2-pyridyl)propyl]urea (Compound No. 1-83)
IR(KBr): 3324, 2900, 2845, 1622, 1538 cm$^{-1}$
mp: 84.4-85.7° C.

1-[2-(1-Adamantyl)ethyl]-1-pentyl-3-[3-(3-pyridyl)propyl]urea (Compound No. 1-84)
IR(KBr): 3355, 2902, 2845, 1615, 1526 cm$^{-1}$
mp: 99.9-105.2° C.

1-Cyclopropyl-3-[3-(4-pyridyl)propyl]-1-(3,4,5-trimethoxyphenethyl)urea (Compound No. 1-85)
IR(neat): 3400, 2938, 1644, 1590, 1510, 1239, 1128 cm$^{-1}$ 1-[2-(1-Adamantyl)ethyl]-3-(4-dimethylamino)phenethyl-1-pentylurea (Compound No. 1-86)
IR(KBr): 3341, 2900, 2845, 1619, 1526 cm$^{-1}$
mp: 115.8-118.1° C.

1-[2-(1-Adamantyl)ethyl]-1-pentyl-3-[4-(4-pyridyl)butyl]urea (Compound No. 1-87)
IR(KBr): 3354, 2900, 2844, 1618, 1538 cm$^{-1}$
mp: 74.1-78.1° C.

1-[2-(1-Adamantyl)ethyl]-3-(butoxycarbonyl)-1-pentyl-3-[2-(4-pyridyl)oxyethyl]urea (Compound No. 1-88)
IR(neat): 2903, 2847, 1704, 1590 cm$^{-1}$ 1-[2-(1-Adamantyl)ethyl]-1-[3-[N-(t-butoxycarbonyl)-N-methylamino]propyl]-3-[3-(4-pyridyl)propyl]urea (Compound No. 1-89)
IR(neat): 3350, 2903, 2847, 1694, 1632, 1531 cm$^{-1}$ 1-Cyclohexyl(phenyl)methyl-1-[3-(4-methoxyphenoxy)propyl]-3-[3-(4-pyridyl)propyl]urea (Compound No. 1-90)
IR(neat): 3369, 2930, 1626, 1510, 1231 cm$^{-1}$ 1-[2-(1-Adamantyl)ethyl]-1-pentyl-3-[3-(4-quinolyl)propyl]urea (Compound No. 1-91)
IR(KBr): 3354, 2902, 2845, 1622, 1534 cm$^{-1}$
mp: 80.2-102.0° C.

1-[2-(1-Adamantyl)ethyl]-1-[2-[N-(1-imidazolylcarbonyl)-N-methylamino]ethyl]-3-[3-(4-pyridyl)propyl]urea (Compound No. 1-92)
IR(neat): 3366, 2902, 2846, 1695, 1635, 1604, 1531 cm$^{-1}$ 1-Diphenylmethyl-1-(3-phenylpropyl)-3-[3-(4-pyridyl)propyl]urea (Compound No. 1-93)
IR(KBr): 3334, 3026, 2927, 1621, 1522 cm$^{-1}$
mp: 123.0-124.8° C.

1,1-Di(5-hexenyl)-3-[3-(4-pyridyl)propyl]urea (Compound No. 1-94)
IR(neat): 3350, 3074, 2930, 2859, 1621; 1538 cm$^{-1}$ 1,1-Di(7-octenyl)-3-[3-(4-pyridyl)propyl]urea (Compound No. 1-95)
IR(neat): 3349, 3074, 2927, 2856, 1625, 1537 cm$^{-1}$ 4-[2-[3-[2-(1-Adamantyl)ethyl]-3-pentyl]ureidoethyl]benzenesulfonamide (Compound No. 1-96)
IR(KBr): 3423, 2906, 2847, 1598, 1540, 1161 cm$^{-1}$
mp: 85.0-120.7° C.

1-[2-(1-Adamantyl)ethyl]-3-(1-imidazolyl)propyl-1-pentylurea (Compound No. 1-97)
IR(KBr): 3340, 2902, 2845, 1618, 1534 cm$^{-1}$
mp: 97.0-100.0° C.

1-[2-(1-Adamantyl)ethyl]-3-(4-hydroxyphenethyl)-1-pentylurea (Compound No. 1-98)
IR(KBr): 3392, 2902, 2845, 1614, 1535, 1515 cm$^{-1}$
mp: 96.3-99.4° C.

1-[2-(1-Adamantyl)ethyl]-1-[2-(3-t-butyl-1-methylureido)ethyl]-3-[3-(4-pyridyl)propyl]urea (Compound No. 1-99)
IR(neat): 3310, 2903, 1632, 1537 cm$^{-1}$ 1-[2-(1-Adamantyl)ethyl]-3-[2-methyl-3-(4-pyridyl)propyl]-1-pentylurea (Compound No. 1-100)
IR(KBr): 3347, 2957, 2902, 2846, 1621, 1604, 1539 cm$^{-1}$
mp: 105.3-112.3° C.

1-[2-(1-Adamantyl)ethyl]-1-[2-(1-methyl-3-propylureido)ethyl]-3-[3-(4-pyridyl)propyl]urea (Compound No. 1-101)
IR(neat): 3316, 2902, 1631, 1537 cm$^{-1}$ 1-Pentyl-1-(3-phenylpropyl)-3-[3-(4-pyridyl)propyl]urea (Compound No. 1-102)
IR(neat): 3348, 2929, 1625, 1537 cm$^{-1}$ 1-[2-(Acetylamino)ethyl]-1-[2-(1-adamantyl)ethyl]-3-[3-(4-pyridyl)propyl]urea (Compound No. 1-103)
IR(neat): 3291, 2902, 2846, 1632, 1556, 753 cm$^{-1}$ 1-[2-(1-Adamantyl)ethyl]-1-pentyl-3-[3-(4-pyridyl)butyl] urea (Compound No. 1-104).
IR(KBr): 3346, 2901, 2845, 1618, 1601, 1539 cm$^{-1}$
mp: 93.0-98.0° C.

1-[2-(1-Adamantyl)ethyl]-3-[3-(4-pyridyl)propyl]-1-(4,4,4-trifluorobutyl)urea (Compound No. 1-105)
IR(KBr): 3317, 2901, 2846, 1618, 1538, 1255, 1123 cm$^{-1}$
mp: 142.6-145.0° C.

1-[2-(1-Adamantyl)ethyl]-3-[3-(4-pyridyl)propyl]-1-(5,5,5-trifluoropentyl)urea (Compound No. 1-106)
IR(KBr): 3333, 2900, 2846, 1618, 1534, 1259, 1140 cm$^{-1}$
mp: 116.9-118.9° C.

1-[2-(1-Adamantyl)ethyl]-1-[2-[N-(t-butoxycarbonyl)-N-methylamino]ethyl]-3-[2-methyl-3-(4-pyridyl)propyl] urea (Compound No. 1-107)
IR(neat): 3350, 2902, 2846, 1694, 1672, 1633, 1603, 1537 cm$^{-1}$ 1-[2-(1-Adamantyl)ethyl]-1-pentyl-3-[2-(4-pyridylmethyl) butyl]urea (Compound No. 1-108)
IR(KBr): 3347, 2900, 2845, 1622, 1538 cm$^{-1}$
mp: 72.0-77.0° C.

1-[2-(1-Adamantyl)ethyl]-3-[2-benzyl-3-(4-pyridyl)propyl]-1-pentylurea (Compound No. 1-109)
IR(KBr): 3329, 2902, 2846, 1622, 1544 cm$^{-1}$
mp: 111.0-116.0° C.

1-[2-(1-Adamantyl)ethyl]-3-[2,2-bis(4-pyridylmethyl) ethyl]-1-pentylurea (Compound No. 1-110)
IR(KBr): 3330, 2905, 2845, 1619, 1602, 1534 cm$^{-1}$
mp: 124.0-136.0° C.

(Z)-1-[2-(1-Adamantyl)ethyl]-1-pentyl-3-[3-(4-pyridyl)-2-propenyl]urea (Compound No. 1-111)
IR(neat): 3338, 2901, 2846, 1625, 1596, 1530 cm$^{-1}$ (E)-1-[2-(1-Adamantyl)ethyl]-1-pentyl-3-[3-(4-pyridyl)-2-propenyl]urea (Compound No. 1-112)
IR(KBr): 3315, 2900, 2845, 1623, 1526 cm$^{-1}$
mp: 90-118° C.

1-Isopentyl-3-[3-(4-pyridyl)propyl]-1-(3,3,3-trifluoropropyl)urea (Compound No. 1-113)
IR(neat): 3342, 2956, 1628, 1604, 1539 cm$^{-1}$ 1-[2-(1-Adamantyl)ethyl]-3-[3-(4-pyridyl)propyl]-1-(2,2,2-trifluoroethyl)urea (Compound No. 1-114)
IR(KBr): 3346, 2901, 2847, 1630, 1604, 1544, 1145, 1108 cm$^{-1}$
mp: 106.2-107.3° C.

3-[2-Methyl-3-(4-pyridyl)propyl]-1-pentyl-1-phenethylurea (Compound No. 1-115)
IR(KBr): 3352, 2927, 2858, 1622, 1530, 1496, 1453, 1416, 1276 cm$^{-1}$
mp: 49.0-50.0° C.

1,1-Dibutyl-3-[2-methyl-3-(4-pyridyl)propyl]urea (Compound No. 1-116)
IR(neat): 3347, 2957, 2929, 1624, 1534 cm$^{-1}$ 1-[2-(1-Adamantyl)ethyl]-3-[2-methyl-3-(4-pyridyl)propyl]-1-(3,3,3-trifluoropropyl)urea (Compound No. 1-117)
IR(KBr): 3354, 2901, 2847, 1626, 1540 cm$^{-1}$
mp: 81.1-84.1° C.

1-(2-Cyclohexylethyl)-3-[2-methyl-3-(4-pyridyl)propyl]-1-pentylurea (Compound No. 1-118)
IR(neat): 3346, 2923, 2852, 1625, 1533 cm$^{-1}$ 1-(3-Cyclohexylpropyl)-1-propyl-3-[3-(4-pyridyl)propyl] urea (Compound No. 1-119)
IR(neat): 3346, 2922, 1626, 1537 cm$^{-1}$ (−)-1-[2-(1-Adamantyl)ethyl]-3-[2-methyl-3-(4-pyridyl) propyl]-1-pentylurea (Compound No. 1-120)
IR(KBr): 3337, 2900, 1616, 1526 cm$^{-1}$
mp: 103.0-104.0° C.
$[\alpha]^{20}_D$: −4.6° (MeOH, C 1.0)

(+)-1-[2-(1-Adamantyl)ethyl]-3-[2-methyl-3-(4-pyridyl) propyl]-1-pentylurea (Compound No. 1-121)
IR(KBr): 3336, 2900, 1616, 1526 cm$^{-1}$
mp: 102.9-103.5° C.
$[\alpha]^{20}_D$: +4.2° (MeOH, C 1.0)

1-[3-(1-Adamantyl)propyl]-1-butyl-3-[3-(4-pyridyl)propyl] urea (Compound No. 1-122)
IR(KBr): 3323, 2954, 2904, 2846, 1624, 1603, 1548 cm$^{-1}$
mp: 79.8-80.4° C.

1-[3-(1-Adamantyl)propyl]-3-[3-(4-pyridyl)propyl]-1-(2,2,2-trifluoroethyl)urea (Compound No. 1-123)
IR(KBr): 3355, 2902, 2848, 1627, 1605, 1545, 1145, 1112 cm$^{-1}$
mp: 88.9-90.0° C.

1-[4-(1-Adamantyl)butyl]-1-ethyl-3-[3-(4-pyridyl)propyl] urea (Compound No. 1-124)
IR(KBr): 3352, 2897, 2847, 1626, 1604, 1539 cm$^{-1}$
mp: 92.7-93.7° C.

1-[4-(1-Adamantyl)butyl]-1-propyl-3-[3-(4-pyridyl)propyl] urea (Compound No. 1-125)
IR(KBr): 3343, 2900, 2847, 1625, 1604, 1544 cm$^{-1}$
mp: 110.0-110.5° C.

1-[2-(1-Adamantyl)ethyl]-1-pentyl-3-[2-(4-pyridylamino) ethyl]urea (Compound No. 1-126)
IR(KBr): 3301, 2904, 2848, 1628, 1602, 1527 cm$^{-1}$
mp: 133.9-134.5° C.

(+)-1-[3-(1-Adamantyl)propyl]-3-[2-methyl-3-(4-pyridyl) propyl]-1-propylurea (Compound No. 1-127)
IR(neat): 3350, 2902, 2846, 1625, 1534 cm$^{-1}$
$[\alpha]^{20}_D$: +4.20 (MeOH, C 0.51)

1-[3-(1-Adamantyl)propyl]-1-propyl-3-(4-pyridyl)methylurea (Compound No. 1-128)
IR(KBr): 3319, 2902, 1630, 1604, 1537 cm$^{-1}$
mp: 96.0-98.0° C.

1-[3-(1-Adamantyl)propyl]-1-propyl-3-[2-(4-pyridyl)ethyl] urea (Compound No. 1-129)
IR(neat): 3345, 2901, 1634, 1538 cm$^{-1}$ 1-[3-(1-Adamantyl)propyl]-1-ethyl-3-[3-(4-pyridyl)propyl] urea (Compound No. 1-130)
IR(KBr): 3345, 2969, 2905, 2845, 1622, 1605, 1535 cm$^{-1}$
mp: 97.5-98.2° C.

1-[2-(1-Adamantyloxy)ethyl]-1-propyl-3-[3-(4-pyridyl)propyl]urea (Compound No. 1-131)
IR(neat): 3344, 2911, 2853, 1642, 1603, 1534 cm$^{-1}$ 1-(1-Adamantyl)aminocarbonylmethyl-1-propyl-3-[3-(4-pyridyl)propyl]urea (Compound No. 1-132)
IR(KBr): 3335, 3261, 2910, 2853, 1662, 1622, 1543 cm$^{-1}$
mp: 132.0-132.5° C.

1-[3-(1-Adamantyl)propyl]-1-propyl-3-[4-(4-pyridyl)butyl] urea (Compound No. 1-133)
IR(neat): 3350, 2901, 1623, 1532 cm$^{-1}$ 1-[3-(1-Adamantyl)propyl]-1-[2-[(N-(t-butoxycarbonyl)-N-methylamino]ethyl]-3-[3-(4-pyridyl)propyl]urea (Compound No. 1-134)
IR(neat): 3347, 2902, 2846, 1696, 1632, 1603, 1534, 1167 cm$^{-1}$ 1-[2-(1-Adamantyl)ethyl]-3-[2,2-dimethyl-3-(4-pyridyl) propyl]-1-pentylurea (Compound No. 1-135)
IR(KBr): 3338, 2905, 1620, 1600, 1541 cm$^{-1}$
mp: 82.5-84.9° C.

1-[3-(1-Adamantyl)propyl]-3-[3-(4-pyridyl)propyl]-1-(3,3,3-trifluoropropyl)urea (Compound No. 1-136)
IR(neat): 3349, 2902, 1628, 1538 cm$^{-1}$ 1-[2-(1-Adamantyl)ethyl]-3-[1-methyl-3-(4-pyridyl)propyl]-1-pentylurea (Compound No. 1-137)
IR(KBr): 3338, 2902, 2847, 1615, 1533 cm$^{-1}$
mp: 128.5-129.0° C.

1-[2-(1-Adamantyl)ethyl]-3-[3-(t-butyldimethylsilyloxy)-3-(4-pyridyl)propyl]-1-pentylurea (Compound No. 1-138)
IR(neat): 3355, 2904, 2849, 1628, 1600, 1532, 1099 cm$^{-1}$ (+)-1-[2-(1-Adamantyl)ethyl]-1-[2-[N-(t-butoxycarbonyl)-N-methylamino]ethyl]-3-[2-methyl-3-(4-pyridyl)propyl]urea (Compound No. 1-139)
IR(KBr): 3345, 2910, 2848, 1693, 1622, 1602, 1538, 1248 cm$^{-1}$
mp: 122.7-123.7° C.
$[\alpha]^{20}{}_D$: +2.8° (MeOH, C 1.0)

1-[2-(1-Adamantyl)aminoethyl]-1-propyl-3-[3-(4-pyridyl)propyl]urea (Compound No. 1-140)
IR(neat): 3275, 2908, 2849, 1636, 1536 cm$^{-1}$ 1-[2-(1-Adamantyl)ethyl]-1-(2-butynyl)-3-[3-(4-pyridyl)propyl]urea (Compound No. 1-141)
IR(neat): 3351, 2903, 2847, 2290, 2221, 1630, 1605, 1538 cm$^{-1}$ 1-[2-(1-Adamantyl)ethyl]-3-[1,2-dimethyl-3-(4-pyridyl)propyl]-1-pentylurea (Compound No. 1-142)
IR(neat): 3354, 2904, 2847, 1623, 1604, 1525 cm$^{-1}$ 1-[2-(1-Adamantyl)ethyl]-3-[1-ethyl-3-(4-pyridyl)propyl]-1-pentylurea (Compound No. 1-143)
IR(neat): 3352, 2904, 2847, 1622, 1605, 1529 cm$^{-1}$ 1-[2-(1-Adamantyl)ethyl]-3-[3-(t-butyldiphenylsilyloxy)-3-(4-pyridyl)propyl]-1-pentylurea (Compound No. 1-144)
IR(neat): 3360, 3072, 3050, 2903, 2849, 1634, 1602, 1532, 1428 cm$^{-1}$

EXAMPLE 2

5-(4-Pyridyl)valeric acid N-[2-(1-adamantyl)ethyl]-N-propylamide (Compound No. 2-1)

N,N-Dimethylformamide (8.4 ml) was added to a mixture of 2-(1-adamantyl)-N-propylethylamine (Intermediate No. 1-6) (0.37 g, 1.7 mmol) and 5-(4-pyridyl)valeric acid (Intermediate No. 5-1) (0.30 g, 1.7 mmol), and the whole was stirred at room temperature. N-Methylmorpholine (0.27 ml, 2.5 mmol) and then 1-ethyl-3-(3-dimethylaminopropyl)carbodiimide hydrochloride (0.38 g, 2.0 mmol) were added thereto, and the whole was stirred overnight. The reaction mixture was concentrated under reduced pressure, ethyl acetate (20 ml) was added to the residue, and the whole was washed with a saturated aqueous sodium hydrogencarbonate solution (20 ml) and saturated brine (5 ml) successively. The organic layer was dried over sodium sulfate, and ethyl acetate was evaporated under reduced pressure. The residue was purified by basic silica gel column chromatography to give 0.21 g (33%) of the titled compound as a colorless oily matter.
IR(neat): 2092, 2846, 1644, 1602 cm$^{-1}$ The following compounds were obtained by a method similar to Example 2.

5-(4-Pyridyl)valeric acid N-(1-adamantyl)methyl-N-propylamide (Compound No. 2-2)
IR(neat): 3067, 2903, 2847, 1644, 1602 cm$^{-1}$ 5-(4-Pyridyl)valeric acid N-(1-adamantyl)methyl-N-pentylamide (Compound No. 2-3)
IR(neat): 2903, 2847, 1644, 1601, 1454 cm$^{-1}$ 5-(4-Pyridyl)valeric acid N,N-dibutylamide (Compound No. 2-4)
IR(neat): 2958, 2932, 1641, 1602 cm$^{-1}$ 5-(4-Pyridyl)valeric acid N,N-diisopentylamide (Compound No. 2-5)
IR(neat): 2956, 2870, 1639, 1603 cm$^{-1}$ 5-(4-Pyridyl)valeric acid N-[2-(1-adamantyl)ethyl]-N-(2-butenyl)amide (Compound No. 2-6)
IR(neat): 2903, 2847, 1642, 1602 cm$^{-1}$ 5-(4-Pyridyl)valeric acid N-[2-(1-adamantyl)ethyl]-N-[2-[N'-(t-butoxycarbonyl)-N'-methylamino]ethyl]amide (Compound No. 2-7)
IR(neat): 2904, 2847, 1695, 1644, 1602 cm$^{-1}$ 5-(4-Pyridyl)valeric acid N-[3-(1-adamantyl)propyl]-N-propylamide (Compound No. 2-8)
IR(neat): 2902, 2846, 1643, 1602 cm$^{-1}$ 5-(4-Pyridyl)valeric acid N-pentyl-N-phenethylamide (Compound No. 2-9)
IR(neat): 2930, 2860, 1642, 1602 cm$^{-1}$ 5-(4-Pyridyl)valeric acid N-[2-(1-adamantyl)ethyl]1-N-(2-dimethylaminoethyl)amide (Compound No. 2-10)
IR(neat): 2903, 2847, 1639, 1605 cm$^{-1}$ 5-(4-Pyridyl)valeric acid N-(2-cyclohexylethyl)-N-pentylamide (Compound No. 2-11)
IR(neat): 2924, 2853, 1644, 1601 cm$^{-1}$ 5-(4-Pyridyl)valeric acid N,N-bis[2-(1-adamantyl)ethyl]amide (Compound No. 2-12)
IR(neat): 2901, 2846, 1643, 1602 cm$^{-1}$ 5-(4-Pyridyl)valeric acid N-[2-(1-adamantyl)ethyl]-N-(3,3,3-trifluoropropyl)amide (Compound No. 2-13)
IR(neat): 2904, 2848, 1647, 1602 cm$^{-1}$ 5-(4-Pyridyl)valeric acid N-[2-(1-adamantyl)ethyl]-N-pentylamide (Compound No. 2-14)
IR(neat): 2903, 2847, 1736, 1643, 1602 cm$^{-1}$ 3-(4-Pyridylmethylthio)propionic acid N-[2-(1-adamantyl)ethyl]-N-pentylamide (Compound No. 2-15)
IR(neat): 2903, 1643, 1599 cm$^{-1}$ 2-Methyl-3-(4-pyridylmethylthio)propionic acid N-[2-(1-adamantyl)ethyl]-1N-pentylamide (Compound No. 2-16)
IR(neat): 2903, 1639, 1600 cm$^{-1}$ 2-(Butoxycarbonyl)amino-3-(4-pyridylmethylthio)propionic acid N-[2-(1-adamantyl)ethyl]-N-pentylamide (Compound No. 2-17)
IR(neat): 3284, 2903, 1705, 1644 cm$^{-1}$ 2-[2-(4-Pyridyl)ethylthio]acetic acid N-[2-(1-adamantyl)ethyl]-N-pentylamide (Compound No. 2-18)
IR(neat): 2902, 1635, 1602 cm$^{-1}$ (2R)-2-(t-Butoxycarbonyl)amino-3-[2-(4-pyridyl)ethylthio]propionic acid N-[2-(1-adamantyl)ethyl]-N-pentylamide (Compound No. 2-19)
IR(neat): 3287, 2903, 1705, 1644, 1602 cm$^{-1}$
$[\alpha]^{20}{}_D$: −19.0° (MeOH, C 0.43)

6-(4-Pyridyl)caproic acid N-[2-(1-adamantyl)ethyl]-N-pentylamide (Compound No. 2-20)
IR(neat): 2903, 1644, 1602 cm$^{-1}$ 4-(4-Pyridyl)butyric acid N-[2-(1-adamantyl)ethyl]-N-pentylamide (Compound No. 2-21)
IR(neat): 2903, 1644, 1602 cm$^{-1}$

EXAMPLE 3

1-[2-(1-Adamantyl)ethyl]-1-(2-methylaminoethyl)-3-[3-(4-pyridyl)propyl]urea dihydrochloride (Compound No. 3-1)

Methanol (4.4 ml) was added to 1-[2-(1-adamantyl)ethyl]-1-[2-[N-(t-butoxycarbonyl)-N-methylamino]ethyl]-3-[3-(4-pyridyl)propyl]urea (Compound No. 1-26) (0.30 g, 0.6 mmol), a calcium chloride tube was attached to the vessel, and the mixture was stirred at room temperature. A 10% solution of hydrogen chloride in methanol (4.4 ml) was added to the mixture, the whole was stirred for one day, and the reaction mixture was concentrated under reduced pressure to give 0.30 g (quantitatively) of the titled compound as pale yellow noncrystalline powder.
IR(neat): 3351, 2904, 2846, 1634, 1538 cm$^{-1}$ The following compounds were obtained by a method similar to Example 3.

1-(2-Cyclohexylethyl)-1-(2-methylaminoethyl)-3-(4-pyridyl)methylurea dihydrochloride (Compound No. 3-2)
  IR(neat): 3323, 2923, 2850, 1638, 1529, 1449 cm$^{-1}$
1-[2-(1-Adamantyl)ethyl]-1-amino-3-[3-(4-pyridyl)propyl]urea dihydrochloride (Compound No. 3-3)
  IR(KBr): 3410, 2902, 1637 cm$^{-1}$
  mp: about 100° C.
2-Amino-3-(4-pyridylmethylthio)propionic acid N-[2-(1-adamantyl)ethyl]-1-pentylamide dihydrochloride (Compound No. 3-4)
  IR(neat): 3402, 2901, 1638, 1608, 1503 cm$^{-1}$
5-(4-Pyridyl)valeric acid N-[2-(1-adamantyl)ethyl]-N-(2-methylaminoethyl)amide (Compound No. 3-5)
  IR(neat): 3312, 2902, 2846, 1643, 1602, 1450, 1416 cm$^{-1}$
(2R)-2-Amino-3-[2-(4-pyridyl)ethylthio]propionic acid N-[2-(1-adamantyl)ethyl]-N-pentylamide dihydrochloride (Compound No. 3-6)
  IR(KBr): 3423, 2902, 1638, 1609 cm$^{-1}$
  $[\alpha]^{20}_D$: −4.9° (H$_2$O, C 0.52)
1-[2-(1-Adamantyl)ethyl]-1-pentyl-3-[2-(4-pyridyl)oxyethyl]urea (Compound No. 3-7)
  IR(neat): 3246, 2903, 2846, 1698, 1604 cm$^{-1}$

EXAMPLE 4

4-[3-[3-[2-(1-Adamantyl)ethyl]-3-pentylureido]propyl]-1-methylpyridinium iodide (Compound No. 4-1)

Methyl iodide (90 μl, 1.5 mmol) was added to a solution of 1-[2-(1-adamantyl)ethyl]-1-pentyl-3-[3-(4-pyridyl)propyl]urea (Compound No. 1-1) (0.30 g, 0.73 mmol) in acetone (1.5 ml) at room temperature, and the mixture was stirred overnight. The solvent was evaporated under reduced pressure from the reaction mixture, and the precipitated crystals were filtered off with ethyl acetate to give 389 mg (96%) of the titled compound.
  IR(KBr): 3374, 2926, 2900, 1616, 1526 cm$^{-1}$
  mp: 168.0-171.0° C.

The following compounds were obtained by a method similar to Example 4.
4-[3-[3-[2-(1-Adamantyl)ethyl]-3-[2-[N-(t-butoxycarbonyl)-N-methylamino]ethyl]ureido]propyl]-1-methylpyridinium iodide (Compound No. 4-2)
  IR(neat): 3342, 2903, 2846, 1682, 1644, 1520, 1235, 1166 cm$^{-1}$
4-[3-[3-[2-(1-Adamantyl)ethyl]-3-[2-[N-(t-butoxycarbonyl)amino]ethyl]ureido]propyl]-1-benzylpyridinium bromide (Compound No. 4-3)
  IR(KBr): 3312, 2907, 2846, 1714, 1694, 1625, 1534, 1246, 1171 cm$^{-1}$
  mp: 97° C.

EXAMPLE 5

3-(4-Pyridyl)propyl N-[2-(1-adamantyl)ethyl]-N-pentylcarbamate (Compound No. 5-1)

4-Pyridinepropanol (528 mg, 3.85 mmol) was dissolved in acetonitrile (20 ml) at room temperature, and then triethylamine (1.61 ml, 11.6 mmol) was added to the solution. Further, N,N'-disuccinimidyl carbonate (1.48 g, 5.87 mmol) was added to the mixture, and the whole was stirred for 2.5 hours. The reaction mixture was concentrated under reduced pressure, and ethyl acetate (100 ml) and a saturated aqueous sodium hydrogencarbonate solution (50 ml) were added to the residue. Layers were separated, and the obtained organic layer was washed with a saturated aqueous sodium chloride solution (50 ml). The organic layer was dried over anhydrous sodium sulfate, and the solvent was evaporated under reduced pressure. The residue was dried under reduced pressure and dissolved in anhydrous methylene chloride (10 ml). Then, a solution of 2-(1-adamantyl)-N-pentylethylamine hydrochloride (Intermediate No. 1-1) (1.32 g, 4.62 mmol) and triethylamine (0.80 ml, 5.7 mmol) in methylene chloride (90 ml) was added thereto, and the mixture was stirred for 1.5 hours. The reaction mixture was washed with a saturated aqueous sodium hydrogencarbonate solution (50 ml) and a saturated aqueous sodium chloride solution (50 ml) successively, and the organic layer was dried over anhydrous sodium sulfate. The solvent was evaporated under reduced pressure, and the residue was purified by silica gel column chromatography to give 1.54 g (97%) of the titled compound as an oily matter.
  IR(neat): 2903, 2847, 1742, 1698 cm$^{-1}$ The following compounds were obtained by a method similar to Example 5.
1-[2-(1-Adamantyl)ethyl]-1-[2-(N-cyclohexyloxycarbonyl-N-methylamino)ethyl]-3-[3-(4-pyridyl)propyl]urea (Compound No. 5-2)
  IR(neat): 3350, 2904, 2847, 1682, 1633, 1604, 1531 cm$^{-1}$
3-(4-Pyridyl)propyl N [3-(1-adamantyl)propyl]-N-propylcarbamate (Compound No. 5-3)
  IR(neat): 2901, 2846, 1740, 1695, 1645, 1602, 1451, 1423 cm$^{-1}$
3-(4-Pyridyl)propyl N-[2-(1-adamantyl)ethyl]-N-(3,3,3-trifluoropropyl)carbamate (Compound No. 5-4)
  IR(neat): 2903, 2847, 1705, 1603, 1482, 1451, 1425 cm$^{-1}$
3-(4-Pyridyl)propyl N-[2-(1-adamantyl)ethyl]-N-[2-[N'-(t-butoxycarbonyl)-N'-methylamino]ethyl]carbamate (Compound No. 5-5)
  IR(neat): 2903, 2847, 1699, 1603, 1480, 1424 cm$^{-1}$
2-Methyl-3-(4-pyridyl)propyl N-[2-(1-adamantyl)ethyl]-N-pentylcarbamate (Compound No. 5-5)
  IR(neat): 2904, 2847, 1701, 1602, 1450, 1424, 1381 cm$^{-1}$

EXAMPLE 6

1-[2-(1-Adamantyl)ethyl]-3-[3-(4-pyridyl)propyl]hexahydro-2,4-pyrimidinedione hydrochloride (Compound No. 6-1)

A 4 N solution of hydrogen chloride in 1,4-dioxane (2.5 ml) was added to 1-[2-(1-adamantyl)ethyl]-1-[2-(t-butoxycarbonyl)ethyl]-3-[3-(4-pyridyl)propyl]urea (Compound No. 1-69) (0.23 g, 0.49 mmol), and the mixture was stirred at room temperature overnight. The reaction mixture was concentrated under reduced pressure, a 1 N aqueous sodium hydroxide solution (20 ml) and ethyl acetate (30 ml) were added to the residue, and layers were separated. The ethyl acetate layer was washed with water (20 ml) and a saturated aqueous sodium chloride solution (20 ml) successively and dried over anhydrous magnesium sulfate. The ethyl acetate layer was concentrated under reduced pressure, and the resulting oily matter was dissolved in diethyl ether (20 ml). A 4 N solution of hydrogen chloride in ethyl acetate (0.50 ml, 2.00 mol) was added thereto under ice-cooling, the mixture was concentrated under reduced pressure, and the precipitated solid was filtered off with ethyl acetate to give 0.17 g (79%) of the titled compound.
  IR(KBr): 2902, 2437, 1710, 1666 cm$^{-1}$
  mp: 177.0-178.5° C.

The following compounds were obtained by a method similar to Example 6.
1-[2-(Cyclohexyl)ethyl]-3-(4-pyridyl)methylhexahydro-2,4-pyrimidinedione hydrochloride (Compound No. 6-2)
  IR(KBr): 2925, 2850, 1718, 1671, 1600, 1493, 1450 cm$^{-1}$
  mp: 64.0-74.5° C.

3-[2-(1-Adamantyl)ethyl]-1-[3-(4-pyridyl)propyl]hexahydro-2,4-pyrimidinedione hydrochloride (Compound No. 6-3)
IR(KBr): 2906, 2845, 1716, 1696, 1658, 1486 cm$^{-1}$
mp: 170° C.

EXAMPLE 7

1-[2-(1-Adamantyl)ethyl]-1-pentyl-3-[3-(4-pyridyl)propyl]thiourea (Compound No. 7-1)

A solution of 4-(3-aminopropyl)pyridine (Intermediate No. 2-1) (0.24 g, 1.8 mmol) in anhydrous tetrahydrofuran (10 ml) was added to 1,1'-thiocarbonyldiimidazole (0.31 g, 1.8 mmol) under a nitrogen atmosphere, and the mixture was stirred at room temperature. After one hour, a solution of 2-(1-adamantyl)-N-pentylethylamine hydrochloride (Intermediate No. 1-1) (0.50 g, 1.8 mmol) in anhydrous tetrahydrofuran (10 ml) was added to the mixture, and the whole was refluxed for 2.5 hours. The reaction mixture was allowed to stand, then ethyl acetate (50 ml) and a saturated aqueous sodium hydrogencarbonate solution (50 ml) were added to the reaction mixture, and layers were separated. The ethyl acetate layer was washed with a saturated aqueous sodium chloride solution (50 ml) and dried over anhydrous magnesium sulfate. The ethyl acetate layer was concentrated under reduced pressure, and the concentrate was purified by silica gel column chromatography to give 0.18 g (24%) of the titled compound.

IR(neat): 3304, 2902, 2846, 1603, 1530, 1345 cm$^{-1}$

The following compound was obtained by a method similar to Example 7.

1-(2-Hydroxyethyl)-1-phenethyl-3-[3-(4-pyridyl)propyl]thiourea (Compound No. 7-2)
IR(KBr): 3022, 2920, 2876, 1606, 1585 cm$^{-1}$
mp: 105.6-107.1° C.

EXAMPLE 8

1-Phenethyl-3-[3-(4-pyridyl)propyl]-2-imidazolidinethione (Compound No. 8-1)

Anhydrous tetrahydrofuran (2.5 ml) was added to a mixture of 1-(2-hydroxyethyl)-1-phenethyl-3-[3-(4-pyridyl)propyl]thiourea (Compound No. 7-2) (601 mg, 1.75 mmol) and triphenylphosphine (913 mg, 3.49 mmol), and the whole was stirred under ice/methanol-cooling. A solution of diisopropyl azodicarboxylate (710 mg, 3.49 mmol) in anhydrous tetrahydrofuran was added dropwise thereto, and after 10 minutes, ethyl acetate (100 ml) was added to the reaction mixture. The whole was washed with a saturated aqueous sodium hydrogencarbonate solution (40 ml) and saturated brine (40 ml) successively, and the organic layer was dried over sodium sulfate and concentrated under reduced pressure. The residue was purified by silica gel column chromatography, and the obtained solid was filtered off with hexane to give 107 mg (19%) of the titled compound as crystals.

IR(KBr): 3064, 3018, 2926, 2858, 1601, 1560, 1498, 1456 cm$^{-1}$
mp: 99.5-104.0° C.

EXAMPLE 9

1-[2-(1-Adamantyl)ethyl]-3-[3-(4-pyridyl)propyl]hexahydropyrimidin-2-one (Compound No. 9-1)

To a solution of 1-adamantaneacetic acid (1.50 g, 7.72 mmol) in anhydrous methylene chloride (30.0 ml) were added 1-hydroxybenzotriazole (1.15 g, 8.49 mmol), β-alanine ethyl ester hydrochloride (1.30 g, 8.49 mmol), 1-ethyl-3-(3-dimethylaminopropyl)carbodiimide hydrochloride (1.63 g, 8.49 mmol) and N-methylmorpholine (2.05 ml, 18.7 mmol) under ice-cooling, and the mixture was stirred at room temperature overnight. The reaction mixture was concentrated under reduced pressure, and ethyl acetate (50 ml) was added to the residue. The whole was washed with a 10% aqueous citric acid solution (50 ml), water (50 ml), a saturated aqueous sodium hydrogencarbonate solution (50 ml), water (50 ml) and a saturated aqueous sodium chloride solution (50 ml) successively, and the organic layer was dried over anhydrous magnesium sulfate. The organic layer was concentrated under reduced pressure to give 2.48 g (quantitatively) of ethyl 3-[(1-adamantly)methylcarboxamido]propionate as a white solid.

Next, ethyl 3-[(1-adamantly)methylcarboxamido]propionate (2.40 g, 8.18 mmol) was dissolved in ethanol (5 ml), a 2 N aqueous sodium hydroxide solution (4.50 ml, 9.00 mmol) was added thereto under ice-cooling, and the mixture was stirred at room temperature for two hours. Under ice-cooling, 2 N hydrochloric acid (15 ml) was added to the reaction mixture to acidify it weakly, and the whole was extracted with ethyl acetate (70 ml). The organic layer was washed with water (50 ml) and a saturated aqueous sodium chloride solution (50 ml) successively and dried over anhydrous magnesium sulfate. The organic layer was concentrated under reduced pressure, and the precipitated solid was filtered off with diethyl ether to give 1.43 g (70.1%) of 3-[(1-adamantyl)methylcarboxamido]propionic acid.

Next, to a solution of 3-[(1-adamantyl)methylcarboxamido]propionic acid (1.4 g, 5.6 mmol) in anhydrous methylene chloride (10 ml) were added 1-hydroxybenzotriazole (0.83 g, 6.2 mmol), 1-ethyl-3-(3-dimethylaminopropyl)carbodiimide hydrochloride (1.2 g, 6.2 mmol), 4-(3-aminopropyl)pyridine (Intermediate No. 2-1) (0.80 g, 5.9 mmol) and N-methylmorpholine (0.68 ml, 6.2 mmol) under ice-cooling, and the mixture was stirred at room temperature overnight. The reaction mixture was concentrated under reduced pressure, and ethyl acetate (50 ml) was added to the residue. The whole was washed with a saturated aqueous sodium hydrogencarbonate solution (30 ml), water (30 ml) and a saturated aqueous sodium chloride solution (30 ml) successively, and the organic layer was dried over anhydrous magnesium sulfate. The organic layer was concentrated under reduced pressure, and the precipitated solid was filtered off with diethyl ether to give 1.9 g (88%) of 3-[(1-adamantyl)methylcarboxamido]propionic acid 3-(4-pyridyl)propylamide.

Anhydrous diethyl ether (20 ml) was added to lithium aluminum hydride (0.45 g, 12 mmol) under ice-cooling. Then, a solution of the obtained 3-[(1-adamantyl)methylcarboxamido]propionic acid 3-(4-pyridyl)propylamide (0.50 g, 1.3 mmol) in anhydrous tetrahydrofuran (10 ml) was added dropwise to the mixture over 15 minutes, and the whole was stirred at room temperature overnight and further refluxed for 4.5 hours. Then, a 2 N aqueous sodium hydroxide solution (30 ml) and ethyl acetate (30 ml) were added carefully to the reaction mixture under ice-cooling, and layers were separated. The ethyl acetate layer was washed with water (30 ml) and a saturated aqueous sodium chloride solution (30 ml) successively and dried over anhydrous magnesium sulfate. The ethyl acetate layer was concentrated under reduced pressure, and the residue was purified by silica gel column chromatography to give 0.05 µg (10%) of N-[2-(1-adamantyl)ethyl]-N'-[3-(4-pyridyl)propyl]-1,3-propanediamine.

To anhydrous methylene chloride (50 ml) were added a solution of the obtained N-[2-(1-adamantyl)ethyl]-N'-[3-(4-pyridyl)propyl]-1,3-propanediamine (80 mg, 0.23 mmol) in anhydrous methylene chloride (10 ml) and a solution of 1,1'- carbonyldiimidazole (40 mg, 0.26 mmol) in anhydrous methylene chloride (10 ml) dropwise simultaneously with stirring at room temperature over 20 minutes. The mixture was stirred overnight, the reaction mixture was concentrated under reduced pressure, and the residue was purified by silica gel column chromatography to give 8.0 mg (9.4%) of the titled compound.

IR(neat): 3400, 2902, 2846, 1625, 1531, 1451 cm$^{-1}$

EXAMPLE 10

1-Acetylamino-1-[2-(1-adamantyl)ethyl]-3-[3-(4-pyridyl) propyl]urea (Compound No. 10-1)

Pyridine (2.0 ml) and acetic anhydride (1.0 ml) were added to 1-[2-(1-adamantyl)ethyl]-1-amino-3-[3-(4-pyridyl)propyl]urea dihydrochloride (Compound No. 3-3) (0.20 g, 0.47 mmol) at room temperature, and the mixture was stirred for 15 minutes. The solvent was evaporated under reduced pressure from the reaction mixture, and the residue was distributed with ethyl acetate (10 ml) and water (10 ml). The organic layer was washed with a saturated aqueous sodium hydrogencarbonate solution (10 ml) and saturated brine (10 ml) and dried over anhydrous magnesium sulfate. The solvent was evaporated under reduced pressure, and the residue was purified by silica gel column chromatography to give 0.11 g (58%) of the titled compound.

IR(KBr): 3374, 3163, 2907, 1694, 1638 cm$^{-1}$
mp: 140.0-146.0° C.

The follwing compounds were obtained by a method similar to Example 10. Acid chlorides were optionally used.

1-[2-(N-Acetyl-N-methylamino)ethyl]-1-[2-(1-adamantyl) ethyl]-3-[3-(4-pyridyl)propyl]urea (Compound No. 10-2)
IR(neat): 3337, 2902, 1632, 1535, 1492 cm$^{-1}$ 1-[2-(1-Adamantyl)ethyl]-1-[2-(N-isonicotinoyl-N-methylamino)ethyl]-3-[3-(4-pyridyl)propyl]urea (Compound No. 10-3)
IR(neat): 3350, 2902, 2846, 1633, 1531, 1450, 1408 cm$^{-1}$ 1-[2-(1-Adamantyl)ethyl]-1-[2-[N-methyl-N-(methlylsulfonyl)amino]ethyl]-3-[3-(4-pyridyl)propyl]urea (Compound No. 10-4)
IR(KBr): 3319, 2902, 2845, 1616, 1540, 1326, 1142 cm$^{-1}$
mp: 164.9-167.2° C.

1-[2-(1-Adamantyl)ethyl]-1-[2-[N-methyl-N-(p-tolylsulfonyl)amino]ethyl]-3-[3-(4-pyridyl)propyl]urea (Compound No. 10-5)
IR(neat): 3358, 2902, 2846, 1633, 1603, 1531, 1343, 1161 cm$^{-1}$ 1-[2-(1-Adamantyl)ethyl]-1-[2-[N-(3,3-dimethylbutyryl)-N-methylamino]ethyl]-3-[3-(4-pyridyl)propyl]urea (Compound No. 10-6)
IR(KBr): 3325, 2906, 2845, 1652, 1616, 1534 cm$^{-1}$
mp: 101.4-102.4° C.

1-[2-(1-Adamantyl)ethyl]-1-[2-(N-ethoxycarbonyl-N-methylamino)ethyl]-3-[3-(4-pyridyl)propyl]urea (Compound No. 10-7)
IR(neat): 3350, 2902, 2846, 1698, 1633, 1532 cm$^{-1}$ 1-[2-(1-Adamantyl)ethyl]-1-[2-[N-(t-butoxycarbonyl) amino]ethyl]-3-[3-(4-pyridyl)propyl]urea (Compound No. 10-8)
IR(KBr): 3312, 2905, 2845, 1710, 1637, 1606, 1534, 1269, 1249, 1174 cm$^{-1}$
mp: 158.0-160.5° C.

1-[2-(1-Adamantyl)ethyl]-1-[2-[N-(t-butoxycarbonyl)-N-ethylamino]ethyl]-3-[3-(4-pyridyl)propyl]urea (Compound No. 10-9)
IR(neat): 3349, 2902, 2846, 1693, 1667, 1633, 1603, 1531, 1452, 1416 cm$^{-1}$ 1-[2-(1-Adamantyl)ethyl]-1-[2-[N-(1,1-dimethyl-2,2,2-trichloroethoxycarbonyl)-N-methylamino]ethyl]-3-[3-(4-pyridyl)propyl]urea (Compound No. 10-10)
IR(neat): 3359, 2903, 2846, 1707, 1636, 1603, 1534 cm$^{-1}$
mp: 47.0-52.0° C.

1-[2-(1-Adamantyl)ethyl]-1-[2-[N-(1,1-dimethylpropoxycarbonyl)-N-methylamino]ethyl]-3-[3-(4-pyridyl)propyl]urea (Compound No. 10-11)
IR(neat): 3349, 2972, 2902, 2846, 1695, 1631, 1603, 1534, 1226, 1159 cm$^{-1}$ 1-[2-(1-Adamantyl)ethyl]-1-[2-(N-isopropoxycarbonyl-N-methylamino)ethyl]-3-[3-(4-pyridyl)propyl]urea (Compound No. 10-12)
IR(neat): 3350, 2903, 2846, 1696, 1632, 1603, 1530 cm$^{-1}$ (−)-1-[2-(1-Adamantyl)ethyl]-1-[2-(N-menthoxycarbonyl-N-methylamino)ethyl]-3-[3-(4-pyridyl)propyl]urea (Compound No. 10-13)
IR(neat): 3350, 2904, 2847, 1694, 1633, 1603, 1530 cm$^{-1}$
$[\alpha]^{20}_D$: −27.5° (MeOH, C 1.0)

1-[2-(1-Adamantyl)ethyl]-1-[2-[N-(3,3-dimethylbutyryl)-N-methylamino]ethyl]-3-[2-methyl-3-(4-pyridyl)propyl] urea (Compound No. 10-14)
IR(neat): 3324, 2902, 2846, 1633, 1537 cm$^{-1}$ 5-(4-Pyridyl)valeric acid N-[2-(1-adamantyl)ethyl]-N-[2-(N'-isopropoxycarbonyl-N-methylamino)ethyl]amide (Compound No. 10-15)
IR(neat): 3553, 2978, 2903, 2847, 1697, 1646 cm$^{-1}$ 5-(4-Pyridyl)valeric acid N-[2-(1-adamantyl)ethyl]-N-[2-(N'-benzyloxycarbonyl-N'-methylamino)ethyl]amide (Compound No. 10-16)
IR(neat): 3387, 3030, 2903, 2847, 1701, 1646, 1602, 1453, 1422 cm$^{-1}$ 5-(4-Pyridyl)valeric acid N-[2-(1-adamantyl)ethyl]-N-[2-[N-(3,3-dimethylbutyryl)-N'-methylamino]ethyl]amide (Compound No. 10-17)
IR(neat): 3501, 2903, 2847, 1645, 1603, 1455, 1417 cm$^{-1}$

EXAMPLE 11

1-[2-(1-Adamantyl)ethyl]-1,3-dimethyl-3-[3-(4-pyridyl) propyl]urea (Compound No. 11-1)

A solution of triphosgene (190 mg, 0.640 mmol) in dichloromethane (6.0 ml) was stirred at room temperature under a nitrogen atmosphere. A solution of 2-(1-adamantyl)-N-methylethylamine (Intermediate No. 3-1) (330 mg, 1.71 mmol) and diisopropylethylamine (0.357 ml, 2.05 mmol) in dichloromethane (6.0 ml) was added dropwise thereto over 17 minutes. After eight minutes, a solution of N-methyl-3-(4-pyridyl)propylamine (Intermediate No. 3-3) (264 mg, 1.78 mmol) and diisopropylethylamine (0.357 ml, 2.05 mmol) in dichloromethane (5.1 ml) was added to the mixture at a stretch, and the whole was stirred for 20 hours. The reaction mixture was diluted with diethyl ether (40 ml), the whole was washed with a saturated aqueous sodium hydrogencarbonate solution (40 ml) twice and a saturated aqueous sodium chloride solution (40 ml) successively, and the organic layer was dried over magnesium sulfate. The solvent was evaporated under reduced pressure, and the residue was purified by silica gel column chromatography to give 335 mg (54%) of the titled compound.

IR(neat): 2903, 2846, 1638, 1602, 1492 cm$^{-1}$

EXAMPLE 12

1-[2-(1-Adamantyl)ethyl]-1-hydroxy-3-[3-(4-pyridyl)propyl]urea (Compound No. 12-1)

2 N Hydrochloric acid (4.0 ml) was added to a solution of 1-[2-(1-adamantyl) ethyl]-1-benzyloxy-3-[3-(4-pyridyl)propyl]urea (Compound No. 1-28) (438 mg, 0.978 mmol) in methanol (9.78 ml), and a nitrogen gas was bubbled through the mixture. To the mixture was added 10% palladium on carbon (43 mg), and the whole was stirred under hydrogen at 1 atm for three days. The palladium on carbon was filtered out, the filtrate was concentrated under reduced pressure, and the concentrate was diluted with diethyl ether (30 ml). The whole was washed with a saturated aqueous sodium hydrogencarbonate solution (30 ml) and a saturated aqueous sodium chloride solution (30 ml) successively, and the organic layer was dried over magnesium sulfate. The solvent was evaporated under reduced pressure, and the residue was purified by silica gel column chromatography to give 119 mg (34%) of the titled compound.

IR(KBr): 3438, 3152, 2903, 2847, 1650 cm$^{-1}$
mp: 101.0-102.5° C.

EXAMPLE 13

1-[2-(1-Adamantyl)ethyl]-1-pentyl-3-[3-(4-pyridyl)propyl] urea hydrochloride (Compound No. 13-1)

A 4 N solution of hydrogen chloride in ethyl acetate (0.400 ml, 1.60 mmol) was added to a solution of 1-[2-(1-adamantyl) ethyl]-1-pentyl-3-[3-(4-pyridyl)propyl]urea (Compound No. 1-1) (200 mg, 0.486 mmol) in chloroform (0.3 ml). The solvent was evaporated under reduced pressure, and the precipitated solid was washed with ethyl acetate and filtered off. The obtained crude crystals were recrystallized from 2-butanone (5.0 ml) to give 94 mg (43%) of the titled compound.

IR(KBr): 3322, 3050, 2902, 2496, 1621, 1534, 1450 cm$^{-1}$
mp: 157.0-158.0° C.

The following compounds were obtained by a method similar to Example 13.

1-[2-(1-adamantyl)ethyl]-1-propyl-3-[3-(4-pyridyl)propyl] urea hydrochloride (Compound No. 13-2)
IR(neat): 3338, 2901, 2845, 1620, 1450 cm$^{-1}$ 1-(2-Cyclohexylethyl)-3-(4-pyridyl)methyl-1-(2-thienyl) methylurea hydrochloride (Compound No. 13-3)
IR(KBr): 3296, 2923, 1635, 1599, 1518 cm$^{-1}$
mp: 161.8-164.4° C.

1-[2-(1-Adamantyl)ethyl]-1-butyl-3-[3-(4-pyridyl)propyl] urea hydrochloride (Compound No. 13-4)
IR(neat): 3331, 2901, 2845, 1754, 1636, 1537 cm$^{-1}$ 1,1-Bis[2-(1-adamantyl)ethyl]-3-[3-(4-pyridyl)propyl]urea hydrochloride (Compound No. 13-5)
IR(KBr): 3289, 2900, 2844, 1637, 1560 cm$^{-1}$
mp: 120.0-122.5° C.

1-[2-(1-Adamantyl)ethyl]-1-(2-aminoethyl)-3-[3-(4-pyridyl) propyl]urea dihydrochloride (Compound No. 13-6)
IR(neat): 3358, 2902, 2846, 1634, 1538, 756 cm$^{-1}$ 2-[2-(4-Pyridyl)ethylamino]acetic acid N-[2-(1-adamantyl) ethyl]-N-pentylamide dihydrochloride (Compound No. 13-7)
IR(KBr): 3424, 2902, 1651 cm$^{-1}$
mp: 133.7-137.0° C.

3-[N'-Methyl-N'-(4-pyridylmethyl)amino]propionic acid N-[2-(1-adamantyl) ethyl]-N-pentylamide dihydrochloride (Compound No. 13-8)
IR(KBr): 3424, 2901, 2846, 1641 cm$^{-1}$ 1,1-Diisopentyl-3-[3-(4-pyridyl)propyl]urea hydrochloride (Compound No. 13-9)

IR(KBr): 3082, 2956, 2869, 2614, 1626, 1526 cm$^{-1}$
mp: 120.5-131.7° C.

1-[3-(1-Adamantyl)propyl]-1-propyl-3-[3-(4-pyridyl)propyl]urea phosphate (Compound No. 13-10)
IR(KBr): 3517, 3423, 1642, 1594, 1539, 1508 cm$^{-1}$
mp: 148.0-149.0° C.

EXAMPLE 14

1-[2-(1-Adamantyl)ethyl]-3-[3-hydroxy-3-(4-pyridyl)propyl]-1-pentylurea (Compound No. 14-1)

A solution of 1-[2-(1-adamantyl)ethyl]-3-[3-(t-butyldimethylsilyloxy)-3-(4-pyridyl)propyl]-1-pentylurea (Compound No. 1-138) (136 mg, 0.250 mmol) in 10% hydrogen chloride-methanol (2.3 ml) was stirred at room temperature for three days. The solvent was evaporated under reduced pressure, the residue was distributed with ethyl acetate (50 ml), water (30 ml) and a 1 N aqueous sodium hydroxide solution (20 ml), and the organic layer was washed with a saturated aqueous sodium chloride solution (40 ml). The organic layer was dried over anhydrous sodium sulfate, the solvent was evaporated under reduced pressure, and the residue was purified by silica gel column chromatography to give the titled compound (59.2 mg, colorless noncrystalline powder, 55.3%).

IR(neat): 3339, 2904, 2847, 1622, 1605, 1532 cm$^{-1}$

EXAMPLE 15 cis-1-[2-(1-Adamantyl)ethyl]-1-pentyl-3-[2-(4-pyridyl) cyclopropylmethyl]urea (Compound No. 15-1)

A 1.0 M solution of diethylzinc in hexane (3.1 ml, 3.1 mmol) and chloroiodomethane (0.44 ml, 6.1 mol) were added to a solution of (Z)-1-[2-(1-adamantyl)ethyl]-1-pentyl-3-[3-(4-pyridyl)-2-propenyl]urea (Compound No. 1-111) in anhydrous 1,2-dichloroethane (3 ml) under a nitrogen atmosphere and ice-cooling, and the mixture was stirred for one hour. A saturated aqueous ammonium chloride solution (10 ml) was added to the reaction mixture under ice-cooling, and the whole was stirred at room temperature for 20 minutes and distributed with ethyl acetate (20 ml) and a saturated aqueous ammonium chloride solution (10 ml). The organic layer was washed with a saturated aqueous sodium chloride solution (10 ml) and dried over anhydrous magnesium sulfate. The solvent was evaporated under reduced pressure, and the resulting residue was purified by silica gel column chromatography to give 9.0 mg (3.5%) of the titled compound as colorless crystals.

IR(KBr): 3340, 3025, 2903, 2847, 1617, 1603, 1525 cm$^{-1}$
mp: 128.0-130.0° C.

EXAMPLE 16

4-[3-[3-[2-(1-Adamantyl)ethyl]-3-pentylureido]propyl]pyridine N-oxide (Compound No. 16-1)

m-Chloroperbenzoic acid (2.5 g, 15 mmol) was added to a solution of 1-[2-(1-adamantyl)ethyl]-1-pentyl-3-[3-(4-pyridyl) propyl]urea (Compound No. 1-1) (3.0 g, 7.3 mmol) at room temperature under a nitrogen atmosphere, and the mixture was stirred overnight. The reaction mixture was distributed with chloroform (20 ml) and a 1 N aqueous sodium hydroxide solution (60 ml). The organic layer was washed with water (10 ml) and a saturated aqueous sodium chloride solution (10 ml) successively and dried over anhydrous magnesium sulfate. The solvent was evaporated under reduced pressure, and the resulting residue was purified by silica gel column chromatography to give 2.92 g (94.2%) of the titled compound.

IR(KBr): 3346, 2902, 2845, 1622, 1538, 1217, 1178 cm$^{-1}$
mp: 97.8-127.0° C.

EXAMPLE 17

1-[2-(1-Adamantyl)ethyl]-1-[2-[N-(2-methoxyethyl)-N-methylamino]ethyl]-3-[3-(4-pyridyl)propyl]urea (Compound No. 17-1)

To N,N-dimethylformamide (20 ml) were added 1-[2-(1-adamantyl) ethyl]-1-(2-methylaminoethyl)-3-[3-(4-pyridyl) propyl]urea (1.50 g, 3.76 mmol), which was a free base of Compound No. 3-1, potassium carbonate (1.56 g, 11.3 mmol) and sodium iodide (1.69 g, 11.3 mmol) at room temperature, then 2-chloroethyl methyl ether (412 μl, 4.51 mmol) was added to the mixture, and the whole was heated at 80° C. The whole was stirred overnight, diethyl ether (50 ml) and water (100 ml) were added to the reaction mixture, and the whole was extracted. The obtained organic layer was washed with water (100 ml) and a saturated aqueous sodium chloride solution (50 ml), dried over anhydrous magnesium sulfate and concentrated under reduced pressure. The residue was purified by silica gel column chromatography to give 552 mg (32.1%) of the titled compound as a pale yellow oily matter.

IR(neat): 3350, 2901, 1643, 1602, 1531 cm$^{-1}$

EXAMPLE 18

2-[2-(4-Pyridyl)ethylamino]acetic acid N-[2-(1-adamantyl) ethyl]-N-pentylamide (Compound No. 18-1)

Bromoacetic acid (0.50 g, 3.6 mmol) was dissolved in anhydrous tetrahydrofuran (20 ml), and the solution was stirred at −15° C. under a nitrogen atmosphere. N-Methylmorpholine (0.40 ml, 3.6 mmol) and isobutyl chlorocarbonate (0.45 ml, 3.5 mmol) were added to the solution. Then, a solution of a free base of 2-(1-adamantyl)-N-pentylethylamine hydrochloride (Intermediate No. 1-1) (1.0 g, 3.5 mmol) in anhydrous tetrahydrofuran (20 ml) was added dropwise to the mixture. The whole was stirred at 0° C. for 1.5 hours, a saturated aqueous sodium hydrogencarbonate solution (70 ml) and ethyl acetate (70 ml) were added to the reaction mixture, and the reaction mixture was distributed. The ethyl acetate layer was washed with water (70 ml) and a saturated aqueous sodium chloride solution (70 ml) successively and dried over anhydrous magnesium sulfate. The ethyl acetate layer was concentrated under reduced pressure to give 1.3 g (quantitatively) of 2-bromoacetic acid N-[2-(1-adamantyl)ethyl]-N-pentylamide as a oily matter.

Next, 2-bromoacetic acid N-[2-(1-adamantyl)ethyl]-N-pentylamide (1.3 g, 3.5 mmol) was dissolved in anhydrous N,N-dimethylformamide (30 ml), potassium carbonate (1.5 g, 11 mmol), methyl iodide (1.6 g, 11 mmol) and 4-(2-aminoethyl)pyridine (0.43 g, 3.5 mmol) were added to the solution, and the mixture was stirred at an external temperature of 75° C. overnight. Water (100 ml) and diethyl ether (100 ml) were added to the reaction mixture, the reaction mixture was distributed, and the diethyl ether layer was washed with water (70 ml) twice and a saturated aqueous sodium chloride solution (120 ml) once successively and dried over anhydrous magnesium sulfate. The diethyl ether layer was concentrated under reduced pressure, and the concentrate was purified by silica gel column chromatography to give 0.6 g (40%) of the titled compound as an oily matter.

IR(neat): 3312, 2902, 2846, 1651, 1602, 1454 cm$^{-1}$

The following compounds were obtained by a method similar to Example 18.

3-[N-Methyl-N-(4-pyridylmethyl)]aminopropionic acid N-[2-(1-adamantyl) ethyl]-N-pentylamide (Compound No. 18-2)

IR(neat): 2902, 2846, 1643 cm$^{-1}$

2-[2-(4-Pyridyl)ethoxy]acetic acid N-[2-(1-adamantyl) ethyl]-N-pentylamide (Compound No. 18-3)

IR(neat): 2902, 2846, 1650, 1602, 1451, 1113 cm$^{-1}$

EXAMPLE 19

(R)-1-[2-(4-Pyridyl)ethyl]-2-pyrrolidinecarboxylic acid N-[2-(1-adamantyl) ethyl]-1-pentylamide hydrochloride (Compound No. 19-1)

N-t-Butoxycarbonyl-L-proline (1.7 g, 8.0 mmol) was dissolved in anhydrous tetrahydrofuran (20 ml), and the solution was stirred at −15° C. under a nitrogen atmosphere. N-Methylmorpholine (0.90 ml, 8.0 mmol) and isobutyl chlorocarbonate (1.0 ml, 8.0 mmol) were added to the solution. After 10 minutes, a solution of a free base (2.0 g, 8.0 mmol) of Intermediate No. 1-1 in anhydrous tetrahydrofuran (20 ml) was added dropwise to the mixture over five minutes. The whole was stirred at 0° C. for 45 minutes, then the temperature was raised to room temperature, and the whole was stirred overnight. A saturated aqueous sodium hydrogencarbonate solution (50 ml) and ethyl acetate (50 ml) were added to the reaction mixture, and the reaction mixture was distributed. The ethyl acetate layer was washed with a 10% aqueous citric acid solution (50 ml), water (50 ml) and a saturated aqueous sodium chloride solution (50 ml) successively and dried over anhydrous magnesium sulfate. The ethyl acetate layer was concentrated under reduced pressure, and the concentrate was purified by silica gel column chromatography to give 1.9 g (52%) of (R)-1-(t-butoxycarbonyl)-2-pyrrolidinecarboxylic acid N-[2-(1-adamantyl) ethyl]-N-pentylamide, which was the target compound, as an oily matter.

Next, 4 N hydrogen chloride/dioxane (20 ml, 81 mmol) was added to (R)-1-(t-butoxycarbonyl)-2-pyrrolidinecarboxylic acid N-[2-(1-adamantyl) ethyl]-N-pentylamide (1.8 g, 4.0 mmol) under ice-cooling, then the temperature was raised to room temperature, and the mixture was stirred for 1.5 hours. The reaction mixture was concentrated under reduced pressure to give 1.5 g (quantitatively) of (R)-2-pyrrolidinecarboxylic acid N-[2-(1-adamantyl)ethyl]-N-pentylamide hydrochloride as a noncrystalline solid.

Next, (R)-2-pyrrolidinecarboxylic acid N-[2-(1-adamantyl) ethyl]-N-pentylamide hydrochloride (1.4 g, 3.7 mmol) was dissolved in anhydrous N,N-dimethylformamide (40 ml), potassium carbonate (2.6 g, 19 mmol), methyl iodide (1.7 g, 11 mmol) and 4-(2-chloroethyl) pyridine hydrochloride (0.70 g, 3.7 mmol) were added to the solution, and the mixture was stirred at an external temperature of 80° C. overnight. A 2 N aqueous sodium hydroxide solution (70 ml) and diethyl ether (70 ml) were added to the reaction mixture, the reaction mixture was distributed, and the diethyl ether layer was washed with water (70 ml) and a saturated aqueous sodium chloride solution (70 ml) successively and dried over anhydrous magnesium sulfate. The diethyl ether layer was concentrated under reduced pressure, and the concentrate was purified by silica gel column chromatography to give 0.80 g (47%) of the titled compound as an oily matter.

IR(neat): 2902, 2846, 1644 cm$^{-1}$
$[\alpha]^{20}_D$: −48.1° (MeOH, C 1.0)

The following compound was obtained by a method similar to Example 19.

(S)-1-[2-(4-Pyridyl)ethyl]-2-pyrrolidinecarboxylic acid N-[2-(1-adamantyl) ethyl]-N-pentylamide hydrochloride (Compound No. 19-2)

IR(neat): 2902, 2846, 1644, 1601 cm$^{-1}$ $[\alpha]^{20}_D$: +41.6° (MeOH, C 1.0)

EXAMPLE 20

1-[2-(1-Adamantyl)ethyl]-1-[2-(N-ethylamino)ethyl]-3-[3-(4-pyridyl) propyl]urea (Compound No. 20-1)

Lithium aluminum hydride (890 mg, 23.5 mmol) was suspended in anhydrous diethyl ether (10 ml) under a nitrogen atmosphere, and a solution of 1-[2-(acetylamino)ethyl]-1-[2-(1-adamantyl) ethyl]-3-[3-(4-pyridyl)propyl]urea (Compound No. 1-103) (4.86 g, 11.4 mmol) in anhydrous tetrahydrofuran (60 ml) was added dropwise to the suspension under ice-cooling with stirring over two hours. The temperature was raised to room temperature, and the mixture was stirred for 70 hours. Ethyl acetate (25 ml) was added to the reaction mixture under ice-cooling, then a 1 N aqueous sodium hydroxide solution (25 ml) was added thereto, and the whole was filtered with Celite to remove an insoluble matter. The filtrate was distributed with ethyl acetate (25 ml) and water (25 ml), and the organic layer was washed with a saturated aqueous sodium chloride solution (20 ml). The organic layer was dried over anhydrous magnesium sulfate, the solvent was evaporated under reduced pressure, and the residue was purified by silica gel column chromatography to give the titled compound (2.33 g, colorless crystals, 49.8%).

IR(KBr): 3309, 2901, 2845, 1615, 1534 cm$^{-1}$ mp: 96.8-104.9° C.

EXAMPLE 21

3-(4-Pyridylmethylideneamino)propionic acid N-[2-(1-adamantyl) ethyl]-N-pentylamide (Compound No. 21-1)

3-(t-Butoxycarbonylamino)propionic acid (1.0 g, 5.3 mmol) was dissolved in anhydrous tetrahydrofuran (15 ml), and N-methylmorpholine (0.6 ml, 5.5 mmol) was added to the solution. The mixture was stirred at −15° C., and isobutyl chlorocarbonate (0.7 ml, 5.4 mmol) was added thereto. Then, a solution of a free base of 2-(1-adamantyl)-N-pentylethylamine hydrochloride (Intermediate No. 1-1) (1.5 g, 5.3 mmol) in anhydrous tetrahydrofuran (15 ml) was added thereto at −18° C. The whole was stirred at 0° C. for 1.5 hours, ethyl acetate (100 ml) and a saturated aqueous sodium hydrogencarbonate solution (100 ml) were added to the reaction mixture, and the reaction mixture was distributed. The organic layer was washed with a 10% aqueous citric acid solution (100 ml), water (100 ml) and a saturated aqueous sodium chloride solution (100 ml) successively and dried over anhydrous magnesium sulfate. The organic layer was concentrated under reduced pressure, and the concentrate was purified by silica gel column chromatography to give 1.9 g (85%) of 3-(t-butoxycarbonylamino)propionic acid N-[2-(1-adamantyl)ethyl]-N-pentylamide as an oily matter.

A 4.0 N hydrogen chloride/1,4-dioxane solution (22 ml, 88 mmol) was added to 3-(t-butoxycarbonylamino)propionic acid N-[2-(1-adamantyl) ethyl]-N-pentylamide (1.9 g, 4.4 mmol) under ice-cooling, then the temperature was raised to room temperature, and the mixture was stirred for one hour 15 minutes. The reaction mixture was concentrated under reduced pressure to give 1.4 g (89%) of the target hydrochloride. A 1 N aqueous sodium hydroxide solution (80 ml) was added to the hydrochloride, and the whole was extracted with chloroform (80 ml). The chloroform layer was washed with a saturated aqueous sodium chloride solution (80 ml) and dried over anhydrous magnesium sulfate. The chloroform layer was concentrated under reduced pressure to give 3-aminopropionic acid N-[2-(1-adamantyl) ethyl]-N-pentylamide as an oily matter.

3-Aminopropionic acid N-[2-(1-adamantyl)ethyl]-N-pentylamide (1.3 g, 3.9 mmol) was dissolved in anhydrous tetrahydrofuran (10 ml), and the solution was stirred under ice-cooling. 4-Pyridinecarboxyaldehyde (0.42 ml, 4.3 mmol) was added to the solution, and the mixture was stirred at room temperature for three hours. The reaction mixture was concentrated under reduced pressure to give 1.7 g (quantitatively) of the titled compound as an oily matter.

IR(neat): 2901, 1713, 1644, 1454 cm$^{-1}$

EXAMPLE 22

3-(4-Pyridylmethylamino)propionic acid N-[2-(1-adamantyl)ethyl]-N-pentylamide (Compound No. 22-1)

3-(4-Pyridylmethylideneamino)propionic acid N-[2-(1-adamantyl) ethyl]-N-pentylamide (Compound No. 21-1) (1.6 g, 3.9 mmol) was dissolved in methanol, 10% palladium on carbon (catalytic amount) was added to the solution, and the mixture was stirred under hydrogen at 1 atm and room temperature for seven hours. The 10% palladium on carbon was filtered out, the filtrate was concentrated under reduced pressure, and the concentrate was purified by silica gel column chromatography to give 0.58 g (36%) of the titled compound as an oily matter.

IR(neat): 3313, 2902, 2846, 1636, 1451 cm$^{-1}$

EXAMPLE 23

1-[2-(1-Adamantyl)ethyl]-3-[3-[4-(2-cyano)pyridyl]propyl]-1-pentylurea (Compound No. 23-1)

Trimethylsilyl cyanide (1.2 ml, 9.4 mmol) and triethylamine (0.65 ml, 4.7 mmol) were added to a solution of 4-[3-[3-[2-(1-adamantyl) ethyl]-3-pentylureido]propyl]pyridine N-oxide (Compound No. 16-1) (1.0 g, 2.3 mmol) in anhydrous acetonitrile (1.5 ml) at room temperature under a nitrogen atmosphere, and the mixture was refluxed overnight. The reaction mixture was distributed with chloroform (40 ml) and a saturated aqueous sodium hydrogencarbonate solution (40 ml). The organic layer was washed with a saturated aqueous sodium chloride solution (10 ml) and dried over anhydrous magnesium sulfate. The solvent was evaporated under reduced pressure, and the resulting residue was filtered off with diisopropyl ether to give 730 mg (73.0%) of the titled compound as crystals.

IR(KBr): 3334, 2900, 2845, 2234, 1621, 1534 cm$^{-1}$ mp: 112.0-123.0° C.

EXAMPLE 24

1-[2-(1-Adamantyl)ethyl]-3-[3-[4-(2-aminomethyl)pyridyl] propyl]-1-pentylurea (Compound No. 24-1)

A catalytic amount of 10% palladium on carbon was added to a solution of 1-[2-(1-adamantyl)ethyl]-3-[3-[4-(2-cyano) pyridyl]propyl]-1-pentylurea (Compound No. 23-1) (0.20 g, 0.46 mmol) in methanol (2.0 ml) at room temperature under a nitrogen atmosphere, and the mixture was stirred under a hydrogen atmosphere overnight. The reaction mixture was filtered with Celite, the solvent was evaporated under reduced pressure, and the resulting residue was distributed with diethyl ether (50 ml) and water (50 ml). A 2 N aqueous sodium hydroxide solution (10 ml) was added to the aqueous layer, and the whole was further extracted with diethyl ether (50 ml). The combined organic layer was washed with a saturated aqueous sodium chloride solution (10 ml) and dried over anhydrous magnesium sulfate. The solvent was evaporated under reduced pressure, and the resulting residue was filtered off with diisopropyl ether to give 151 mg (74.4%) of the titled compound as crystals.

IR(KBr): 3346, 2901, 2845, 1621, 1538 cm$^{-1}$
mp: 88.0-95.0° C.

EXAMPLE 25

1-[2-(1-Adamantyl)ethyl]-3-[3-[4-(2-carboxy)pyridyl]propyl]-1-pentylurea (Compound No. 25-1)

At room temperature, 6 N hydrochloric acid (1.5 ml, 9.2 mmol) was added to 1-[2-(1-adamantyl)ethyl]-3-[3-[4-(2-cyano) pyridyl]propyl]-1-pentylurea (Compound No. 23-1) (0.20 g, 0.46 mmol), and the mixture was refluxed overnight. The solvent was evaporated under reduced pressure from the reaction mixture, and the resulting crystals were filtered off with acetone. The crystals were dissolved in chloroform (40 ml), and the solution was washed with water (40 ml) and a saturated aqueous sodium chloride solution (10 ml) successively. The organic layer was dried over anhydrous magnesium sulfate, and the solvent was evaporated under reduced pressure to give 132 mg (63.0%) of the titled compound.

IR(KBr): 3326, 2905, 2848, 1704, 1621, 1539 cm$^{-1}$
mp: 130° C.

EXAMPLE 26

1-[2-(1-Adamantyl)ethyl]-3-[3-[4-(2-hydroxymethyl)pyridyl]propyl]-1-pentylurea (Compound No. 26-1)

A 1.0 M solution of a borane-tetrahydrofuran complex in tetrahydrofuran (0.66 ml, 0.66 mmol) was added to a solution of 1-[2-(1-adamantyl)ethyl]-3-[3-[4-(2-carboxy)pyridyl]propyl]-1-pentylurea (Compound No. 25-1) (0.10 g, 0.22 mmol) in anhydrous tetrahydrofuran (0.7 ml) under a nitrogen atmosphere and ice-cooling, and the mixture was stirred at room temperature for 4.5 hours. Water (3 ml) was added to the reaction mixture under ice-cooling, and the reaction mixture was distributed with ethyl acetate (15 ml) and a 0.1% aqueous sodium hydroxide solution (10 ml). The organic layer was washed with a saturated aqueous sodium chloride solution (10 ml) and dried over anhydrous magnesium sulfate. The solvent was evaporated under reduced pressure, and the resulting residue was purified by silica gel column chromatography to give 53 mg of a borane complex salt of the titled compound as an oily matter.

IR(neat): 3342, 2904, 1630, 1531 cm$^{-1}$

EXAMPLE 27

1-[2-(1-Adamantyl)ethyl]-3-[3-[4-(2-methyl)pyridyl]propyl]-1-pentylurea (Compound No. 27-1)

p-Toluenesulfonyl chloride (23 mg, 0.12 mmol) was added to a solution of 1-[2-(1-Adamantyl)ethyl]-3-[3-[4-(2-hydroxymethyl) pyridyl]propyl]-1-pentylurea (Compound No. 26-1) (50 mg, 0.11 mmol) and triethylamine (20 μl, 0.13 mmol) in anhydrous dichloromethane (1.0 ml) at room temperature, and the mixture was stirred at room temperature overnight. The reaction mixture was distributed with chloroform (9 ml) and water (10 ml), and the organic layer was dried over anhydrous magnesium sulfate. The solvent was evaporated under reduced pressure, and the resulting residue was purified by silica gel column chromatography. A catalytic amount of 10% palladium on carbon was added to a solution of the obtained p-toluenesulfonyl form in methanol (1 ml), and the mixture was stirred under a hydrogen atmosphere for seven days to give 18 mg (38%) of the titled compound as an oily matter.

IR(neat): 3345, 2903, 2847, 1624, 1534 cm$^{-1}$

EXAMPLE 28

1-[2-(1-Adamantyl)ethyl]-1-(2-aminoethyl)-3-[3-(4-pyridyl) propyl]urea (Compound No. 28-1)

Under ice-cooling, 6 N hydrochloric acid (15 ml) was added to a solution of 1-[2-(acetylamino)ethyl]-1-[2-(1-adamantyl)ethyl]-3-[3-(4-pyridyl)propyl]urea (Compound No. 1-103) (1.02 g, 2.39 mmol) in methanol (10 ml), and the mixture was heated at 90° C. with stirring for three days. The reaction mixture was neutralized with a 1 N aqueous sodium hydroxide solution (10 ml), chloroform (50 ml) and water (10 ml) were added thereto, and layers were separated. The organic layer was washed with a saturated aqueous sodium chloride solution (50 ml) and dried over anhydrous magnesium sulfate, and the solvent was evaporated under reduced pressure. The residue was purified by silica gel column chromatography to give 200 mg (21.7%) of the titled compound as an oily matter.

IR(neat): 3306, 2902, 2846, 1629, 1605, 1537, 753 cm$^{-1}$

EXAMPLE 29

4-[2-[N-[2-(1-Adamantyl)ethyl]-N-pentylcarbonylmethoxy]ethoxy]-pyridine N-oxide (Compound No. 29-1)

2-(1-Adamantyl)-N-pentylethylamine hydrochloride (Intermediate No. 1-1) (0.50 g, 1.7 mmol) was added to a solution of diglycolyl chloride (0.31 ml, 2.6 mmol) and triethylamine (0.70 ml, 5.1 mmol) in anhydrous dichloromethane (6 ml) under ice-cooling, and the mixture was stirred at room temperature overnight. Methanol (5 ml) was added to the reaction mixture, and the whole was stirred for three hours. The solvent was evaporated under reduced pressure, the residue was distributed with ethyl acetate and water (15 ml respectively), and the organic layer was washed with a saturated aqueous sodium chloride solution (5 ml) and dried over anhydrous magnesium sulfate. The solvent was evaporated under reduced pressure, the resulting residue was purified by silica gel column chromatography to give 0.39 g (60%) of 2-methoxycarbonylmethoxyacetic acid N-[2-(1-adamantyl) ethyl]-N-pentylamide as an oily matter.

Next, sodium borohydride (0.18 g, 4.8 mmol) was added to a solution of 2-methoxycarbonylmethoxyacetic acid N-[2-(1-adamantyl) ethyl]-N-pentylamide (0.37 g, 0.96 mmol) in methanol (3 ml) under ice-cooling, and the mixture was stirred at room temperature overnight. Water (10 ml) was added to the reaction mixture, and the whole was stirred for 10 minutes. Then, water (20 ml) and ethyl acetate (30 ml) were added thereto, and layers were separated. The organic layer was washed with a saturated aqueous sodium chloride solution (10 ml) and dried over anhydrous magnesium sulfate. The solvent was evaporated under reduced pressure, and the resulting residue was purified by silica gel column chromatography to give 74 mg (22%) of 2-(2-hydroxyethoxy)acetic acid N-[2-(1-adamantyl)ethyl]-N-pentylamide as an oily matter.

Next, 4-nitropyridine N-oxide (24 mg, 0.17 mmol) and potassium carbonate (28 mg, 0.20 mmol) were added to a solution of 2-(2-hydroxyethoxy)acetic acid N-[2-(1-adamantyl)ethyl]-N-pentylamide (60 mg, 0.17 mmol) in N,N-dimethylformamide (0.4 ml) at room temperature, and the mixture was stirred at 60° C. for two days. The solvent was evaporated under reduced pressure, and the resulting residue was purified by silica gel column chromatography to give 39 mg of the titled compound as an oily matter.

$^1$H-NMR (400 MHz, CDCl$_3$) δ0.87-0.93 (m, 3H), 1.20-1.40 (m, 6H), 1.47-1.60 (m, 8H), 1.61-1.67 (m, 3H), 1.68-1.76 (m, 3H), 1.97 (brs, 3H), 3.10-3.19 (m, 2H), 3.25-3.36 (m, 2H), 3.94-3.98 (m, 2H), 4.20-4.27 (m, 4H), 6.81-6.86 (m, 2H), 8.10-8.15 (m, 2H)

EXAMPLE 30

2-[2-(4-Pyridyloxy)ethoxy]acetic acid N-[2-(1-adamantyl)ethyl]-N-pentylamide (Compound No. 30-1)

A catalytic amount of 10% palladium on carbon was added to a solution of 4-[2-[N-[2-(1-adamantyl)ethyl]-N-pentylcarbonylmethoxy]ethoxy]-pyridine N-oxide (Compound No. 29-1) (39 mg, 0.088 mmol) and acetic anhydride (20 µl, 0.18 mmol) in a mixed solvent of methanol (0.4 ml) and acetic acid (0.1 ml) at room temperature under a nitrogen atmosphere, and the mixture was stirred under a hydrogen atmosphere for four days. The reaction mixture was filtered with Celite, the solvent was evaporated under reduced pressure from the filtrate, and the residue was distributed with ethyl acetate (20 ml) and a saturated aqueous sodium hydrogencarbonate solution (20 ml). The organic layer was washed with a saturated aqueous sodium chloride solution (10 ml) and dried over anhydrous magnesium sulfate. The solvent was evaporated, and the resulting residue was purified by silica gel column chromatography to give 16 mg (42%) of the titled compound as an oily matter.

IR(neat): 2903, 1651, 1592 cm$^{-1}$

EXAMPLE 31

1-[2-(1-Adamantyl)ethyl]-3-[3-oxo-3-(4-pyridyl)propyl]-1-pentylurea (Compound No. 31-1)

1,1,1-Triacetoxy-1,1-dihydro-1,2-benziodoxol-3(1H)-one (221 mg, 0.520 mmol) was added to a solution of 1-[2-(1-adamantyl)ethyl]-3-[3-hydroxy-3-(4-pyridyl)propyl]-1-pentylurea (100 mg, 0.234 mmol) in anhydrous dichloromethane (2 ml) under ice-cooling, the temperature was raised to room temperature, and the mixture was stirred for one hour. The reaction mixture was cooled with ice again, ethyl acetate (10 ml), a saturated aqueous sodium sulfite solution (5 ml) and a saturated aqueous sodium hydrogencarbonate solution (5 ml) were added to the reaction mixture, and the whole was stirred for 15 minutes. The reaction mixture was distributed with ethyl acetate (50 ml) and water (10 ml), and the organic layer was washed with a saturated aqueous sodium sulfite solution (5 ml), a saturated aqueous sodium hydrogencarbonate solution (5 ml) and a saturated aqueous sodium chloride solution (25 ml) successively. The organic layer was dried over anhydrous magnesium sulfate, and the solvent was evaporated under reduced pressure to give 87.3 mg (87.8%) of the titled compound as colorless crystals.

IR(KBr): 3328, 2901, 2847, 1710, 1619, 1540 cm$^{-1}$
mp: 103.5-104.0° C.

[C] Formulation

General formulation examples of oral preparations and injections using the present compounds are shown below.

1) Tablet

| Formulation 1 (in 100 mg) | |
|---|---|
| Present compound | 1 mg |
| Lactose | 66.4 mg |
| Cornstarch | 20 mg |
| Calcium carboxymethylcellulose | 6 mg |
| Hydroxypropylcellulose | 4 mg |
| Magnesium stearate | 0.6 mg |

Tablets according to the formulation as above are coated with 2 mg/tablet of a coating agent (this is a conventional coating agent such as hydroxypropylmethylcellulose, macrogol or silicone resin) to obtain desired coated tablets. (The same is applied to tablets mentioned below.) Desired tablets can be obtained by changing the amounts of the present compound and the additives appropriately.

2) Capsule

| Formulation 1 (in 150 mg) | |
|---|---|
| Present compound | 5 mg |
| Lactose | 145 mg |

Desired capsules can be obtained by changing the mixing ratio of the present compound to lactose appropriately.

3) Injection

| Formulation 1 (in 10 ml) | |
|---|---|
| Present compound | 10-100 mg |
| Sodium chloride | 90 mg |
| Sodium hydroxide | q.s. |
| Hydrochloric acid | q.s. |
| Sterile purified water | q.s. |

Desired injections can be obtained by changing the mixing ratio of the present compound to the additives appropriately.

[D] Pharmacological Test

Inhibitory effects on TNF-α production induced by lipopolysaccharide (LPS) stimulation were studied by in vivo tests according to the method of Tsuji et al. (Inflamm. res. 46 (1997) 193-198).

Female rats (five per group), body weight of about 200 g, about eight weeks old, were used as test animals. LPS from Salmonella was dissolved in physiological saline to prepare an LPS solution (1 mg/ml). Each test substance was dissolved or uniformly suspended in a 1% methylcellulose solution to give test substance-preparation liquids.

The above-mentioned LPS solution (0.5 ml/kg) was administered to a footpad of the rat. Immediately after the LPS administration, the test substance-preparation liquid (containing 10 mg/kg or 3 mg/kg test substance) was orally administered. Two hours after the LPS administration, blood was collected from abdominal aorta and was centrifuged at 4° C. and 3000 rpm for ten minutes. TNF-α levels in the obtained plasma were measured with a rat TNF-α-specific ELISA kit. TNF-α was not observed in the plasma with respect to an LPS-non-administered group (control).

Inhibition rates of TNF-α production of the test substances were determined by the following equation.

$$\text{Inhibition rate (\%)} = [(A-B)/A] \times 100$$

A: TNF-α level in plasma of test substance-nonadministered group

B: TNF-α level in plasma of test substance-administered group (Results)

Calculating TNF-α production inhibition rates (%) when administered the test substances (10 mg/kg or 3 mg/kg) orally to the rats, many of the present compounds exhibited high inhibition rates of production. Table 1 shows typical test results by oral administration of 10 mg/kg, and Table 2 shows typical test results by oral administration of 3 mg/kg.

TABLE 1

| Test substance | Inhibition rate (%) |
|---|---|
| Compound No. 1-1 | 92.1 |
| Compound No. 1-18 | 78.9 |
| Compound No. 1-20 | 60.0 |
| Compound No. 1-22 | 87.0 |
| Compound No. 1-24 | 95.8 |
| Compound No. 1-25 | 89.0 |
| Compound No. 1-26 | 95.5 |
| Compound No. 1-27 | 81.3 |
| Compound No. 1-28 | 90.4 |
| Compound No. 1-31 | 92.6 |
| Compound No. 1-32 | 62.4 |
| Compound No. 1-34 | 70.8 |
| Compound No. 1-35 | 82.5 |
| Compound No. 1-37 | 84.3 |
| Compound No. 1-38 | 92.3 |
| Compound No. 1-42 | 86.7 |
| Compound No. 1-43 | 67.6 |
| Compound No. 1-44 | 93.7 |
| Compound No. 1-45 | 91.1 |
| Compound No. 1-55 | 78.1 |
| Compound No. 1-66 | 79.4 |
| Compound No. 1-68 | 79.0 |
| Compound No. 1-70 | 87.9 |
| Compound No. 1-120 | 95.1 |
| Compound No. 1-139 | 94.1 |
| Compound No. 2-1 | 91.5 |
| Compound No. 2-3 | 51.8 |
| Compound No. 6-1 | 50.5 |
| Compound No. 7-1 | 71.5 |
| Compound No. 11-1 | 50.8 |

TABLE 2

| Test substance | Inhibition rate (%) |
|---|---|
| Compound No. 1-10 | 63.0 |
| Compound No. 1-78 | 61.5 |
| Compound No. 1-84 | 35.5 |
| Compound No. 1-95 | 70.8 |
| Compound No. 1-111 | 85.1 |
| Compound No. 1-137 | 82.1 |
| Compound No. 2-7 | 78.7 |
| Compound No. 2-9 | 84.5 |
| Compound No. 2-11 | 53.5 |
| Compound No. 2-14 | 87.3 |
| Compound No. 2-15 | 68.1 |
| Compound No. 2-18 | 87.3 |
| Compound No. 2-20 | 82.1 |
| Compound No. 3-4 | 76.1 |
| Compound No. 4-1 | 42.8 |
| Compound No. 5-3 | 49.4 |
| Compound No. 5-4 | 62.6 |
| Compound No. 5-5 | 42.8 |
| Compound No. 5-6 | 41.7 |
| Compound No. 10-16 | 62.8 |
| Compound No. 10-17 | 53.8 |
| Compound No. 14-1 | 36.3 |
| Compound No. 15-1 | 73.8 |
| Compound No. 16-1 | 74.3 |
| Compound No. 18-1 | 55.7 |
| Compound No. 18-3 | 56.6 |
| Compound No. 27-1 | 68.6 |
| Compound No. 31-1 | 46.8 |

INDUSTRIAL APPLICABILITY

The results of the pharmacological test clearly show that since the present compounds have excellent TNF-α production inhibitory effects, the present compounds can be applied to extensive medical uses as therapeutic agents for diseases in which TNF-α participates, for example, autoimmune diseases such as rheumatoid arthritis, Crohn's disease and systemic lupus erythematosus, cachexia, acute infectious disease, allergy, pyrexia, anemia, diabetes and the like.

What is claimed is:

1. A compound represented by the following formula 1 or a salt thereof,

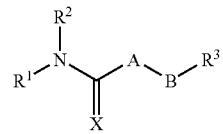

wherein A is —(NR$^4$)—;

B is alkylene or alkenylene;

wherein the alkylene and alkenylene is unsubstituted or substituted by hydroxy, alkoxy, cycloalkyl, aryl, siloxy or a saturated or unsaturated heterocycle;

R$^1$, R$^2$ and R$^4$, being the same or different, are hydrogen, alkyl, alkenyl, alkynyl, cycloalkyl, cycloalkenyl, acyl or amino, wherein the alkyl, alkenyl, alkynyl, cycloalkyl or cycloalkenyl are unsubstituted or substituted by halogen, amino, cycloalkyl, adamantyl, aryl, carboxy, alkoxycarbonyl, aryloxycarbonyl, aminocarbonyl, cyano or a saturated or unsaturated heterocycle, said heterocycle being a five to twenty membered heterocycle containing one to four heteroatoms selected from the group consisting of nitrogen, oxygen and sulfur;

at least one of R$^1$, R$^2$, and R$^4$ is adamantylalkyl, adamantyloxyalkyl, adamantylaminoalkyl or adamantylaminocarbonylalkyl;

R$^3$ is a substituted or unsubstituted pyridine ring;

X is O or S;

each hydrogen of the aforesaid amino, and aminocarbonyl can be replaced with alkyl, cycloalkyl, adamantyl, adamantylalkyl, aryl, arylalkyl, acyl, alkoxyalkyl, alkoxycarbonyl, alkylaminocarbonyl, cycloalkyloxycarbonyl, arylalkoxycarbonyl, alkylsulfonyl, arylsulfonyl, halogenoalkyloxycarbonyl, imidazolylcarbonyl, pyridylcarbonyl, a saturated or unsaturated heterocycle, or alkyl substituted by a saturated or unsaturated heterocycle, said heterocycle being a five to twenty membered heterocycle containing one to four heteroatoms selected from the group consisting of nitrogen, oxygen and sulfur.

2. The compound or a salt thereof as claimed in claim 1, wherein at least one of R$^1$ and R$^2$ is adamantylalkyl, adamantyloxyalkyl, adamantylaminoalkyl or adamantylaminocarbonylalkyl.

3. The compound or a salt thereof as claimed in claim 1, wherein at least one of $R^1$ and $R^2$ is adamantylalkyl.

4. The compound or a salt thereof as claimed in claim 1, wherein A is —$(NR^4)$—;

B is alkylene or alkenylene;

wherein the alkylene is unsubstitued or substituted by hydroxy, alkoxy, aryl, siloxy or a saturated or unsaturated heterocycle, said heterocycle being a five to twenty membered heterocycle containing one to four heteroatoms selected from the group consisting of nitrogen, oxygen and sulfur;

$R^1$ is hydrogen, alkyl, alkenyl, alkynyl, cycloalkyl, cycloalkenyl, hydroxy or amino, wherein the alkyl, alkenyl, alkynyl, cycloalkyl or cycloalkenyl is unsubstituted or substituted by halogen, amino, cycloalkyl, aryl, carboxy, alkoxycarbonyl, alkylaminocarbonyl, adamantyl, aryloxycarbonyl, cyano or saturated or unsaturated heterocycle, said heterocycle being a five to twenty membered heterocycle containing one to four heteroatoms selected from the group consisting of nitrogen, oxygen and sulfur, and each hydrogen of the amino, and aminocarbonyl can be replaced with alkyl, cycloalkyl, aryl, arylalkyl, acyl, alkoxycarbonyl, cycloalkyloxycarbonyl, arylalkoxycarbonyl, halogenoalkyloxycarbonyl, imidazolylcarbonyl, an unsaturated heterocycle, and heterocycle being a fire to twenty membered heterocycle containing one to four heteroatoms selected from the group consisting of nitrogen, oxygen and sulfur, or alkyl substituted by an unsaturated heterocycle, said heterocycle being a five to twenty membered heterocycle containing one to four heteroatoms selected from the group consisting of nitrogen, oxygen and sulfur;

$R^2$ is adamantylalkyl, adamantyloxyalkyl, adamantylaminoalkyl or adamantylaminocarbonylalkyl;

$R^3$ is a substituted or unsubstituted pyridine ring;

$R^4$ is hydrogen, alkyl, adamantylalkyl, carboxyalkyl, alkoxycarbonyl, alkoxycarbonylalkyl, amino, alkylamino, acylamino or alkoxycarbonylamino; and X is O or S.

5. The compound or a salt thereof as claimed in claim 4, wherein $R^2$ is adamantylalkyl and $R^3$ is a pyridine ring.

6. The compound or a salt thereof as claimed in claim 4, wherein A is —$(NR^4)$—;

B is alkylene or alkenylene;

$R^1$ is alkyl or alkenyl, wherein the alkyl is unsubstituted or substituted by halogen or amino, wherein the amino is unsubstituted or substituted by alkyl, acyl, arylalkyloxycarbonyl, cycloalkyloxycarbonyl or alkoxycarbonyl;

$R^2$ is adamantylalkyl;

R is a pyridine ring;

$R^4$ is hydrogen; and

X is O.

7. A pharmaceutical composition comprising a pharmacologically effective amount of the compound or a salt thereof as claimed in claim 1 as an active ingredient and a pharmacologically acceptable additive.

8. A method of inhibiting TNF-α production comprising administering to a human a composition comprising an effective amount of the compound as claimed in claim 1 and a pharmacologically acceptable additive.

9. A method of treating rheumatoid arthritis or Crohn's disease comprising administering to a human a composition comprising an effective amount of the compound as claimed in claim 1 and a pharmacologically acceptable additive.

* * * * *